US011173109B2

(12) United States Patent
Chan et al.

(10) Patent No.: US 11,173,109 B2
(45) Date of Patent: Nov. 16, 2021

(54) COMPOSITIONS IN THE FORM OF AN INJECTABLE AQUEOUS SOLUTION COMPRISING AMYLIN, AN AMYLIN RECEPTOR AGONIST OR AN AMYLIN ANALOG AND A CO-POLYAMINO ACID

(71) Applicant: ADOCIA, Lyons (FR)

(72) Inventors: You-Ping Chan, Ternay (FR); Alexandre Geissler, Lyons (FR); Romain Noel, Villeurbanne (FR); Walter Roger, Lyons (FR); Richard Charvet, Rillieux la Pape (FR); Nicolas Laurent, Miribel (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/213,776

(22) Filed: Dec. 7, 2018

(65) Prior Publication Data

US 2019/0274954 A1 Sep. 12, 2019

Related U.S. Application Data

(60) Provisional application No. 62/606,139, filed on Dec. 7, 2017.

(30) Foreign Application Priority Data

Jun. 29, 2018 (EP) .................... 18181028

(51) Int. Cl.
A61K 38/00 (2006.01)
A61K 9/00 (2006.01)
A61K 47/64 (2017.01)
A61K 9/08 (2006.01)
A61K 38/28 (2006.01)
A61K 47/18 (2017.01)
C07C 233/00 (2006.01)
A61K 47/10 (2017.01)
A61K 47/02 (2006.01)
C07D 403/12 (2006.01)
C07D 403/14 (2006.01)
A61K 47/34 (2017.01)
C07K 2/00 (2006.01)
C07D 207/16 (2006.01)
A61P 5/48 (2006.01)

(52) U.S. Cl.
CPC .............. *A61K 9/0019* (2013.01); *A61K 9/08* (2013.01); *A61K 38/28* (2013.01); *A61K 47/02* (2013.01); *A61K 47/10* (2013.01); *A61K 47/183* (2013.01); *A61K 47/34* (2013.01); *A61K 47/6455* (2017.08); *C07C 233/00* (2013.01); *C07D 207/16* (2013.01); *C07D 403/12* (2013.01); *C07D 403/14* (2013.01); *C07K 2/00* (2013.01); *A61P 5/48* (2018.01)

(58) Field of Classification Search
None
See application file for complete search history.

(56) References Cited

U.S. PATENT DOCUMENTS

| 5,124,314 | A | 6/1992 | Cooper |
|---|---|---|---|
| 5,234,906 | A | 8/1993 | Young et al. |
| 5,686,411 | A | 11/1997 | Gaeta et al. |
| 6,114,304 | A | 9/2000 | Kolterman et al. |
| 6,410,511 | B2 | 6/2002 | L'Italien et al. |
| 8,084,493 | B1 | 12/2011 | Sung et al. |
| 2001/0043934 | A1 | 11/2001 | L'Italien et al. |
| 2011/0082080 | A1* | 4/2011 | Levetan .................. A61P 3/06 514/7.3 |
| 2015/0320876 | A1 | 11/2015 | Chen et al. |
| 2016/0001002 | A1 | 1/2016 | Yodfat et al. |

FOREIGN PATENT DOCUMENTS

| EP | 0 347 724 A1 | 12/1989 |
|---|---|---|
| EP | 0 499 521 A1 | 8/1992 |
| FR | 2801226 A1 | 5/2001 |
| FR | 2 840 614 A1 | 12/2003 |
| FR | 2 855 521 A1 | 12/2004 |
| FR | 2 910 318 A1 | 6/2008 |
| FR | 2 985 428 A1 | 7/2013 |
| FR | 2 985 429 A1 | 7/2013 |
| WO | 03/101395 A2 | 12/2003 |
| WO | 2007/104786 A1 | 9/2007 |
| WO | 2009/077844 A2 | 6/2009 |
| WO | 2009/089506 A1 | 7/2009 |
| WO | 2013/067022 A1 | 5/2013 |
| WO | 2013/104861 A1 | 7/2013 |
| WO | 2015/114171 A1 | 8/2015 |
| WO | 2017/211916 A1 | 12/2017 |

(Continued)

OTHER PUBLICATIONS

Sep. 15, 2020 Office Action issued in U.S. Appl. No. 16/213,865.
Gerich; "Control of glycaemia;" Bailliere's Clinical Endocrinology and Metabolism; 1993; pp. 551-585; vol. 7, No. 3.
Schmitz et al.; "Amylin Agonists: A Novel Approach in the Treatment of Diabetes;" Diabetes; 2004; pp. S233-S238; vol. 53, No. 3.
Yan et al.; "Design of a mimic of nonamyloidogenic and bioactive human islet amyloid polypeptide (IAPP) as nanomolar affinity inhibitor of IAPP cytotoxic fibrillogenesis;" PNAS; 2006; pp. 2046-2051; vol. 103, No. 7.

(Continued)

Primary Examiner — Jeanette M Lieb
(74) Attorney, Agent, or Firm — Oliff PLC

(57) ABSTRACT

A composition in the form of an injectable aqueous solution, wherein the pH is comprised from 6.0 to 8.0, includes at least:
a) amylin, an amylin receptor agonist or an amylin analog; and
b) a co-polyamino acid bearing carboxylate charges and hydrophobic radicals Hy, wherein the composition does not comprise a basal insulin wherein the isoelectric point pI is comprised from 5.8 to 8.5. The composition may further include a prandial insulin.

18 Claims, 1 Drawing Sheet

(56) References Cited

FOREIGN PATENT DOCUMENTS

| WO | 2017/211918 A1 | 12/2017 |
|---|---|---|
| WO | 2018/122278 A1 | 7/2018 |

OTHER PUBLICATIONS

Annex 1—Summary of product characteristics of ADIPRA®; Sep. 14, 2009.

Naiki et al.; "Fluorometric Determination of Amyloid Fibrils in Vitro Using the Fluorescent Dye, Thioflavine T1" Analytical Biochemistry; 1989; pp. 244-249; vol. 177.

Levine III; "Quantifications of β-Sheet Amyloid Fibril Structures with Thioflavin T;" Methods in Enzymology; 1999; pp. 274-284; vol. 309.

Bhatnagar et al.; "Structure-Activity Relationships of Novel Hematoregulatory Peptides;" J. Med. Chem.; 1996; pp. 3814-3819; vol. 39.

Hoppmann et al.; "Intramolecular bridges formed by photoswitchable click amino acids;" Beilstein J. Org. Chem. 2012; pp. 884-889; vol. 8.

Burnett et al.; "Safety Assessment of Amino Acid Alkyl Amides as Used in Cosmetics;" International Journal of Toxicology; 2017; pp. 17S-56S; vol. 36, No. 1.

Wu et al.; "Interplay of Chemical Microenvironment and Redox Environment on Thiol-Disulfide Exchange Kinetics;" Chem. Eur. J.; 2011; pp. 10064-10070; vol. 17.

Liang et al.; "Distinct optical and kinetic responses from E/Z isomers of caspase probes with aggregation-induced emission characteristics;" J. Mater. Chem. B.; 2014; pp. 4363-4370; vol. 2.

Liu et al.; "Fluorescent Molecular Probes V: A Sensitive Caspase-3 Substrate for Fluorometric Assays;" Bioorganic & Medicinal Chemistry Letters; 1999; pp. 3231-3236; vol. 9.

Leishman et al.; "Lipidomics profile of a NAPE-PLD KO mouse provides evidence of a broader role of this enzyme in lipid metabolism in the brain;" Biochimica et Biophysica Acta; 2016; pp. 491-500; vol. 1861.

Schlitzer et al.; "Non-peptidic, Non-prenylic Bisubstrate Farnesyltransferase Inhibitors, 4. Effect on Farnesyltransferase Inhibitory Activity of Conformational Restrictions in the Central Group;" 2000; pp. 117-124; vol. 5.

Feb. 12, 2019 Search Report issued in International Patent Application No. PCT/EP2018/083964.

Feb. 15, 2019 Search Report issued in International Patent Application No. PCT/EP2018/083943.

Goldsbury CS, et al.; "Polymorphic Fibrillar Assembly of Human Amylin". J. Struct. Biol., vol. 119, pp. 17-27, 1997.

Deming, Timothy "Polypeptide and Polypeptide Hybrid Copolymer Synthesis via NCA Polymerization;" Adv. Polym. Sci, vol. 202. pp. 1-18, 2006.

Deming, Timothy. "Facile synthesis of block copolypeptides of defined architecture". Nature, vol. 390, pp. 386-389, 1997.

Lu, Hua et al. "Hexamethyldisilazane-Mediated Controlled Polymerization of a-Amino Acid N-Carboxyanhydrides". J. Am. Chem. Soc.vol. 129, pp. 14114-14115, 2007.

Lu, Hua et al. "N-Trimethylsilyl Amines for Controlled Ring-Opening Polymerization of Amino Acid N-Carboxyanhydrides and Facile End Group Functionalization of Polypeptides". J. Am. Chem. Soc, vol. 130., pp. 12562-12563, 2008.

Mar. 8, 2019 Search Report issued in International Application No. PCT/EP2018/084063.

U.S. Appl. No. 16/213,865, filed Dec. 7, 2018 in the name of Chan et al.

U.S. Appl. No. 16/213,881, filed Dec. 7, 2018 in the name of Geissler.

Gonzalez, Jose Vicente et al. "Polypeptides and polyaminoacids in drug delivery." Expert Opinion, vol. 9 No. 2, pp. 183-201, 2012.

Oct. 28, 2020 Office Action issued in U.S. Appl. No. 16/213,881.

May 19, 2021 Notice of Allowance issued in U.S. Appl. No. 16/213,865.

\* cited by examiner

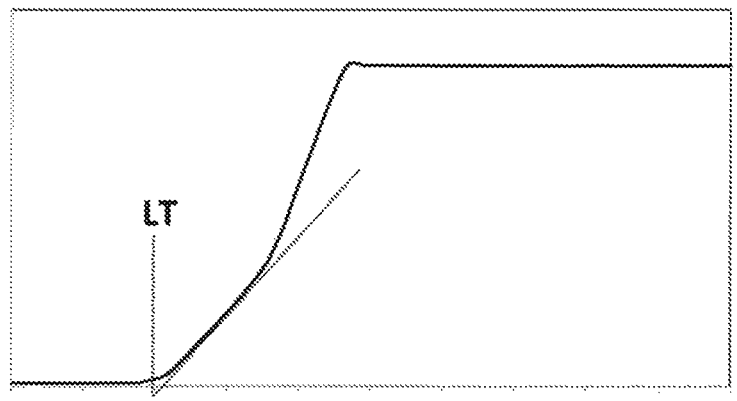

COMPOSITIONS IN THE FORM OF AN INJECTABLE AQUEOUS SOLUTION COMPRISING AMYLIN, AN AMYLIN RECEPTOR AGONIST OR AN AMYLIN ANALOG AND A CO-POLYAMINO ACID

The invention relates to therapies by injecting amylin, amylin receptor agonist or amylin analog for treating diabetes.

The invention relates to a composition in the form of an injectable aqueous solution, wherein the pH is comprised from 6.0 to 8.0, comprising at least amylin, an amylin receptor agonist or an amylin analog and a co-polyamino acid bearing carboxylate charges carboxylates and hydrophobic radicals according to the invention and compositions further comprising an insulin (excluding basal insulins whose isoelectric point pI is comprised from 5.8 to 8.5). The invention also relates to pharmaceutical formulations comprising the compositions according to the invention. Finally, the invention also relates to the use of the co-polyamino acids bearing carboxylate charges and hydrophobic radicals according to the invention for stabilizing amylin, amylin receptor agonist or amylin analog compositions as well as amylin, amylin receptor agonist or amylin analog compositions further comprising an insulin.

In one embodiment, the compositions according to the invention comprise no basal insulin whose isoelectric point pI is comprised from 5.8 to 8.5, and particularly no insulin glargine.

Basal insulin whose isoelectric point is comprised from 5.8 to 8.5 denotes an insulin insoluble at pH 7 and wherein the duration of action is comprised from 8 to 24 hours or greater than 24 hours in standard diabetes models.

Type 1 diabetes is an autoimmune disease resulting in the destruction of pancreatic beta cells. These cells are known to produce insulin, the primary role whereof is to regulate glucose utilization in peripheral tissues (Gerich 1993 Control of glycaemia). Consequently, patients with type 1 diabetes suffer from chronic hyperglycemia and are required to self-administer exogenous insulin in order to limit this hyperglycemia. Insulin therapy has helped change the life expectancy of these patients dramatically. However, blood sugar control by means of exogenous insulin is not optimal, in particular after ingesting a meal. This is linked with the fact that these patients produce glucagon after ingesting a meal, which gives rise to the release of a portion of the glucose stored in the liver, which is not the case in healthy subjects. This glucagon-mediated glucose production worsens the blood sugar regulation problem in these patients.

It has been demonstrated that amylin, another hormone produced by pancreatic beta cells and therefore also deficient in type 1 diabetic patients, plays a key role in post-prandial blood glucose regulation. Amylin, also known as "islet amyloid polypeptide" or IAPP, is a peptide of 37 amino acids which is co-stored and co-secreted with insulin (Schmitz 2004 Amylin Agonists). This peptide is described as blocking glucagon production by pancreatic alpha cells. Thus, insulin and amylin have complementary and synergistic roles, since insulin helps lower the blood glucose concentration whereas amylin helps lower the entry of endogenous glucose into the blood by inhibiting the production (secretion) of endogenous glucagon.

This issue of post-prandial blood sugar regulation is relatively similar for patients with type 2 diabetes treated with insulin insofar as their illness has resulted in a very significant loss of their mass of beta cells and, consequently, of their ability to produce insulin and amylin.

Human amylin has properties which are not compatible with pharmaceutical requirements in terms of solubility and stability (Goldsbury C S, Cooper G J, Goldie K N, Muller S A, Saafi E L, Gruijters W T, Misur M P, Engel A, Aebi U, Kistler J: Polymorphic fibrillar assembly of human amylin. J Struct Biol 119:17-27, 1997). Amylin is known to form amyloid fibers which result in the formation of plaques which are insoluble in water. Although it is a natural hormone, it was necessary to develop an analog so as to solve these solubility problems.

The physicochemical properties of amylin thus render the use thereof impossible: amylin is only stable for about fifteen minutes at acidic pH, and for less than one minute at neutral pH.

The company Amylin has developed an amylin analog, pramlintide, to remedy the lack of stability of human amylin. This product marketed under the trade name Symlin was approved in 2005 by the FDA for the treatment of type 1 and type 2 diabetics. It must be administered subcutaneously three times per day, within one hour prior to the meal so as to improve post-prandial blood sugar control. This peptide is formulated at acidic pH and is described as fibrillating when the pH of the solution is greater than 5.5. Analog variants are described in the U.S. Pat. No. 5,686,411.

This analog is thus not satisfactory in terms of stability when a formulation at neutral pH is envisaged.

To date, there is no means for stabilizing human amylin in order to make a pharmaceutical product therewith. However, it would be advantageous for patients to have access to the human form of this physiological hormone. It would also be advantageous to be able to formulate an analog or an amylin receptor agonist at neutral pH.

Furthermore, there would be a benefit of being able to mix in aqueous solution amylin, an amylin analog, or an amylin receptor agonist, with a prandial insulin as the two substances are to be administered before meals. This would make it possible moreover to mimic the physiology since these two hormones are co-secreted by beta cells in response to a meal in order to improve post-prandial blood sugar control.

However, in view of the fact that prandial insulin solutions have a pH close to neutrality for chemical stability reasons, it is not possible to obtain an aqueous solution meeting pharmaceutical requirements in terms of solubility and stability.

For this reason, patent application US2016/001002 by ROCHE describes a pump containing two separate reservoirs so as to enable the co-administration of these two hormones with a single medical device. However, this patent does not solve the problem of mixing these two hormones in solution which would make it possible to administer them with conventional pumps already on the market that only contain one reservoir.

Patent application WO2013067022 by XERIS provides a solution to the problem in respect of stability of amylin and of the compatibility thereof with insulin using an organic solvent instead of water. The absence of water seems to solve stability problems but the use of an organic solvent poses problems in respect of long-term safety of use for diabetic patients and also compatibility problems with standard medical devices, in terms of the tubing, seals and plasticizers used.

Patent application WO2007104786 by NOVO NORDISK describes a method for stabilizing a solution of pramlintide, which is an amylin analog, and insulin by adding a phospholipid, derived from glycerophosphoglycerol, in particular dimyristoyl glycerophosphoglycerol (DMPG). However, this solution requires the use of large quantities of DMPG which may pose a problem in respect of local tolerance. Moreover, DMPG results in compositions exhibiting relatively poor physical stabilities at 0-4° C. as described in the application WO2018122278.

To the applicant's knowledge, there is no satisfactory means for combining in aqueous solution a prandial insulin and human amylin, an amylin receptor agonist or an amylin analog so as to be suitable for being administered with conventional devices.

The acidic formulation pH and rapid fibrillation are obstacles to obtain a pharmaceutical formulation at neutral pH based on amylin and pramlintide, but also an obstacle to combine amylin or pramlintide with other active pharmaceutical ingredients, in particular peptides or proteins.

BRIEF DESCRIPTION OF THE DRAWING

FIG. 1 is an example of a graphic determination of monitoring of the fluorescence of Thioflavin T, and showing a latent period (LT), the y-axis being the fluorescence value (in a.u arbitrary units) and on x-axis being the time in minutes.

DETAILED DESCRIPTION

The applicant observed that, surprisingly, the co-polyamino acids according to the invention stabilize amylin, amylin receptor agonist or amylin analog compositions at neutral pH from 6 to 8. Indeed, compositions comprising amylin, an amylin receptor agonist or an amylin analog in combination with a co-polyamino acid according to the invention exhibit an increased stability over time, which is of major interest for pharmaceutical development.

The applicant also observed that the co-polyamino acids according to the invention further make it possible to obtain a composition comprising prandial insulin and amylin, an amylin receptor agonist or an amylin analog, said composition being clear and having an enhanced fibrillation stability.

A conventional method for measuring the stabilities of proteins or peptides consists of measuring fibril formation using Thioflavin T, also known as ThT. This method makes it possible to measure under temperature and stirring conditions enabling an acceleration of the phenomenon, the latent period prior to fibril formation by measuring the increase in fluorescence. The compositions according to the invention have a latent period prior to fibril formation markedly greater than that of amylin, an amylin receptor agonist or an amylin analog at the pH of interest.

The compositions according to the invention exhibit a satisfactory physical, and optionally chemical, stability at the desired pH.

In one embodiment, the invention relates to a composition in the form of an injectable aqueous solution, wherein the pH is comprised from 6.0 to 8.0, comprising at least:
a) amylin, an amylin receptor agonist or an amylin analog;
b) a co-polyamino acid bearing carboxylate charges carboxylates and at least one hydrophobic radical -Hy according to formula X, said co-polyamino acid being chosen among the co-polyamino acids according to formula I:

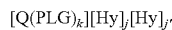   Formula I

Wherein:
j≥1; 0≤j'≤n'1 and j+j'≥1 and k≥2
said co-polyamino acid according to formula I bearing at least one hydrophobic radical -Hy, carboxylate charges and consisting of at least two chains of glutamic or aspartic units PLG bound together by an at least divalent linear or branched radical or spacer Q[-*]$_k$ consisting of an alkyl chain comprising one or a plurality of heteroatoms chosen in the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions.
said radical or spacer Q[-*]k being bound to at least two glutamic or aspartic unit chains PLG by an amide function and,
said amide bonds binding said radical or spacer Q[-*]k bound to said at least two chains of glutamic or aspartic units result from the reaction between an amine function and an acid function respectively borne either by the precursor Q' of the radical or spacer Q[-*]k or by a glutamic or aspartic unit,
said hydrophobic radical -Hy being bound either to a terminal "amino acid" unit and then j≥1, or to a carboxyl function borne by one of the chains of the glutamic or aspartic units PLG and then j'=n'1 and n'1 is the mean number of monomeric units bearing a hydrophobic radical -Hy.
In one embodiment, k is 2, 3, 4, 5 or 6.
In one embodiment, k=2.
In one embodiment, k=3.
In one embodiment, k=4.
In one embodiment, k=5.
In one embodiment, k=6.
In one embodiment, j is 1, 2, 3, 4, 5 or 6.
In one embodiment, j=1.
In one embodiment, j=2.
In one embodiment, j=3.
In one embodiment, j=4.
In one embodiment, j=5.
In one embodiment, j=6.

The co-polyamino acids bearing carboxylate charges and hydrophobic radicals according to formula X are soluble in distilled water at a pH from 6 to 8, at a temperature of 25° C. and at a concentration below 100 mg/ml.

The term "alkyl radical" denotes a linear or branched carbon chain, which does not comprise a heteroatom.

Said co-polyamino acid is a statistical co-polyamino acid in the chain of glutamic and/or aspartic units.

In the formulas, the * indicate the binding sites of the different elements represented.

In one embodiment, the invention also relates to the precursors of said hydrophobic radicals according to formula X.

The invention further relates to a method for preparing stable injectable compositions.

The term "soluble" denotes suitable for enabling the preparation of a clear, particle-free solution at a concentration below 100 mg/ml in distilled water at 25° C.

The term "solution" denotes a liquid composition free from visible particles, using the procedure as per the pharmacopeias EP 8.0, section 2.9.20, and US <790>.

The term "physically stable composition" denotes compositions meeting, after a certain storage time at a certain temperature, the visual inspection criteria described in the European, US and international pharmacopeia, namely compositions which are clear and free from visible particles, but also colorless.

The term "chemically stable composition" denotes compositions which, after storing for a certain time and at a certain temperature, exhibit a minimum recovery of the active ingredients and meet the specifications applicable to pharmaceutical products.

The term "injectable aqueous solution" denotes water-based solutions meeting EP and US pharmacopeia requirements, and which are sufficiently liquid to be injected.

The term "co-polyamino acid consisting of glutamic or aspartic units" denotes non-cyclic linear chains of glutamic acid or aspartic acid units bound together by peptide bonds, said chains having a C-terminal part, corresponding to the carboxylic acid of one extremity, and an N-terminal part, corresponding to the amine of the other extremity of the chain.

The term "alkyl radical" denotes a linear or branched carbon chain, which does not comprise a heteroatom.

The co-polyamino acid is a statistical or block co-polyamino acid.

Said co-polyamino acid is a statistical co-polyamino acid in the chain of glutamic and/or aspartic units.

The compositions in the form of an injectable aqueous solution according to the invention are clear solutions. The term "clear solution" denotes compositions meeting the criteria described in the US and European pharmacopeias in respect of injectable solutions. In the US pharmacopeia, solutions are defined in part <1151> referring to injection <1> (referring to <788> as per USP 35 and specified in <788> as per USP 35 and in <787>, <788> and <790> USP 38 (from Aug. 1, 2014), as per USP 38). In the European pharmacopeia, injectable solutions must comply with the criteria provided in sections 2.9.19 and 2.9.20.

In one embodiment, the composition according to the invention is characterized in that Hy comprises from 15 to 100 carbon atoms.

In one embodiment, the composition according to the invention is characterized in that Hy comprises from 30 to 70 carbon atoms.

In one embodiment, the composition according to the invention is characterized in that Hy comprises from 40 to 60 carbon atoms.

In one embodiment, the composition according to the invention is characterized in that Hy comprises from 20 to 30 carbon atoms In one embodiment, Hy comprises more than 15 carbon atoms.

In one embodiment, Hy comprises more than 30 carbon atoms.

In one embodiment, the composition is characterized in that the pH is comprised from 6.0 to 8.0.

In one embodiment, the composition is characterized in that the pH is comprised from 6.6 to 7.8.

In one embodiment, the composition is characterized in that the pH is comprised from 7.0 to 7.8.

In one embodiment, the composition is characterized in that the pH is comprised from 6.8 to 7.4.

In one embodiment, the radical or spacer $Q[-*]_k$ is represented by a radical according to formula II:

$$Q[-*]_k = ([Q']_q)[-*]_k \qquad \text{Formula II}$$

wherein $1 \leq q \leq 5$

The radicals Q' being identical or different and chosen in the group consisting of radicals of the following formulas III to VI', to form $Q[-*]_k$:
by a radical according to formula III:

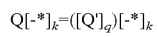

Formula III wherein $1 \leq t \leq 8$
by a radical according to formula IV:

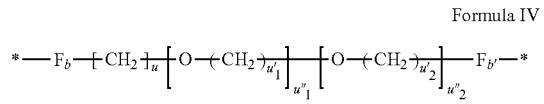

Formula IV wherein:
At least one of $u''_1$ or $u''_2$ is different from 0.
If $u''_1 \neq 0$ then $u'_1 \neq 0$ and if $u''_2 \neq 0$ then $u'_2 \neq 0$,
$u'_1$ and $u'_2$ are identical and different,
$2 \leq u \leq 4$,
$0 \leq u'_1 \leq 4$,
$0 \leq u''_1 \leq 4$,
$0 \leq u'_2 \leq 4$,
$0 \leq u''_2 \leq 4$;
by a radical according to formula V:

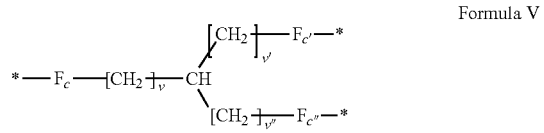

Formula V wherein:
v, v' and v" identical or different are integers $\geq 0$, and $v+v'+v'' \leq 15$,
by a radical according to formula VI:

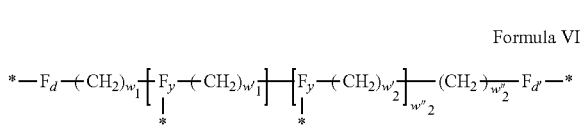

Formula VI wherein:
$w'_1$ is different from 0,
$0 \leq w''_2 \leq 1$,
$w_1 \leq 6$ and $w'_1 \leq 6$ and/or $w_2 \leq 6$ and $w'_2 \leq 6$
where $F_x = F_a, F_b, F_c, F_d, F_{a'}, F_{b'}, F_{c'}, F_{c''}$ et $F_{d'}$ identical or different representing functions —NH— or —CO— and $F_y$ representing a trivalent nitrogen atom —N=,
two radicals Q' being bound together by a covalent bond between a carbonyl function, $F_x$=—CO—, and an amine function $F_x$=—NH— or $F_y$=—N=, thus forming an amide function.

In one embodiment, said radical Q' is chosen among the radicals according to formula VI, wherein $w_2=0$ according to formula VI' as defined hereinafter:

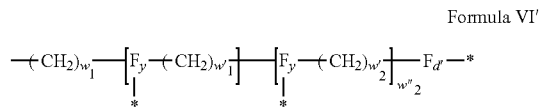

Formula VI' wherein:
$w'_1$ is different from 0,
$0 \leq w''_2 \leq 1$,
$w_1 \leq 6$ and $w'_1 \leq 6$ and/or $w'_2 \leq 6$ where $F_d$ and $F_{d'}$ identical or different representing functions —NH— or —CO— and $F_y$ representing a trivalent nitrogen atom —N=, two radicals Q' being bound together by a covalent bond between a carbonyl function, $F_x$=—CO—, and an amine function $F_x$=—NH— or $F_y$=—N=, thus forming an amide bond, where in each of the radicals represented above, $F_x=F_a$, $F_b$, $F_c$, $F_d$, $F_{a'}$, $F_{b'}$, $F_{c'}$, $F_{c''}$ and $F_{d'}$ identical or different representing functions —NH— or —CO— and $F_y$ representing a trivalent nitrogen atom —N=, two radicals Q' being bound together by a covalent bond between a carbonyl function, $F_x$=—CO—, and an amine function $F_x$=—NH— or $F_y$=—N=, thus forming an amide bond. When a function $F_x=F_a$, $F_b$, $F_c$, $F_d$, $F_{a'}$, $F_{b'}$, $F_{c'}$, $F_{c''}$ and $F_{d'}$ is not used in a bond between two Q', this function is then free and salified In one embodiment, if $F_a$ and $F_{a'}$ are —NH—, then $t \geq 2$.

In one embodiment, if $F_a$ and $F_{a'}$ are —CO—, then $t \geq 1$.

In one embodiment, if $F_a$ and $F_{a'}$ are —CO— and —NH—, then $t \geq 1$.

In one embodiment, if $F_b$ and $F_{b'}$ are —NH—, then u and $u'_1 \geq 2$ and/or $u'_2 \geq 2$.

In one embodiment, if $F_c$, $F_{c'}$, and $F_{c''}$ are —NH— then at least two of v, v' and v" are different to 0.

In one embodiment, if $F_c$, $F_{c'}$ and $F_{c''}$ are 2 —NH— and 1 —CO— then at least one of the indices of the —(CH$_2$)— bearing a nitrogen is different to 0.

In one embodiment, if $F_c$, $F_{c'}$, and $F_{c''}$ are 1 —NH— and 2 —CO— then no conditions.

In one embodiment, if $F_c$, $F_{c'}$, and $F_{c''}$ are —CO— then at least one of v, v' and v" is different to 0.

In one embodiment, if $F_d$ and $F_{d'}$ are —NH—, $w_1$ and $w'_1 \geq 2$ and/or $w_2$ and $w'_2 \geq 2$.

In one embodiment, if $F_d$ and $F_{d'}$ are —CO—, $w_1$ and $w'_1 \geq 1$ and/or $w_2$ and $w'_2 \geq 1$.

In one embodiment, if $F_d$ and $F_{d'}$ are —CO— and —NH—, $w_1$ and $w'_1 \geq 1$ and/or $w_2$ and $w'_2 \geq 1$.

The at least two chains of glutamic or aspartic units PLG being bound to Q[-*]$_k$ by a function $F_x$ or $F_y$ by a covalent bond to form an amide bond with a function —NH— or —CO— of the PLG.

In one embodiment, $1 \leq q \leq 5$.

In one embodiment, $v+v'+v'' \leq 15$.

In one embodiment, at least one of the Q' is a radical according to formula III,

   Formula III wherein the precursor is a diamine.

In one embodiment, the precursor of the radical according to formula III is a diamine chosen in the group consisting of ethylenediamine, butylenediamine, hexylenediamine, 1,3-diaminopropane and 1,5-diaminopentane.

In one embodiment, t=2 and the precursor of the radical according to formula III is ethylenediamine.

In one embodiment, t=4 and the precursor of the radical according to formula III is butylenediamine.

In one embodiment, t=6 and the precursor of the radical according to formula III is hexylenediamine.

In one embodiment, t=3 and the precursor of the radical according to formula III is 1,3-diaminopropane.

In one embodiment, t=5 and the precursor of the radical according to formula III is 1,5-diaminopentane.

In one embodiment, the precursor of the radical according to formula III is an amino acid.

In one embodiment, the precursor of the radical according to formula III is an amino acid chosen in the group consisting of aminobutanoic acid, aminohexanoic acid and beta-alanine.

In one embodiment, t=2 and the precursor of the radical according to formula III is beta-alanine.

In one embodiment, t=6 and the precursor of the radical according to formula III is aminohexanoic acid.

In one embodiment, t=4 and the precursor of the radical according to formula III is aminobutanoic acid In one embodiment, the precursor of the radical according to formula III is a diacid.

In one embodiment, the precursor of the radical according to formula III is a diacid chosen in the group consisting of succinic acid, glutaric acid and adipic acid.

In one embodiment, t=2 and the precursor of the radical according to formula III is succinic acid.

In one embodiment, t=3 and the precursor of the radical according to formula III is glutaric acid.

In one embodiment, t=4 and the precursor of the radical according to formula III is adipic acid.

In one embodiment, at least one of the Q' is a radical according to formula IV.

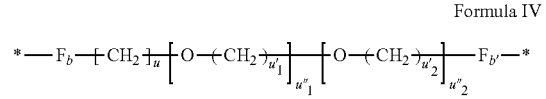   Formula IV wherein the precursor is a diamine.

In one embodiment, the precursor of the radical according to formula IV is a diamine chosen in the group consisting of diethyleneglycol diamine, triethyleneglycol diamine, 4,9-dioxa-1,12-dodecanediamine and 1-amino-4,7,10-trioxa-13-tridecanamine.

In one embodiment, $u=u'_1=2$, $u''_1=1$, $u''_2=0$ and the precursor of the radical according to formula IV is diethyleneglycol diamine.

In one embodiment, $u=u'_1=u'_2=2$, $u''_1=u''_2=1$ and the precursor of the radical according to formula IV is triethyleneglycol diamine.

In one embodiment, $u=u'_2=3$, $u'_1=4$, $u''_1=u''_2=1$ and the precursor of the radical according to formula IV is 4,9-dioxa-1,12-dodecanediamine.

In one embodiment, $u=u'_2=3$, $u'_1=u''_1=2$, $u''_2=1$ and the precursor of the radical according to formula IV is 4,7,10-trioxa-1,13-tridecanediamine.

In one embodiment, at least one of the Q' is a radical according to formula V,

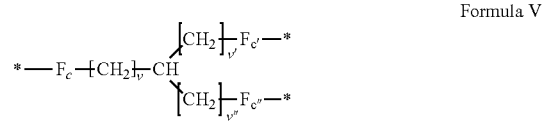   Formula V wherein the precursor is chosen in the group consisting of amino acids.

In one embodiment, the precursor of the radical according to formula V is an amino acid chosen in the group consisting of lysine, ornithine, 2,3-diaminopropionic acid.

In one embodiment, v=4, v'=v"=0 and the precursor of the radical according to formula V is lysine.

In one embodiment, v=3, v'=v"=0 and the precursor of the radical according to formula V is ornithine.

In one embodiment, v=2, v'=v"=0 and the precursor of the radical according to formula V is 2,3-diaminopropionic acid.

In one embodiment, at least one of the Q' is a radical according to formula V, $$*-F_c-(CH_2)_v-CH\begin{matrix}(CH_2)_{v'}-F_{c'}-*\\(CH_2)_{v''}-F_{c''}-*\end{matrix}$$

Formula V wherein the precursor is chosen in the group consisting of triacids.

In one embodiment, the precursor of the radical according to formula V is a triacid chosen in the group consisting of tricarballylic acid.

In one embodiment, v=0, v'=v"=1 and the precursor of the radical according to formula V is tricarballylic acid.

In one embodiment, at least one of the Q' is a radical according to formula V, $$*-F_c-(CH_2)_v-CH\begin{matrix}(CH_2)_{v'}-F_{c'}-*\\(CH_2)_{v''}-F_{c''}-*\end{matrix}$$

Formula V wherein the precursor is chosen in the group consisting of triamines.

In one embodiment, the precursor of the radical according to formula V is a triamine chosen in the group consisting of (2-(aminomethyl)propane-1,3-diamine).

In one embodiment, v=v'=v"=1 and the precursor of the radical according to formula V is (2-(aminomethyl)propane-1,3-diamine).

In one embodiment, at least one of the Q' is a radical according to formula VI, $$*-F_d-(CH_2)_{w_1}-[F_y-(CH_2)_{w'_1}]-[F_y-(CH_2)_{w_2}]-(CH_2)_{w'_2}-F_{d'}-*$$

Formula VI wherein the precursor is a triamine.

In one embodiment, w"$_2$=0 and the precursor of the radical according to formula VI is a triamine chosen in the group consisting of spermidine, norspermidine, and diethylenetriamine and bis(hexamethylene)triamine.

In one embodiment, w"$_2$=0 and the precursor of the radical according to formula VI is spermidine.

In one embodiment, w"$_2$=0 and the precursor of the radical according to formula VI is norspermidine.

In one embodiment, w"$_2$=0 and the precursor of the radical according to formula VI is diethylenetriamine.

In one embodiment, w"$_2$=0 and the precursor of the radical according to formula VI is bis(hexamethylene)triamine.

In one embodiment, at least one of the Q' is a radical according to formula VI, $$*-F_d-(CH_2)_{w_1}-[F_y-(CH_2)_{w'_1}]-[F_y-(CH_2)_{w_2}]-(CH_2)_{w'_2}-F_{d'}-*$$

Formula VI wherein the precursor is a tetramine.

In one embodiment, w"$_2$=1 and the precursor of the radical according to formula VI is a tetramine.

In one embodiment, w"$_2$=1 and the precursor of the radical according to formula VI is a tetramine chosen in the group consisting of spermine and triethylenetetramine.

In one embodiment, w"$_2$=1 and the precursor of the radical according to formula VI is spermine.

In one embodiment, w"$_2$=1 and the precursor of the radical according to formula VI is triethylenetetramine.

In one embodiment, the precursor of the radical or spacer Q[-*]$_k$ has 4 reactive functions, chosen among the group of amine functions and carboxylic acid functions.

In one embodiment, the precursor of the radical or spacer Q[-*]$_k$ has 4 reactive functions and the precursor of the radical or spacer Q[-*]$_k$ is 1,2,3,4-butanetetraoic acid.

In one embodiment, at least one of the Q' is a radical according to formula VI', $$-(CH_2)_{w_1}-[F_y-(CH_2)_{w'_1}]-[F_y-(CH_2)_{w_2}]-F_{d'}-*$$

Formula VI' wherein the precursor is a triamine.

In one embodiment, w"$_2$=0 and the precursor of the radical according to formula VI' is a triamine chosen in the group consisting of spermidine, norspermidine, and diethylenetriamine and bis(hexamethylene)triamine.

In one embodiment, w"$_2$=0 and the precursor of the radical according to formula VI' is spermidine.

In one embodiment, w"$_2$=0 and the precursor of the radical according to formula VI' is norspermidine.

In one embodiment, w"$_2$=0 and the precursor of the radical according to formula VI' is diethylenetriamine.

In one embodiment, w"$_2$=0 and the precursor of the radical according to formula VI' is bis(hexamethylene)triamine.

In one embodiment, at least one of the Q' is a radical according to formula VI', $$-(CH_2)_{w_1}-[F_y-(CH_2)_{w'_1}]-[F_y-(CH_2)_{w_2}]-F_{d'}-*$$

Formula VI' wherein the precursor is a tetramine.

In one embodiment, w"$_2$=1 and the precursor of the radical according to formula VI' is a tetramine.

In one embodiment, w"$_2$=1 and the precursor of the radical according to formula VI' is a tetramine chosen in the group consisting of spermine and triethylenetetramine.

In one embodiment, $w''_2=1$ and the precursor of the radical according to formula VI' is spermine.

In one embodiment, $w''_2=1$ and the precursor of the radical according to formula VI' is triethylenetetramine.

In one embodiment, all the $F_x$ are bound to the PLG or to other $F_x$ or $F_y$.

In one embodiment, one or plurality of $F_x$ are free, i.e. are not bound to the PLG, or to another $F_x$, or to an $F_y$.

In one embodiment, one $F_x$ is free, i.e. is not bound to the PLG, or to another $F_x$, or to an $F_y$.

In one embodiment, the —CO— type $F_x$(s) is free, it is in carboxylic acid salt form.

In one embodiment, the free —CO— type $F_x$ is borne by a radical Q' according to Formula V.

In one embodiment, the —NH— type $F_x$(s) is free, it is in amine or ammonium form.

In one embodiment, the PLG are bound to $F_x$ where $F_x$=—NH— or to $F_y$ by at least one carbonyl function of the PLG.

In one embodiment, the PLG are bound to $F_x$ where $F_x$=—NH— or to $F_y$ by at least one carbonyl function which is not in the C-terminal position of the PLG.

In one embodiment, the PLG are bound to $F_x$ where $F_x$=—NH— or to $F_y$ by the carbonyl function in the C-terminal function of the PLG.

In one embodiment, the PLG are bound to $F_x$ where $F_x$=—NH— by the carbonyl function in the C-terminal function of the PLG.

In one embodiment, the PLG are bound to $F_x$ where $F_x$=$F_y$ by the carbonyl function in the C-terminal function of the PLG.

In one embodiment, the PLG are bound to $F_x$, where $F_x$=—CO— by the nitrogen atom in the N-terminal function of the PLG.

In one embodiment, the composition according to the invention is characterized in that the co-polyamino acid bearing carboxylate charges and at least one hydrophobic radical -Hy is chosen among the co-polyamino acids according to formula XXXa hereinafter:

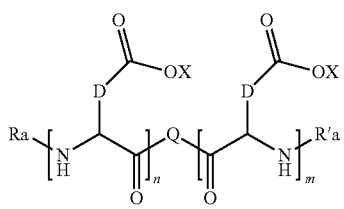

Formula XXXa wherein,
D and X are as defined above,
Ra and R'a, identical or different, are either a hydrophobic radical -Hy, or a radical chosen in the group consisting of an H, a $C_2$ to $C_{10}$ linear acyl group, a $C_3$ to $C_{10}$ branched acyl group, a benzyl, a terminal "amino acid" unit and a pyroglutamate,
at least one of Ra and R'a being a hydrophobic radical -Hy,
Q and -Hy are as defined above.
n+m is as defined above.

In one embodiment, the composition according to the invention is characterized in that the co-polyamino acid bearing carboxylate charges and at least one hydrophobic radical -Hy is chosen among the co-polyamino acids according to formula XXXa wherein $R_a$ and $R'_a$, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein $R_a$ and $R'_a$, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa wherein $R_a$ is a hydrophobic radical -Hy and $R'_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein $R'_a$ is a hydrophobic radical -Hy, and $R_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' hereinafter:

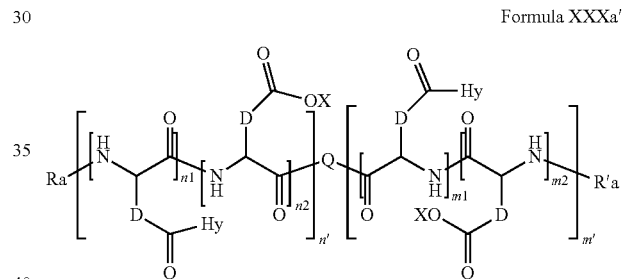

Formula XXXa'

Wherein:
D, X, Ra and R'a are as defined above,
Q and Hy are as defined above,
$n_1+m_1$ represents the number of glutamic units or aspartic units of the PLG chains of the co-polyamino acid bearing a radical -Hy,
$n_2+m_2$ represents the number of glutamic units or aspartic units of the PLG chains of the co-polyamino acid not bearing a radical -Hy,
$n_1+n_2=n'$ and $m_1+m_2=m'$
n'+m' represents the degree of polymerization DP of the co-polyamino acid, namely the mean number of monomeric units per co-polyamino acid chain and $5 \leq n'+m' \leq 250$.

In one embodiment, the composition according to the invention is characterized in that the co-polyamino acid bearing carboxylate charges and at least one hydrophobic radical -Hy is chosen among the co-polyamino acids according to formula XXXa' wherein Ra and R'a, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra and R' a, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra is a hydrophobic radical -Hy and R'a is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein R'a is a hydrophobic radical -Hy, and Ra is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb hereinafter:

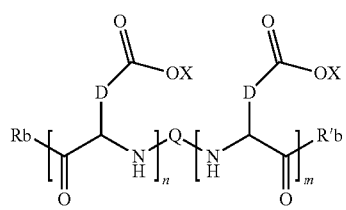

Formula XXXb wherein,
D and X are as defined above,
Rb and R'b, identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy,
Q and Hy are as defined above.
n+m is as defined above.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein R'b is a hydrophobic radical -Hy, and Rb is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' hereinafter:

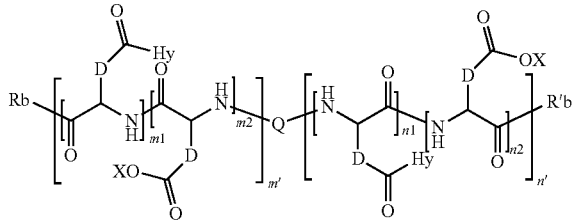

Formula XXXb' wherein:
D and X are as defined above,
Q and Hy are as defined above.
Rb and R'b, identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy,
n1+m1 represents the number of glutamic units or aspartic units of the PLG chains of the co-polyamino acid bearing a radical -Hy,
n2+m2 represents the number of glutamic units or aspartic units of the PLG chains of the co-polyamino acid not bearing a radical -Hy,
n1+n2=n' and m1+m2=m',
n'+m' represents the degree of polymerization DP of the co-polyamino acid, namely the mean number of monomeric units per co-polyamino acid chain and 5≤n'+m'≤250.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein R'b is a hydrophobic radical -Hy, and Rb is not a hydrophobic radical -Hy.

When the co-polyamino acid comprises one or a plurality of aspartic unit(s), the latter may to be subject to structural rearrangements.

In one embodiment, the composition according to the invention is characterized in that when the co-polyamino acids comprises aspartate units, then the co-polyamino acids may further comprise monomeric units according to formula XXXX and/or XXXX':

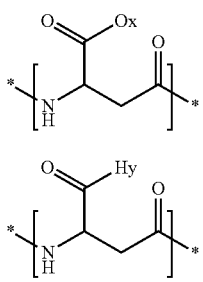

Formula XXXX

Formula XXXX'

In one embodiment, the composition according to the invention is characterized in that the co-polyamino acid bearing carboxylate charges and hydrophobic radicals is chosen among the co-polyamino acids according to formulas XXXa, XXXa', XXXb or XXXb' wherein the co-polyamino acid is chosen among the co-polyamino acids wherein the group D is a group —CH2— (aspartic unit).

In one embodiment, the composition according to the invention is characterized in that the co-polyamino acid bearing carboxylate charges and hydrophobic radicals is chosen among the co-polyamino acids according to formulas XXXa, XXXa', XXXb or XXXb' wherein the co-polyamino acid is chosen among the co-polyamino acids wherein the group D is a group —CH$_2$—CH$_2$— (glutamic unit).

In one embodiment, the composition according to the invention is characterized in that n+m is comprised from 10 to 250.

In one embodiment, the composition according to the invention is characterized in that n+m is comprised from 10 to 200.

In one embodiment, the composition according to the invention is characterized in that n+m is comprised from 15 to 150.

In one embodiment, the composition according to the invention is characterized in that n+m is comprised from 15 to 100.

In one embodiment, the composition according to the invention is characterized in that n+m is comprised from 15 to 80.

In one embodiment, the composition according to the invention is characterized in that n+m is comprised from 15 to 65.

In one embodiment, the composition according to the invention is characterized in that n+m is comprised from 20 to 60.

In one embodiment, the composition according to the invention is characterized in that n+m is comprised from 20 to 50.

In one embodiment, the composition according to the invention is characterized in that n+m is comprised from 20 to 40.

The invention also relates to said co-polyamino acids bearing carboxylate charges and hydrophobic radicals according to formula X and the precursors of said hydrophobic radicals.

In one embodiment, said at least one hydrophobic radical -Hy is chosen among the radicals according to formula X:

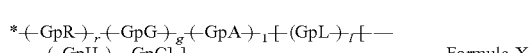

Formula X wherein

GpR is chosen among the radicals according to formulas VII, VII' or VII":

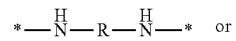 or

Formula VII

 or

Formula VII'

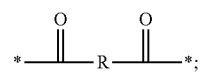

Formula VII"

GpG and GpH identical or different are chosen among the radicals according to formulas XI or XI':

Formula XI

Formula XI'

GpA is chosen among the radicals according to formula VIII

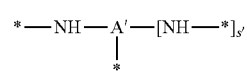

Formula VIII wherein A' is chosen among the radicals according to VIII', VIII" or VIII'"

Formula VIII'

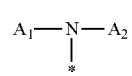

Formula VIII"

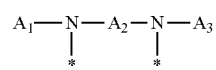

Formula VIII'"

-GpL is chosen among the radicals according to formula XII

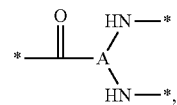

Formula XII

GpC is a radical according to formula IX:

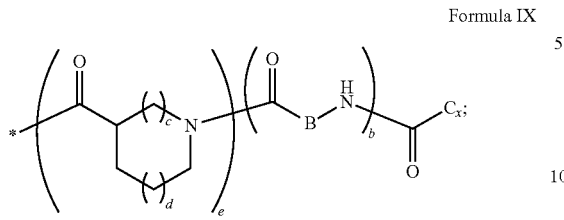

Formula IX the * indicate the binding sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
l' is an integer equal to 1 or to 2;
r is an integer equal to 0, 1 or to 2, and
s' is an integer equal to 0 or 1;
A, $A_1$, $A_2$ and $A_3$ identical or different are linear or branched alkyl radicals comprising from 1 to 8 carbon atoms, and optionally substituted by a radical from a saturated, unsaturated or aromatic ring;
B is a radical chosen in the group consisting of a non-substituted ether or polyether radical comprising from 4 to 14 carbon atoms and from 1 to 5 oxygen atoms or a linear or branched alkyl radical, optionally comprising an aromatic nucleus, comprising from 1 to 9 carbon atoms;
$C_x$ is a radical chosen in the group consisting of a linear or branched monovalent alkyl radical, optionally comprising a cyclic part, wherein x indicates the number of carbon atoms and $6 \leq x \leq 25$:
  When the hydrophobic radical -Hy bears 1 -GpC, then $9 \leq x \leq 25$,
  When the hydrophobic radical -Hy bears 2 -GpC, then $9 \leq x \leq 15$,
  When the hydrophobic radical -Hy bears 3 -GpC, then $7 \leq x \leq 13$,
  When the hydrophobic radical -Hy bears 4 -GpC, then $7 \leq x \leq 11$,
  When the hydrophobic radical -Hy bears at least 5 -GpC, then $6 \leq x \leq 11$;
G is a linear or branched divalent alkyl radical of 1 to 8 carbon atoms, said alkyl radical bearing one or a plurality of free carboxylic acid function(s),
R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms the hydrophobic radical(s) -Hy according to formula X being bound to the PLG:
  via a covalent bond between a carbonyl of the hydrophobic radical -Hy and a nitrogen atom borne by the PLG thus forming an amide function obtained from the reaction of an amine function borne by the PLG and an acid function borne by the precursor Hy' of the hydrophobic radical -Hy and/or
  via a covalent bond between a nitrogen atom of the hydrophobic radical -Hy and a carbonyl borne by the PLG thus forming an amide function obtained from the reaction of an amine function of the precursor Hy' of the hydrophobic radical -Hy and an acid function borne by the PLG;
the ratio M between the number of hydrophobic radicals and the number of glutamic or aspartic units being comprised from $0 < M \leq 0.5$;
when a plurality of hydrophobic radicals are borne by a co-polyamino acid then they are identical or different;
the degree of polymerization DP in glutamic or aspartic units for the PLG chains is comprised from 5 to 250;
the free acid functions being in the form of alkali cation salt chosen in the group consisting of $Na^+$ and $K^+$.

In one embodiment, when a'=1, x is comprised from 11 to 25 ($11 \leq x \leq 25$). In particular, when x is comprised from 15 to 16 (x=15 or 16) then r=1 and R is an ether or polyether radical and when x is greater than 17 ($x \geq 17$) then r=1 and R is an ether or polyether radical.

In one embodiment, when a'=2, x is comprised from 9 to 15 ($9 \leq x \leq 15$).

In one embodiment, when r=2 then the group GpR bound to the PLG is chosen among the GpR according to formula VII.

In one embodiment, when r=2 then the group GpR bound to the PLG is chosen among the GpR according to formula VII and the second GpR is chosen among the GpR according to formula VII".

In one embodiment, when r=2 then the group GpR bound to the PLG is chosen among the GpR according to formula VII".

In one embodiment, when r=2 then the group GpR bound to the PLG is chosen among the GpR according to formula VII" and the second GpR is chosen among the GpR according to formula VII.

In one embodiment, said at least one hydrophobic radical -Hy is chosen among the radicals according to formula X wherein r=1 according to formula Xc, as defined hereinafter:

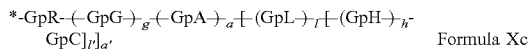

Formula Xc wherein GpR, GpG, GpA, GpL, GpH, GpC, R, a, a', g, h, l, a' and l' are as defined above.

In one embodiment, said at least one hydrophobic radical -Hy is chosen among the radicals according to formula X wherein r=1 according to formula Xc, as defined hereinafter:

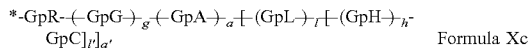

Formula Xc wherein GpR is a radical according to formula VII.

Formula VII wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

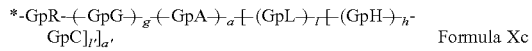 Formula Xc wherein GpR is a radical according to formula VII'.

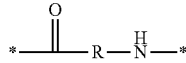 Formula VII' wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

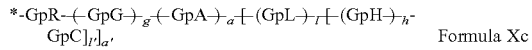 Formula Xc wherein GpR is a radical according to formula VII".

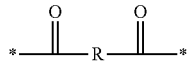 Formula VII"

wherein GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

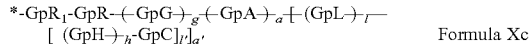 Formula Xc' wherein $GpR_1$ is a radical according to formula VII.

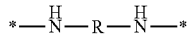 Formula VII wherein GpR, GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

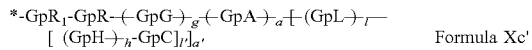 Formula Xc' wherein $GpR_1$ is a radical according to formula VII".

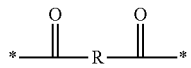 Formula VII"

wherein GpR, GpG, GpA, GpL, GpH, GpC, R, a, a', g, h, l and l' are as defined above.

In one embodiment, said at least one hydrophobic radical -Hy is chosen among the radicals according to formula Xq as defined hereinafter:

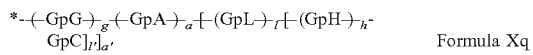 Formula Xq wherein GpG, GpA, GpL, GpH, GpC, g, a, a', l, h and l' are as defined above.

In one embodiment, said at least one hydrophobic radical -Hy is chosen among the radicals according to formula Xr as defined hereinafter:

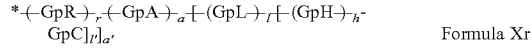 Formula Xr wherein GpR, GpA, GpL, GpH, GpC, r, a, a', l, h and l' are as defined above.

In one embodiment, the composition according to the invention is characterized in that said hydrophobic radicals are chosen among the hydrophobic radicals according to formula X wherein h=0 and g=0, represented by the formula Xj hereinafter:

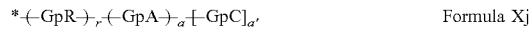 Formula Xj wherein GpR, GpA, GpC, r, a' and a are as defined above.

In one embodiment, the composition according to the invention is characterized in that said hydrophobic radicals are chosen among the hydrophobic radicals according to formula X wherein h=0 and g=0 and a'=1, represented by the formula Xk hereinafter:

 Formula Xk wherein GpR, GpA, GpC, r and a are as defined above.

In one embodiment, the composition according to the invention is characterized in that said hydrophobic radicals are chosen among the hydrophobic radicals according to formula X wherein h=0 and g=0 and a=1 and a'=2, represented by the formula Xl hereinafter:

 Formula Xj wherein GpR, GpA, GpC and r are as defined above.

In one embodiment, the composition according to the invention is characterized in that said hydrophobic radicals are chosen among the hydrophobic radicals according to formula X wherein a=1 and a'=1 and g=l=0, represented by the formula Xn hereinafter:

 Formula Xn wherein GpR, GpA, GpH, GpC, r and h are as defined above.

In one embodiment, the composition according to the invention is characterized in that said hydrophobic radicals are chosen among the hydrophobic radicals according to formula X wherein a=1 and a'=2 and g=l=0, represented by the formula Xp hereinafter:

 Formula Xp wherein GpR, GpA, GpH, GpC, r and h are as defined above.

In one embodiment, the composition according to the invention is characterized in that said hydrophobic radicals are chosen among the hydrophobic radicals according to formula X wherein a=1, g, h and l=0 and a'=3, represented by the formula Xm hereinafter:

 Formula Xm wherein GpA is a radical chosen among the radicals according to formula VIIId and GpR, GpC, r are as defined above.

In one embodiment, the composition according to the invention is characterized in that said hydrophobic radicals are chosen among the hydrophobic radicals according to formula X wherein a, g, h and l=0, represented by the formula Xm' hereinafter:

 Formula Xm' wherein GpR, GpC, r are as defined above.

In one embodiment, said at least one hydrophobic radical -Hy is chosen among the radicals according to formula X wherein r, g, a, l, h are equal to 0, according to formula Xo as defined hereinafter:

*-GpC                                    Formula Xo wherein GpC is as defined above.

In one embodiment, said at least one hydrophobic radical -Hy is chosen among the radicals according to formula X wherein r, g, a, l, h are equal to 0, according to formula Xo as defined hereinafter:

*-GpC                                    Formula Xo wherein GpC is a radical according to formula IX wherein e=0, b=0 and GpC is a radical according to formula IXc

IXc

In one embodiment, said at least one hydrophobic radical -Hy is chosen among the radicals according to formula Xs as defined hereinafter:

*-[-(GpR-)$_r$-(-GpG-)$_g$-(GpL-)$_l$-[-(GpH-)$_h$-GpC]$_{l'}$     Formula Xn wherein GpR, GpG, GpL, GpH, GpC, r, g, l, h and l' are as defined above.

In one embodiment, said at least one hydrophobic radical -Hy is chosen among the radicals according to formula X wherein a=1 and a'=1 according to formula Xa as defined hereinafter:

*-[-(GpR-)$_r$-(-GpG-)$_g$-GpA-(GpL-)$_l$-[-(GpH-)$_h$-GpC]$_{l'}$     Formula Xa wherein GpA, GpR, GpG, GpL, GpH, GpC, r, g, h and l' are as defined above.

In one embodiment, said at least one hydrophobic radical -Hy is chosen among the radicals according to formula X wherein a=1 and a'=1 according to formula Xa as defined hereinafter:

*-[-(GpR-)$_r$-(-GpG-)$_g$-GpA-(GpL-)$_l$-[-(GpH-)$_h$-GpC]$_{l'}$     Formula Xa wherein GpA is a radical according to formula VIII and A' is chosen among the radicals according to formula VIII' where s'=0 and GpA is a radical according to formula VIIIb

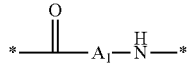

Formula VIIIb wherein GpR, GpG, GpL, GpH, GpC, r, g, h, l and l' are as defined above.

In one embodiment, said at least one hydrophobic radical -Hy is chosen among the radicals according to formula X wherein a=1 and a'=2 according to formula Xb as defined hereinafter:

*-[-(GpR-)$_r$-(-GpG-)$_g$-GpA-[-(GpL-)$_l$-[-(GpH-)$_h$-GpC]$_{l'}$]$_2$     Formula Xb wherein GpA, GpR, GpG, GpL, GpH, GpC, r, g, h and l' are as defined above.

In one embodiment, said at least one hydrophobic radical -Hy is chosen among the radicals according to formula X wherein a=1 and a'=2 according to formula Xb as defined hereinafter:

*-[-(GpR-)$_r$-(-GpG-)$_g$-GpA-[-(GpL-)$_l$-[-(GpH-)$_h$-GpC]$_{l'}$]$_2$     Formula Xb wherein GpA is a radical according to formula VIII and A' is chosen among the radicals according to formula VIII' where s'=1 and GpA is a radical according to formula VIIIa where a'=2

Formula VIIIa wherein GpR, GpG, GpL, GpH, GpC, $A_1$, r, g, h, l and l' are as defined above.

In one embodiment, said at least one hydrophobic radical -Hy is chosen among the radicals according to formula X wherein a=1 and a'=2 as defined hereinafter:

*-[-(GpR-)$_r$-(-GpG-)$_g$-GpA-[-(GpL-)$_l$-[-(GpH-)$_h$-GpC]$_{l'}$]$_{a'}$     Formula Xb wherein GpA is a radical according to formula VIII and A is chosen among the radicals according to formula VIII" where s'=1 and GpA is a radical according to formula VIIIc

Formula VIIIc wherein GpR, GpG, GpL, GpH, GpC, $A_1$, $A_2$, r, g, h, l and l' are as defined above.

In one embodiment, said at least one hydrophobic radical -Hy is chosen among the radicals according to formula X wherein a=1 and a'=3 as defined hereinafter:

*-[-(GpR-)$_r$-(-GpG-)$_g$-GpA-[-(GpL-)$_l$-[-(GpH-)$_h$-GpC]$_{l'}$]$_3$     Formula Xb wherein GpA is a radical according to formula VIII and A is chosen among the radicals according to formula VIII''' where s'=1 and GpA is a radical according to formula VIIId

Formula VIIId wherein GpR, GpG, GpL, GpH, GpC, $A_1$, $A_2$, $A_3$, r, g, h, l and l' are as defined above.

In one embodiment said at least one hydrophobic radical -Hy is chosen among the radicals according to formula X as defined above wherein l=0 according to formula Xd as defined hereinafter:

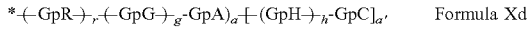
   *-(-GpR-)$_r$-(-GpG-)$_g$-GpA)$_a$-[-(GpH-)$_h$-GpC]$_{a'}$  Formula Xd wherein GpR, GpG, GpA, GpH, GpC, r, g, a, h and a' are as defined above.

In one embodiment, said at least one hydrophobic radical -Hy is chosen among the radicals according to formula X wherein
l=0,
according to formula Xd as defined hereinafter

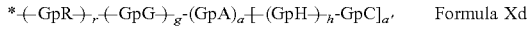
   *-(-GpR-)$_r$-(-GpG-)$_g$-(GpA)$_a$-[-(GpH-)$_h$-GpC]$_{a'}$  Formula Xd wherein
GpA is chosen among the radicals according to formula VIII wherein s'=1 represented by the formula VIIIa or according to formula VIII wherein s'=0 represented by the formula VIIIb:

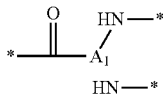

Formula VIIIa

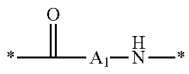

Formula VIIIb b, c, d, e, g, h, r, and s' are as defined above;
GpR, GpH, GpG, GpC, A$_1$, B, C$_x$, G, H, R are as defined above.

In one embodiment said at least one hydrophobic radical -Hy is chosen among the radicals according to formula X as defined above wherein l=0 according to formula Xd as defined hereinafter:

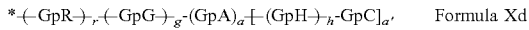
   *-(-GpR-)$_r$-(-GpG-)$_g$-(GpA)$_a$-[-(GpH-)$_h$-GpC]$_{a'}$  Formula Xd wherein
GpA is chosen among the radicals according to formula VIII wherein s'=1 represented by the formula VIIIc or the formula VIIId:

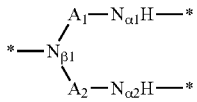

Formula VIIIc

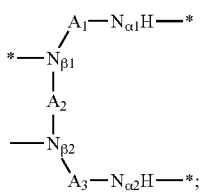

Formula VIIId wherein GpR, GpG, GpH, GpC, A$_1$, A$_2$, A$_3$, r, g, a, h and a' are as defined above.

In one embodiment, the composition according to the invention is characterized in that said hydrophobic radicals are chosen among the hydrophobic radicals according to formula X wherein GpA is a radical according to formula VIIIb, a'=1 and l=0 represented by the formula Xe hereinafter:

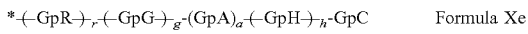
   *-(-GpR-)$_r$-(-GpG-)$_g$-(GpA)$_a$-(-GpH-)$_h$-GpC  Formula Xe wherein GpR, GpG, GpA, GpH, GpC, r, g, h, and a are as defined above.

In one embodiment, the composition according to the invention is characterized in that said hydrophobic radicals are chosen among the hydrophobic radicals according to formula X wherein a'=2 and a=1 and l=0 represented by the formula Xf hereinafter:

   *-(-GpR-)$_r$-(-GpG-)$_g$GpA-[-(GpH-)$_h$GpC]$_2$  Formula Xf wherein GpR, GpG, GpA, GpH, GpC, r, g and h are as defined above.

In one embodiment, the composition according to the invention is characterized in that said hydrophobic radicals are chosen among the hydrophobic radicals according to formula X wherein h=0, l=0 and l'=1 represented by the formula Xg hereinafter:

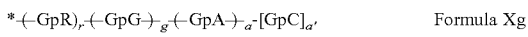
   *-(-GpR)$_r$-(-GpG-)$_g$-(-GpA-)$_a$-[GpC]$_{a'}$  Formula Xg wherein GpR, GpG, GpA, GpC, r, g, a and a' are as defined above.

In one embodiment, the composition according to the invention is characterized in that said hydrophobic radicals are chosen among the hydrophobic radicals according to formula X wherein h=0, a'=1 represented by the formula Xh hereinafter:

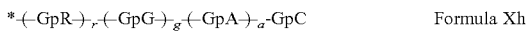
   *-(-GpR-)$_r$-(-GpG-)$_g$-(-GpA-)$_a$-GpC  Formula Xh wherein GpR, GpG, GpA, GpC, r, a and g are as defined above.

In one embodiment, the composition according to the invention is characterized in that said hydrophobic radicals are chosen among the hydrophobic radicals according to formula X wherein h=0, a'=2 and a=1 represented by the formula Xi hereinafter:

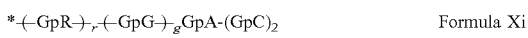
   *-(-GpR-)$_r$-(-GpG-)$_g$GpA-(GpC)$_2$  Formula Xi wherein GpR, GpG, GpA, GpC, r and g are as defined above.

In one embodiment said at least one hydrophobic radical -Hy is chosen among the radicals according to formula X as defined above wherein h=0 according to formula Xt as defined hereinafter:

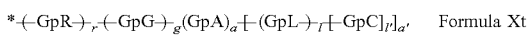
   *-(-GpR-)$_r$-(-GpG-)$_g$(GpA)$_a$-[-(GpL-)$_l$-[-GpC]$_{l'}$]$_{a'}$  Formula Xt wherein GpR, GpG, GpA, GpL, GpC, r, g, a, l, l' and a' are as defined above.

In one embodiment said at least one hydrophobic radical -Hy is chosen among the radicals according to formula X as defined above wherein h and g=0 according to formula Xt' as defined hereinafter:

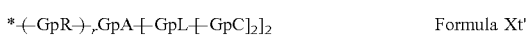
   *-(-GpR-)$_r$-GpA-[-GpL-[-GpC]$_2$]$_2$  Formula Xt' wherein GpR, GpA, GpL, GpC and r are as defined above.

In one embodiment, the composition according to the invention is characterized in that said hydrophobic radicals are chosen among the hydrophobic radicals according to formula X wherein, l'=2 and a'=2 represented by the formula Xu hereinafter:

   *-(-GpR-)$_r$-(-GpA)-[-(GpL-)-[-GpC]$_2$]$_2$  Formula Xu wherein GpR, GpA, GpL and GpC are as defined above.

In one embodiment, said at least one hydrophobic radical -Hy is chosen among the radicals according to formulas X, Xa to Xu:

wherein at least one of g and/or h is greater than or equal to 1 wherein GpC is a radical according to formula IX wherein e=0 and GpC is a radical according to formula IXa.

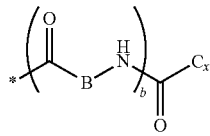

Formula IXa wherein B, b and $C_x$ are as defined above.

In one embodiment, said at least one hydrophobic radical -Hy is chosen among the radicals according to formulas X, Xa to Xu wherein GpC is a radical according to formula IX wherein e=0 and GpC is a radical according to formula IXa,

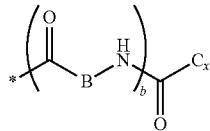

Formula IXa wherein B, b and $C_x$ are as defined above.

In one embodiment, said at least one hydrophobic radical -Hy is chosen among the radicals according to formulas X, Xa to Xu wherein GpC is a radical according to formula IX wherein e=1, b=0 and GpC is a radical according to formula IXd.

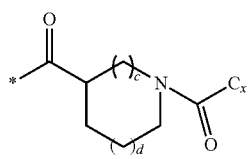

Formula IXd wherein c, d and $C_x$ are as defined above.

In one embodiment, said at least one hydrophobic radical -Hy is chosen among the radicals according to formula X wherein GpC is a radical according to formula IX wherein e=0, b=0 and GpC is a radical according to formula IXc

IXc wherein $C_x$ is as defined above.

In one embodiment, said at least one hydrophobic radical -Hy is chosen among the radicals according to formulas X, Xa to Xu wherein GpC is a radical according to formula IX wherein e=1 and GpC is a radical according to formula IXb.

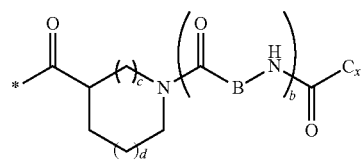

Formula IXb wherein c, d, B, b and $C_x$ are as defined above.

In one embodiment, said at least one hydrophobic radical -Hy is chosen among the radicals according to formula X wherein GpA is chosen among the radicals according to formula VIII wherein s'=1 represented by the formula VIIIa or according to formula VIII wherein s'=0 represented by the formula VIIIb:

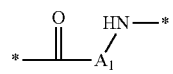

Formula VIIIa

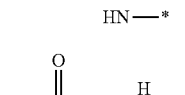

Formula VIIIb wherein $A_1$ is as defined above.

In one embodiment, said at least one hydrophobic radical -Hy is chosen among the radicals according to formula X wherein GpA is chosen among the radicals according to formula VIII wherein s'=1 represented by the formula VIIIc or the formula VIIId:

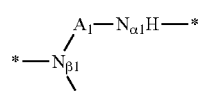

Formula VIIIc

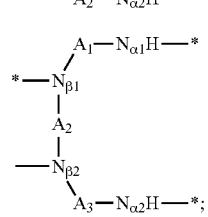

Formula VIIId wherein $A_1$, $A_2$ and $A_3$ are as defined above.

In the formulas, the * indicate the binding sites of the hydrophobic radicals to the PLG or between the different groups GpR, GpG, GpA, GpL, GpH and GpC to form amide functions.

The radicals -Hy are bounded to the PLG via amide functions.

In the formulas VII, VII' and VII", the * indicate, from left to right respectively, the binding sites of GpR:

to the PLG and to GpG if g≥1 or to GpA if g=0 or to GpL if l=1 and g=a=0 or to GpH if h≥1 and g=a=l=0 or GpC if a'=1 and g=a=l=h=0.

In the formulas VIIIa, VIIIb, VIIIc and VIIId, the * indicate, from left to right respectively, the binding sites of GpA:
 to GpG if g≥1 or to GpR if r=1 or 2 and g=0 or to the PLG if g=r=0 and
 to GpL if l=1 or to GpH if h≥1 and l=0 or to GpC if l=h=0
In the formula IX, the * indicates the binding site of GpC:
 to GpH if h≥1,
 to GpL if l=1 and h=0
 to GpA if a=1 and h=l=0
 to GpG if g≥1 and h=l=a=0
 to GpR if r=1 or 2 and h=l=a=g=0
 to the PLG if h=l=a=g=r=0

The radicals -Hy, GpR, GpG, GpA, GpL, GpH and GpC are each independently identical or different from one residue to another.

In one embodiment, if GpA is a radical according to formula VIIIc and r=1, then:
 the GpC are bound directly or indirectly to $N_{\alpha1}$ and $N_{\alpha2}$ and the PLG is bound directly or indirectly via—GpR to $N_{\beta1}$, or
 the GpC are bound directly or indirectly to $N_{\alpha1}$ and $N_{\beta1}$, and the PLG is bound directly or indirectly via—GpR to $N_{\beta2}$; or
 the GpC are bound directly or indirectly to $N_{\alpha2}$ and $Na_{\beta1}$, and the PLG is bound directly or indirectly via—GpR to $N_{\alpha1}$.

In one embodiment, if GpA is a radical according to formula VIIIc and r=0, then:
 the GpC are bound directly or indirectly to $N_{\alpha1}$ and $N_{\alpha2}$ and the PLG is bound directly or indirectly to $N_{\beta1}$; or
 GpC are bound directly or indirectly to $N_{\alpha1}$ and $N_{\beta1}$, the PLG is bound to directly or indirectly $N_{\alpha2}$; or
 the GpC are bound directly or indirectly to $N_{\alpha2}$ and $N_{\beta1}$, and the PLG is bound directly or indirectly to $N_{\alpha1}$.

In one embodiment, if GpA is a radical according to formula VIIId and r=1, then:
 the GpC are bound directly or indirectly to $N_{\alpha1}$, $N_{\alpha2}$, and $N_{\beta1}$ and the PLG is bound directly or indirectly via -GpR to $N_{\beta2}$; or
 the GpC are bound directly or indirectly to and —$N_{\alpha1}$, $N_{\alpha2}$ and $N_{\beta2}$ and the PLG is bound directly or indirectly via GpR to $N_{\beta1}$; or
 the GpC are bound directly or indirectly to $N_{\alpha1}$, $N_{\beta1}$, and $N_{\beta2}$ and the PLG is bound directly or indirectly via -GpR- to $N_{\alpha2}$; or
 the GpC are bound directly or indirectly to $N_{\alpha2}$, $N_{\beta1}$, and $N_{\beta2}$ and the PLG is bound directly or indirectly via GpR to $N_{\alpha1}$.

In one embodiment, if GpA is a radical according to formula VIIId r=0, then
 the GpC are bound directly or indirectly to —$N_{\alpha1}$, $N_{\alpha2}$ and $N_{\beta1}$ and the PLG is bound directly or indirectly to $N_{\beta2}$; or
 the GpC are bound directly or indirectly to $N_{\alpha1}$, $N_{\alpha2}$, and $N_{\beta2}$ and the PLG is bound directly or indirectly to $N_{\beta1}$; or
 the GpC are bound directly or indirectly to —$N_{\alpha1}$, $N_{\beta1}$, and $N_{\beta2}$ and the PLG is bound directly or indirectly to $N_{\alpha2}$; or
 the GpC are bound directly or indirectly to $N_{\alpha2}$, $N_{\beta1}$, and $N_{\beta2}$ and the PLG is bound directly or indirectly to $N_{\alpha1}$.

In one embodiment, if GpA is a radical according to formula VIIId r=0, then
 the GpC are bound directly or indirectly to $N_{\square\square}$, $N_{\square\square}$ and $N_{\square\square}$ and the PLG is bound directly or indirectly to $N_{\square\square}$; or
 the GpC are bound directly or indirectly to $N_{\square\square}$, $N_{\square\square}$ and $N_{\square\square}$ and the PLG is bound directly or indirectly to $N_{\square\square}$; or
 the GpC are bound directly or indirectly to $N_{\square\square}$ $N_{\square\square}$ and $N_{\square\square}$ and the PLG is bound directly or indirectly to $N_{\square\square}$; or
 the GpC are bound directly or indirectly to $N_{\square\square}$, $N_{\square\square}$ and $N_{\square\square}$ and the PLG is bound directly or indirectly to $N_{\square\square}$ In one embodiment, a=0.
In one embodiment, h=1 and g=0.
In one embodiment, h=0 and g=1.
In one embodiment, r=0, g=1 and h=0.
In one embodiment, r=1 and GpR is chosen among the radicals according to formula VII' or VII" and h=0.
In one embodiment, r=1, g=0 and GpR is a radical according to formula VII' and h=0.
In one embodiment, r=1, g=0 and GpR is a radical according to formula VII' and h=1.
In one embodiment, r=1, g=0, GpR is a radical according to formula VII', GpA is chosen among the radicals according to formula VIIIa or VIIIb and h=0.
In one embodiment, r=1, g=0, GpR is a radical according to formula VII', GpA is chosen among the radicals according to formula VIIIa or VIIIb and h=1.
In one embodiment, r=1, g=0, GpR is a radical according to formula VII', GpA is a radical according to formula VIIIa and h=0.
In one embodiment, r=1, g=0, GpR is a radical according to formula VII', GpA is a radical according to formula VIIIa and h=1.
In one embodiment, r=1, g=0, GpR is a radical according to formula VII', GpA is a radical according to formula VIIIb and h=0.
In one embodiment, r=1, g=0, GpR is a radical according to formula VII', GpA is a radical according to formula VIIIb and h=1.
In one embodiment, r=0, g=0 and GpA is chosen among the radicals according to formula VIIIa and VIIIb.
In one embodiment, r=0, g=0, GpA is chosen among the radicals according to formula VIIIa and VIIIb and h=0.

In one embodiment, the composition is characterized in that the hydrophobic radical according to formula X is a radical wherein R is a divalent linear alkyl radical comprising from 2 to 12 carbon atoms.

In one embodiment, the composition is characterized in that the hydrophobic radical according to formula X is a radical wherein R is a divalent alkyl radical comprising from 2 to 6 carbon atoms.

In one embodiment, the composition is characterized in that the hydrophobic radical according to formula X is a radical wherein R is a divalent linear alkyl radical comprising from 2 to 6 carbon atoms.

In one embodiment, the composition is characterized in that the hydrophobic radical according to formula X is a radical wherein R is a divalent alkyl radical comprising from 2 to 4 carbon atoms.

In one embodiment, the composition is characterized in that the hydrophobic radical according to formula X is a radical wherein R is a divalent linear alkyl radical comprising from 2 to 4 carbon atoms.

In one embodiment, the composition is characterized in that the hydrophobic radical according to formula X is a radical wherein R is a divalent alkyl radical comprising 2 carbon atoms.

In one embodiment, the composition is characterized in that the hydrophobic radical according to formula X is a radical wherein R is a divalent linear alkyl radical comprising from 1 to 11 carbon atoms.

In one embodiment, the composition is characterized in that the hydrophobic radical according to formula X is a radical wherein R is a divalent alkyl radical comprising from 1 to 6 carbon atoms.

In one embodiment, the composition is characterized in that the hydrophobic radical according to formula X is a radical wherein R is a divalent alkyl radical comprising from 2 to 5 carbon atoms and bearing one or a plurality of amide functions (—CONH2).

In one embodiment, the composition is characterized in that the hydrophobic radical according to formula X is a radical wherein R is a divalent linear alkyl radical comprising from 2 to 5 carbon atoms and bearing one or a plurality of amide functions (—CONH2).

In one embodiment, the composition is characterized in that the hydrophobic radical according to formula X is a radical wherein R is radical chosen in the group consisting of the radicals represented by the formulas hereinafter:

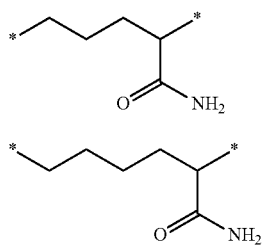

Formula X1

Formula X2

In one embodiment, the composition is characterized in that the hydrophobic radical according to formula X is a radical wherein R is a radical according to formula X1.

In one embodiment, the composition is characterized in that the hydrophobic radical according to formula X is a radical wherein R is a radical according to formula X2.

In one embodiment, the composition is characterized in that the hydrophobic radical according to formula X is a radical wherein R is bound to the co-polyamino acid via an amide function borne by the carbon in the delta or epsilon position (or in position 4 or 5) with respect to the amide function (—CONH2).

In one embodiment, the composition is characterized in that the hydrophobic radical according to formula X is a radical wherein R is a non-substituted ether or polyether linear radical comprising from 4 to 14 carbon atoms and from 1 to 5 oxygen atoms.

In one embodiment, the composition is characterized in that the hydrophobic radical according to formula X is a radical wherein R is an ether radical.

In one embodiment, the composition is characterized in that the hydrophobic radical according to formula X is a radical wherein R is an ether radical comprising from 4 to 6 carbon atoms.

In one embodiment, the composition is characterized in that the hydrophobic radical according to formula X is a radical wherein R is a divalent alkyl radical comprising 6 carbon atoms.

In one embodiment, the composition is characterized in that the hydrophobic radical according to formula X is a radical wherein R is an ether radical represented by the formula

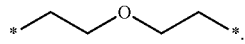

In one embodiment, the composition is characterized in that the hydrophobic radical according to formula X is a radical wherein R is a polyether radical.

In one embodiment, the composition is characterized in that the hydrophobic radical according to formula X is a radical wherein R is a polyether linear radical comprising from 6 to 10 carbon atoms and from 2 to 3 oxygen atoms.

In one embodiment, the composition is characterized in that the hydrophobic radical according to formula X is a radical wherein R is a polyether radical chosen in the group consisting of the radicals represented by the formulas hereinafter:

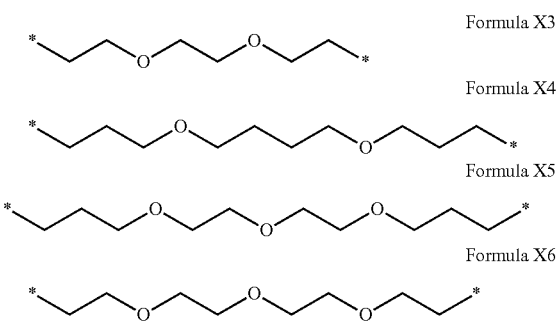

Formula X3

Formula X4

Formula X5

Formula X6

In one embodiment, the composition is characterized in that the hydrophobic radical according to formula X is a radical wherein R is a radical according to formula X3.

In one embodiment, the composition is characterized in that the hydrophobic radical according to formula X is a radical wherein R is a radical according to formula X4.

In one embodiment, the composition is characterized in that the hydrophobic radical according to formula X is a radical wherein R is a polyether radical chosen in the group consisting of the radicals represented by the formulas X5 and X6 hereinafter:

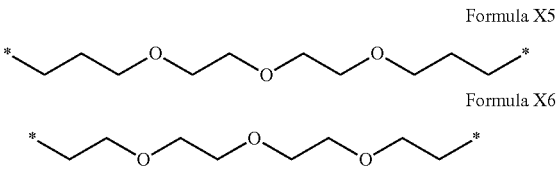

Formula X5

Formula X6

In one embodiment, the composition is characterized in that the hydrophobic radical according to formula X is a radical wherein R is a polyether radical according to formula X5.

In one embodiment, the composition is characterized in that the hydrophobic radical according to formula X is a radical wherein R is a polyether radical according to formula X6.

In one embodiment, the composition is characterized in that the hydrophobic radical according to formula X is a radical wherein the radical GpG and/or GpH is according to formula XI' wherein G is an alkyl radical comprising 6 carbon atoms represented by the formula Z hereinafter:

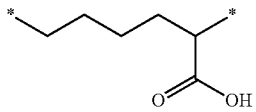

Formula Z

In one embodiment, the composition is characterized in that the hydrophobic radical according to formula X is a radical wherein the radical GpG and/or GpH is according to formula XI wherein G is an alkyl radical comprising 4 carbon atoms represented by the formula Z' hereinafter:

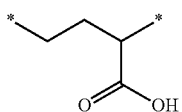

Formula Z'

In one embodiment, the composition is characterized in that the hydrophobic radical according to formula X is a radical wherein the radical GpG and/or GpH is according to formula XI wherein G is an alkyl radical comprising 4 carbon atoms represented by —(CH2)2—CH(COOH)—.

In one embodiment, the composition is characterized in that the hydrophobic radical according to formula X is a radical wherein the radical GpG and/or GpH is according to formula XI wherein G is an alkyl radical comprising 4 carbon atoms represented by —CH((CH2)2COOH)—.

In one embodiment, the composition is characterized in that the hydrophobic radical according to formula X is a radical wherein the radical GpG and/or GpH is according to formula XI wherein G is an alkyl radical comprising 3 carbon atoms represented by —CH2—CH—(COOH).

In one embodiment, the composition is characterized in that the hydrophobic radical according to formula X is a radical wherein the radical GpG and/or GpH is according to formula XI wherein G is an alkyl radical comprising 3 carbon atoms represented by —CH(CH2)(COOH)—.

In one embodiment, the composition is characterized in that the hydrophobic radical according to formula X is a radical wherein the radical GpA is according to formula VIII and wherein $A_1$ is chosen in the group consisting of radicals represented by the formulas hereinafter:

Formula Y1

Formula Y2

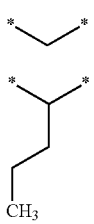

Formula Y3

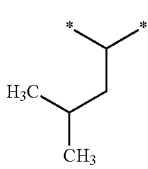

Formula Y4

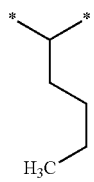

Formula Y5

Formula Y6

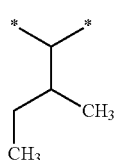

Formula Y7

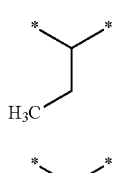

Formula Y8

Formula Y9

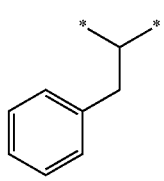

Formula Y10

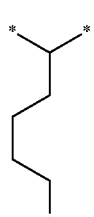

In one embodiment, the composition is characterized in that the hydrophobic radical according to formula X is a radical wherein the radical GpC according to formula IX is chosen in the group consisting of the radicals according to formulas IXe, IXf or IXg represented hereinafter:

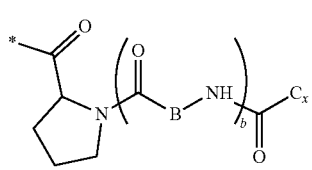

Formula IXe

-continued

Formula IXf

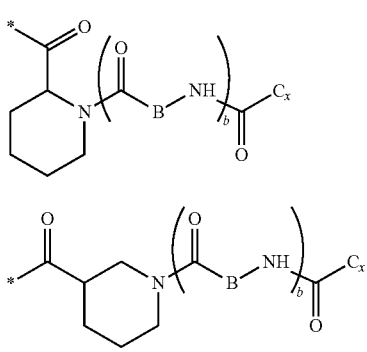

Formula IXg

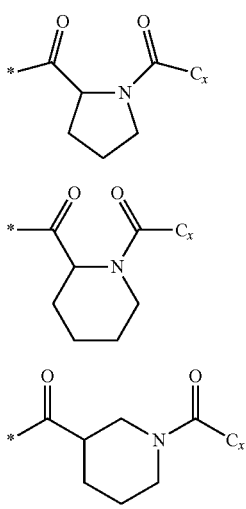

In one embodiment, the composition is characterized in that the hydrophobic radical according to formula X is a radical wherein the radical GpC according to formula IX is chosen in the group consisting of the radicals according to formulas IXe, IXf or IXg wherein b is equal to 0, respectively responding to formulas IXh, IXi, and IXj represented hereinafter:

Formula IXh

Formula IXi

Formula IXj

In one embodiment, the composition is characterized in that the hydrophobic radical according to formula X is a radical wherein the radical GpC responds to the formula IX or IXe wherein b=0, and observes the formula IXh.

In one embodiment, the composition is characterized in that the hydrophobic radical according to formula X is a radical wherein $C_x$ is chosen in the group consisting of linear alkyl radicals.

In one embodiment, the composition is characterized in that the hydrophobic radical according to formula X is a radical wherein $C_x$ is chosen in the group consisting of branched alkyl radicals.

In one embodiment, the composition is characterized in that the hydrophobic radical according to formula X is a radical wherein $C_x$ is chosen in the group consisting of alkyl radicals comprising from 9 to 14 carbon atoms.

In one embodiment, the composition is characterized in that the hydrophobic radical according to formula X is a radical wherein $C_x$ is chosen in the group consisting of the radicals represented by the formulas hereinafter:

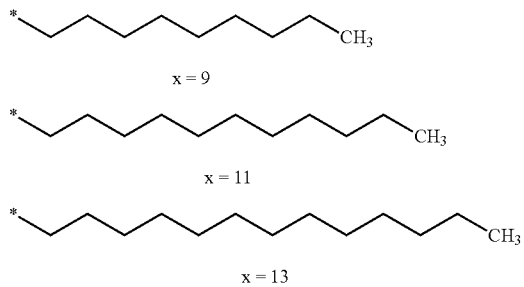

x = 9 x = 11 x = 13

In one embodiment, the composition is characterized in that the hydrophobic radical according to formula X is a radical wherein $C_x$ is chosen in the group consisting of alkyl radicals comprising from 15 to 16 carbon atoms.

In one embodiment, the composition is characterized in that the hydrophobic radical according to formula X is a radical wherein $C_x$ is chosen in the group consisting of the radicals represented by the formula hereinafter:

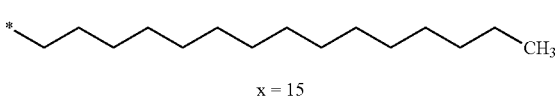

x = 15

In one embodiment, the composition is characterized in that the hydrophobic radical according to formula X is a radical wherein $C_x$ is chosen in the group consisting of the radicals represented by the formula hereinafter:

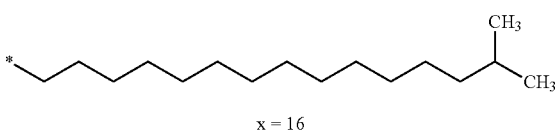 [SMILES: *CCCCCCCCCCCCCC(C)C]

x = 16

In one embodiment, the composition is characterized in that the hydrophobic radical according to formula X is a radical wherein $C_x$ is chosen in the group consisting of alkyl radicals comprising from 17 to 25 carbon atoms.

In one embodiment, the composition is characterized in that the hydrophobic radical according to formula X is a radical wherein $C_x$ is chosen in the group consisting of alkyl radicals comprising from 17 to 18 carbon atoms.

In one embodiment, the composition is characterized in that the hydrophobic radical according to formula X is a radical wherein $C_x$ is chosen in the group consisting of the alkyl radicals represented by the formula hereinafter:

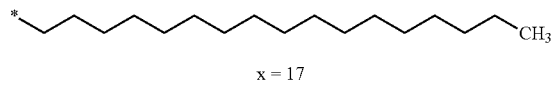

x = 17

In one embodiment, the composition is characterized in that the hydrophobic radical according to formula X is a radical wherein $C_x$ is chosen in the group consisting of alkyl radicals comprising from 18 to 25 carbon atoms.

In one embodiment, the composition is characterized in that the hydrophobic radical according to formula X is a radical wherein $C_x$ is chosen in the group consisting of the alkyl radicals represented by the formulas hereinafter:

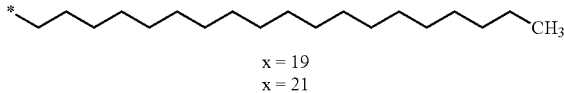 [SMILES: *CCCCCCCCCCCCCCCCCCC]

x = 19
x = 21

In one embodiment, the composition is characterized in that the hydrophobic radical is a radical according to formula X wherein the radical GpC according to formula IX is chosen in the group consisting of the radicals wherein $C_x$ is chosen in the group consisting of alkyl radicals comprising 14 or 15 carbon atoms.

In one embodiment, the composition is characterized in that the hydrophobic radical is a radical according to formula X wherein the radical GpC according to formula IX is chosen in the group consisting of the radicals wherein $C_x$ is chosen in the group consisting of the radicals represented by the formula hereinafter:

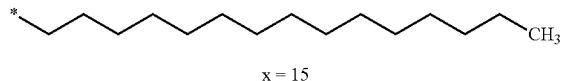 [SMILES: *CCCCCCCCCCCCCCC]

x = 15

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X, Xc', Xd Xa, Xc, Xe, Xg, Xh, Xj, Xk, Xm', Xn, Xq, Xr, Xs, Xo and Xt wherein a'=1 and l'=1 and GpC is a radical according to formula IXe.

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X, Xc', Xd Xa, Xc, Xe, Xg, Xh, Xj, Xk, Xm', Xn, Xq, Xr, Xs, Xo and Xt wherein a'=1 and l'=1 and GpC is a radical according to formula IX wherein e=0.

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X, Xc', Xd, Xa, Xb, Xc, Xf, Xg, Xh, Xi, Xj, Xl, Xp, Xq, Xr, Xs Xt, Xt' and Xu wherein a'=2 or l'=2 and GpC is a radical according to formula IXe.

In one embodiment, the co-polyamino acid is chosen among the co-polyamino acids according to formula XXXb wherein the hydrophobic radical -Hy is chosen in the group of hydrophobic radicals according to formula X, Xc', Xd, Xa, Xb, Xc, Xf, Xg, Xh, Xi, Xj, Xl, Xp, Xq, Xr, Xs Xt, Xt' and Xu wherein a'=2 or l'=2 and GpC is a radical according to formula IX wherein e=0.

In one embodiment, the composition is characterized in that the ratio M between the number of hydrophobic radicals and the number of glutamic or aspartic units is comprised from 0.007 to 0.3.

In one embodiment, the composition is characterized in that the ratio M between the number of hydrophobic radicals and the number of glutamic or aspartic units is comprised from 0.01 to 0.3.

In one embodiment, the composition is characterized in that the ratio M between the number of hydrophobic radicals and the number of glutamic or aspartic units is comprised from 0.02 to 0.2.

In one embodiment, the composition is characterized in that the hydrophobic radical responds to formula X and the ratio M between the number of hydrophobic radicals and the number of glutamic or aspartic units is comprised from 0.007 to 0.15.

In one embodiment, the composition is characterized in that the hydrophobic radical responds to formula X and the ratio M between the number of hydrophobic radicals and the number of glutamic or aspartic units is comprised from 0.01 to 0.1.

In one embodiment, the composition is characterized in that the hydrophobic radical responds to formula X and the ratio M between the number of hydrophobic radicals and the number of glutamic or aspartic units is comprised from 0.02 to 0.08.

In one embodiment, the composition is characterized in that the hydrophobic radical responds to formula X wherein the radical $C_x$ comprises from 9 to 10 carbon atoms and the ratio M between the number of hydrophobic radicals and the number of glutamic or aspartic units is comprised from 0.03 to 0.15.

In one embodiment, the composition is characterized in that the hydrophobic radical responds to formula X wherein the radical $C_x$ comprises from 11 to 12 carbon atoms and the ratio M between the number of hydrophobic radicals and the number of glutamic or aspartic units is comprised from 0.015 to 0.1.

In one embodiment, the composition is characterized in that the hydrophobic radical responds to formula X wherein the radical $C_x$ comprises from 11 to 12 carbon atoms and the ratio M between the number of hydrophobic radicals and the number of glutamic or aspartic units is comprised from 0.02 to 0.08.

In one embodiment, the composition is characterized in that the hydrophobic radical responds to formula X wherein the radical $C_x$ comprises from 13 to 15 carbon atoms and the ratio M between the number of hydrophobic radicals and the number of glutamic or aspartic units is comprised from 0.01 to 0.1.

In one embodiment, the composition is characterized in that the hydrophobic radical responds to formula X wherein the radical $C_x$ comprises from 13 to 15 carbon atoms and the ratio M between the number of hydrophobic radicals and the number of glutamic or aspartic units is comprised from 0.01 to 0.06.

In one embodiment, the composition is characterized in that the hydrophobic radical responds to formula X and the ratio M between the number of hydrophobic radicals and the number of glutamic or aspartic units is comprised from 0.007 to 0.3.

In one embodiment, the composition is characterized in that the hydrophobic radical responds to formula X and the ratio M between the number of hydrophobic radicals and the number of glutamic or aspartic units is comprised from 0.01 to 0.3.

In one embodiment, the composition is characterized in that the hydrophobic radical responds to formula X and the ratio M between the number of hydrophobic radicals and the number of glutamic or aspartic units is comprised from 0.015 to 0.2.

In one embodiment, the composition is characterized in that the hydrophobic radical responds to formula X wherein the radical $C_x$ comprises from 11 to 14 carbon atoms and the ratio M between the number of hydrophobic radicals and the number of glutamic or aspartic units is comprised from 0.1 to 0.2.

In one embodiment, the composition is characterized in that the hydrophobic radical responds to formula X wherein the radical $C_x$ comprises from 15 to 16 carbon atoms and the ratio M between the number of hydrophobic radicals and the number of glutamic or aspartic units is comprised from 0.04 to 0.15.

In one embodiment, the composition is characterized in that the hydrophobic radical responds to formula X wherein the radical $C_x$ comprises from 17 to 18 carbon atoms and the ratio M between the number of hydrophobic radicals and the number of glutamic or aspartic units is comprised from 0.02 to 0.06.

In one embodiment, the composition is characterized in that the hydrophobic radical responds to formula X wherein the radical $C_x$ comprises from 19 to 25 carbon atoms and the ratio M between the number of hydrophobic radicals and the number of glutamic or aspartic units is comprised from 0.01 to 0.06.

In one embodiment, the composition is characterized in that the hydrophobic radical responds to formula X wherein the radical $C_x$ comprises from 19 to 25 carbon atoms and the ratio M between the number of hydrophobic radicals and the number of glutamic or aspartic units is comprised from 0.01 to 0.05.

The invention also relates to said co-polyamino acids I, bearing carboxylate charges and hydrophobic radicals according to formula X and the precursors of said hydrophobic radicals.

The invention also relates to a co-polyamino acid bearing carboxylate charges carboxylates and at least one hydrophobic radical according to formula X, said co-polyamino acid being chosen among the co-polyamino acids according to formula I:

  Formula I wherein:
j≥1; 0≤j'≤n'1 and j+j'≥1 and k≥2 said co-polyamino acid according to formula I bearing at least one hydrophobic radical -Hy, carboxylate charges and consisting of at least two chains of glutamic or aspartic units PLG bound together by an at least divalent linear or branched radical or spacer Q[-*]$_k$ consisting of an alkyl chain comprising one or a plurality of heteroatoms chosen in the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions.

said radical or spacer Q[-*]k being bound to at least two glutamic or aspartic unit chains PLG by an amide function and, said amide bonds binding said radical or spacer Q[-*]k bound to said at least two chains of glutamic or aspartic units result from the reaction between an amine function and an acid function respectively borne either by the precursor Q' of the radical or spacer Q[-*]$_k$ or by a glutamic or aspartic unit, said hydrophobic radical -Hy being bound either to a terminal "amino acid" unit and then j≥1, or to a carboxyl function borne by one of the chains of the glutamic or aspartic units PLG and then j'=n'1 and n'1 is the mean number of monomeric units bearing a hydrophobic radical -Hy.

In one embodiment, the invention also relates to the precursors Hy' of said hydrophobic radicals according to formula X' as defined hereinafter:

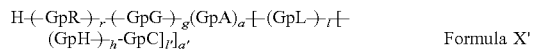  Formula X' wherein
GpR is chosen among the radicals according to formulas VII, VII' or VII":

  Formula VII

  Formula VII'

  Formula VII";

GpG and GpH identical or different are chosen among the radicals according to formulas XI or XI':

  Formula XI

  Formula XI'

GpA is chosen among the radicals according to formula VIII

  Formula VIII wherein A' is chosen among the radicals according to VIII', VIII" or VIII'''

  Formula VIII'

  Formula VIII"

  Formula VIII'''

GpL is chosen among the radicals according to formula XII

  Formula XII

GpC is a radical according to formula IX:

$$\left(*\underset{}{\overset{O}{\|}}-\left(\overset{}{\underset{}{\bigcirc}}\right)_{c}\underset{(\phantom{}}{}_{d})_{e}\right)_{a}\left(\overset{O}{\|}-B-\overset{H}{\underset{}{N}}-\overset{}{\underset{O}{}}\right)_{b}C_{x};$$

Formula IX the * indicate the binding sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
l' is an integer equal to 1 or to 2;
r is an integer equal to 0, 1 or to 2, and
s' is an integer equal to 0 or 1;
A, $A_1$, $A_2$ and $A_3$ identical or different are linear or branched alkyl radicals comprising from 1 to 8 carbon atoms and optionally substituted by a radical from a saturated, unsaturated or aromatic ring;
B is a radical chosen in the group consisting of a non-substituted ether or polyether radical comprising from 4 to 14 carbon atoms and from 1 to 5 oxygen atoms or a linear or branched alkyl radical, optionally comprising an aromatic nucleus, comprising from 1 to 9 carbon atoms;
$C_x$ is a radical chosen in the group consisting of a linear or branched monovalent alkyl radical, optionally comprising a cyclic part, wherein x indicates the number of carbon atoms and $6 \leq x \leq 25$:
  When the hydrophobic radical -Hy bears 1 -GpC, then $9 \leq x \leq 25$,
  When the hydrophobic radical -Hy bears 2 -GpC, then $9 \leq x \leq 15$,
  When the hydrophobic radical -Hy bears 3 -GpC, then $7 \leq x \leq 13$,
  When the hydrophobic radical -Hy bears 4 -GpC, then $7 \leq x \leq 11$,
  When the hydrophobic radical -Hy bears at least 5 -GpC, then $6 \leq x \leq 11$;
G is a linear or branched divalent alkyl radical of 1 to 8 carbon atoms, said alkyl radical bearing one or a plurality of free carboxylic acid function(s),
R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms the hydrophobic radical(s) -Hy according to formula X being bound to the PLG:
  via a covalent bond between a carbonyl of the hydrophobic radical -Hy and a nitrogen atom borne by the PLG thus forming an amide function obtained from the reaction of an amine function borne by the PLG and an acid function borne by the precursor Hy' of the hydrophobic radical -Hy and/or
  via a covalent bond between a nitrogen atom of the hydrophobic radical -Hy and a carbonyl borne by the PLG thus forming an amide function obtained from the reaction of an amine function of the precursor Hy' of the hydrophobic radical -Hy and an acid function borne by the PLG;
the ratio M between the number of hydrophobic radicals and the number of glutamic or aspartic units being comprised from $0 < M \leq 0.5$;
when a plurality of hydrophobic radicals are borne by a co-polyamino acid then they are identical or different;
the degree of polymerization DP in glutamic or aspartic units for the PLG chains is comprised from 5 to 250;
the free acid functions being in the form of alkali cation salt chosen in the group consisting of $Na^+$ and $K^+$.

Amylin, or islet amyloid polypeptide (IAPP), is a peptide hormone with 37 residues. It is co-secreted with insulin from pancreatic beta cells in a ratio of approximately 100:1. Amylin plays a role in blood sugar regulation by stopping endogenous glucagon secretion and by slowing down gastric emptying and by promoting satiety, thus reducing postprandial blood sugar deviations in blood glucose levels.

IAPP is treated using a coding sequence of 89 residues. The amyloid polypeptide Proislet (proIAPP, proamylin, proislet protein) is produced in pancreatic beta cells (beta cells) in the form of a pro-peptide of RSO 67 amino acids, 7404 Dalton, and undergoes post-translational modification comprising the cleavage of protease to produce amylin.

In the present applications, the amylin as cited refers to the compounds described in the U.S. Pat. Nos. 5,124,314 and 5,234,906.

The term "analog" denotes, when used with reference to a peptide or a protein, a peptide or a protein, wherein one or a plurality of constituent amino acid residues of the primary sequence have been substituted by other amino acid residues and/or wherein one or a plurality of constituent amino acid residues have been removed and/or wherein one or a plurality of constituent amino acid residues have been added. The percentage of homology allowed for the present definition of an analog is 50%. In the case of amylin, an analog may be for example derived from the primary amino acid sequence of amylin by substituting one or a plurality of natural or non-natural or peptidomimetic amino acids.

The term "derivative" denotes, when used with reference to a peptide or a protein, a peptide or a protein or an analog chemically modified by a substituent which is not present in the reference peptide or protein or analog, i.e. a peptide or a protein which has been modified by creating covalent bonds, to introduce non-amino acid type substituents.

An amylin receptor agonist refers to a compound imitating one or a plurality of amylin activity characteristics.

Amylin derivatives are described in the article Yan et al., PNAS, vol. 103, no 7, p 2046-2051, 2006.

In one embodiment, the substituent is chosen in the group consisting of fatty chains.

Amylin analogs are described in the U.S. Pat. Nos. 5,686,411, 6,114,304 or indeed U.S. Pat. No. 6,410,511.

In one embodiment, the composition is characterized in that the amylin analog is pramlintide (Symlin®) marketed by ASTRAZENECA AB.

In one embodiment, the composition is characterized in that it comprises amylin, amylin receptor agonist or amylin analog at a concentration ranging from 0.1 to 5 mg/ml.

In one embodiment, the composition is characterized in that it comprises amylin, amylin receptor agonist or amylin analog at a concentration ranging from 0.2 to 4 mg/ml.

In one embodiment, the composition is characterized in that it comprises amylin, amylin receptor agonist or amylin analog at a concentration ranging from 0.3 to 3 mg/ml.

In one embodiment, the composition is characterized in that it comprises amylin, amylin receptor agonist or amylin analog at a concentration ranging from 0.4 to 2 mg/ml.

In one embodiment, the composition is characterized in that it comprises amylin, amylin receptor agonist or amylin analog at a concentration ranging from 0.5 to 1.5 mg/ml.

In one embodiment, the composition is characterized in that it comprises amylin, amylin receptor agonist or amylin analog at a concentration ranging from 0.5 to 1 mg/ml.

In one embodiment, the composition is characterized in that it comprises amylin, amylin receptor agonist or amylin analog at a concentration of 0.6 mg/ml.

In one embodiment, the composition is characterized in that it comprises amylin, amylin receptor agonist or amylin analog at a concentration of 0.9 mg/ml.

In one embodiment, the molar ratios of co-polyamino acid/amylin, amylin receptor agonist or amylin analog is greater than or equal to 1.

In one embodiment, the molar ratios of co-polyamino acid/amylin, amylin receptor agonist or amylin analog are comprised from 1.5 to 75.

In one embodiment, the molar ratios of co-polyamino acid/amylin, amylin receptor agonist or amylin analog are comprised from 1.8 to 50.

In one embodiment, the molar ratios of co-polyamino acid/amylin, amylin receptor agonist or amylin analog are comprised from 2 to 35.

In one embodiment, the molar ratios of co-polyamino acid/amylin, amylin receptor agonist or amylin analog are comprised from 2.5 to 30.

In one embodiment, the molar ratios of co-polyamino acid/amylin, amylin receptor agonist or amylin analog are comprised from 3 to 30.

In one embodiment, the molar ratios of co-polyamino acid/amylin, amylin receptor agonist or amylin analog are comprised from 3.5 to 30.

In one embodiment, the molar ratios of co-polyamino acid/amylin, amylin receptor agonist or amylin analog are comprised from 4 to 30.

In one embodiment, the molar ratios of co-polyamino acid/amylin, amylin receptor agonist or amylin analog are comprised from 5 to 30.

In one embodiment, the molar ratios of co-polyamino acid/amylin, amylin receptor agonist or amylin analog are comprised from 7 to 30.

In one embodiment, the molar ratios of co-polyamino acid/amylin, amylin receptor agonist or amylin analog are comprised from 9 to 30.

In one embodiment, the molar ratios of co-polyamino acid/amylin are comprised from 3 to 75.

In one embodiment, the molar ratios of co-polyamino acid/amylin are comprised from 7 to 50.

In one embodiment, the molar ratios of co-polyamino acid/amylin are comprised from 10 to 30.

In one embodiment, the molar ratios of co-polyamino acid/amylin are comprised from 15 to 30

In one embodiment, the molar ratios of co-polyamino acid/pramlintide are comprised from 1.5 to 75.

In one embodiment, the molar ratios of co-polyamino acid/pramlintide are comprised from 2 to 50.

In one embodiment, the molar ratios of co-polyamino acid/pramlintide are comprised from 3 to 30.

In one embodiment, the molar ratios of co-polyamino acid/pramlintide are comprised from 4 to 30.

In one embodiment, the molar ratios of co-polyamino acid/pramlintide are comprised from 5 to 30.

In one embodiment, the molar ratios of co-polyamino acid/pramlintide are comprised from 8 to 30.

In one embodiment, the molar ratios of co-polyamino acid/pramlintide are comprised from 10 to 30.

In one embodiment, the molar ratios of hydrophobic radical Hy/amylin, amylin receptor agonist or amylin analog are comprised from 1.5 to 150.

In one embodiment, the molar ratios of hydrophobic radical Hy/amylin, amylin receptor agonist or amylin analog are comprised from 1.8 to 100.

In one embodiment, the molar ratios of hydrophobic radical Hy/amylin, amylin receptor agonist or amylin analog are comprised from 2 to 70.

In one embodiment, the molar ratios of hydrophobic radical Hy/amylin, amylin receptor agonist or amylin analog are comprised from 2.5 to 60.

In one embodiment, the molar ratios of hydrophobic radical Hy/amylin, amylin receptor agonist or amylin analog are comprised from 3 to 60.

In one embodiment, the molar ratios of hydrophobic radical Hy/amylin, amylin receptor agonist or amylin analog are comprised from 3.5 to 60.

In one embodiment, the molar ratios of hydrophobic radical Hy/amylin, amylin receptor agonist or amylin analog are comprised from 4 to 60.

In one embodiment, the molar ratios of hydrophobic radical Hy/amylin, amylin receptor agonist or amylin analog are comprised from 5 to 60.

In one embodiment, the molar ratios of hydrophobic radical Hy/amylin, amylin receptor agonist or amylin analog are comprised from 7 to 60.

In one embodiment, the molar ratios of hydrophobic radical Hy/amylin, amylin receptor agonist or amylin analog are comprised from 9 to 60.

In one embodiment, the molar ratios of hydrophobic radical Hy/amylin are comprised from 5 to 60.

In one embodiment, the molar ratios of hydrophobic radical Hy/amylin are comprised from 10 to 60.

In one embodiment, the molar ratios of hydrophobic radical Hy/amylin are comprised from 15 to 60.

In one embodiment, the molar ratios of hydrophobic radical Hy/pramlintide are comprised from 1.5 to 60.

In one embodiment, the molar ratios of hydrophobic radical Hy/pramlintide are comprised from 2 to 60.

In one embodiment, the molar ratios of hydrophobic radical Hy/pramlintide are comprised from 3 to 60.

In one embodiment, the molar ratios of hydrophobic radical Hy/pramlintide are comprised from 4 to 60.

In one embodiment, the molar ratios of hydrophobic radical Hy/pramlintide are comprised from 5 to 60.

In one embodiment, the molar ratios of hydrophobic radical Hy/pramlintide are comprised from 8 to 60.

In one embodiment, the molar ratios of hydrophobic radical Hy/pramlintide are comprised from 10 to 60.

In one embodiment, the mass ratios of co-polyamino acid/amylin, amylin receptor agonist or amylin analog are comprised from 1.0 to 70.

In one embodiment, the mass ratios of co-polyamino acid/amylin, amylin receptor agonist or amylin analog are comprised from 1.2 to 45.

In one embodiment, the mass ratios of co-polyamino acid/amylin, amylin receptor agonist or amylin analog are comprised from 1.3 to 30.

In one embodiment, the mass ratios of co-polyamino acid/amylin, amylin receptor agonist or amylin analog are comprised from 1.7 to 27.

In one embodiment, the mass ratios of co-polyamino acid/amylin, amylin receptor agonist or amylin analog are comprised from 2.0 to 27.

In one embodiment, the mass ratios of co-polyamino acid/amylin, amylin receptor agonist or amylin analog are comprised from 2.3 to 27.

In one embodiment, the mass ratios of co-polyamino acid/amylin, amylin receptor agonist or amylin analog are comprised from 2.7 to 27.

In one embodiment, the mass ratios of co-polyamino acid/amylin, amylin receptor agonist or amylin analog are comprised from 3.3 to 27.

In one embodiment, the mass ratios of co-polyamino acid/amylin, amylin receptor agonist or amylin analog are comprised from 4.7 to 27.

In one embodiment, the mass ratios of co-polyamino acid/amylin, amylin receptor agonist or amylin analog are comprised from 6.0 to 27.

In one embodiment, the mass ratios of co-polyamino acid/amylin are comprised from 2.0 to 67.

In one embodiment, the mass ratios of co-polyamino acid/amylin are comprised from 4.7 to 27.

In one embodiment, the mass ratios of co-polyamino acid/amylin are comprised from 6.7 to 27.

In one embodiment, the mass ratios of co-polyamino acid/amylin are comprised from 10 to 27.

In one embodiment, the mass ratios of co-polyamino acid/pramlintide are comprised from 1.0 to 67.

In one embodiment, the mass ratios of co-polyamino acid/pramlintide are comprised from 1.3 to 45.

In one embodiment, the mass ratios of co-polyamino acid/pramlintide are comprised from 2.7 to 27.

In one embodiment, the mass ratios of co-polyamino acid/pramlintide are comprised from 3.3 to 27.

In one embodiment, the mass ratios of co-polyamino acid/pramlintide are comprised from 5.3 to 27.

In one embodiment, the mass ratios of co-polyamino acid/pramlintide are comprised from 6.7 to 27.

In one embodiment, the composition according to the invention is characterized in that it further comprises insulin.

In one embodiment, the composition is characterized in that the insulin is a prandial insulin. Prandial insulins are soluble at pH 7.

Prandial insulin denotes a so-called rapid-acting or "regular" insulin.

So-called rapid-acting prandial insulins are insulins required to meet the needs induced by the intake of proteins and carbohydrates during a meal, they must act in less than 30 minutes.

In one embodiment, the so-called "regular" prandial insulin is human insulin.

In one embodiment, the prandial insulin is a recombinant human insulin described in the European Pharmacopeia and the US Pharmacopeia.

Human insulin is for example marketed under the trade names Humulin® (ELI LILLY) and Novolin® (NOVO NORDISK).

So-called rapid-acting (fast-acting) prandial insulins are insulins obtained by recombination and wherein the primary sequence has been modified to reduce the duration of action thereof.

In one embodiment, the so-called rapid-acting (fast-acting) insulins are chosen in the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

The pharmacopeia recommended units for insulins are presented in the table hereinafter with the equivalences thereof in mg:

| Insulin | EP Pharmacopeia 8.0 (2014) | US Pharmacopeia - USP38 (2015) |
|---|---|---|
| Aspart | 1U = 0.0350 mg of insulin aspart | 1 USP = 0.0350 mg insulin aspart |
| Lispro | 1U = 0.0347 mg of insulin lispro | 1 USP = 0.0347 mg of insulin lispro |
| Human | 1IU = 0.0347 mg of human insulin | 1 USP = 0.0347 mg of human insulin |

In the case of insulin glulisine, 100 U=3.49 mg of insulin glulisine (as per "Annex 1—Summary of product characteristics" in relation to ADIPRA®).

Nevertheless, hereinafter in the text, U is systematically used indiscriminately for the quantities and concentrations of all insulins. The respective equivalent values in mg are those given above for the values expressed in U, IU or USP.

In one embodiment, it relates to a pharmaceutical formulation characterized in that the insulin concentration is comprised from 240 to 3000 µM (40 to 500 U/mL).

In one embodiment, it relates to a pharmaceutical formulation characterized in that the insulin concentration is comprised from 600 to 3000 µM (100 to 500 U/mL).

In one embodiment, it relates to a pharmaceutical formulation characterized in that the insulin concentration is comprised from 600 to 2400 µM (100 to 400 U/mL).

In one embodiment, it relates to a pharmaceutical formulation characterized in that the insulin concentration is comprised from 600 to 1800 µM (100 to 300 U/mL).

In one embodiment, it relates to a pharmaceutical formulation characterized in that the insulin concentration is comprised from 600 to 1200 µM (100 to 200 U/mL).

In one embodiment, it relates to a pharmaceutical formulation characterized in that the insulin concentration is 600 µM (100 U/mL).

In one embodiment, it relates to a pharmaceutical formulation characterized in that the insulin concentration is 1200 µM (200 U/mL).

In one embodiment, it relates to a pharmaceutical formulation characterized in that the insulin concentration is 1800 µM (300 U/mL).

In one embodiment, it relates to a pharmaceutical formulation characterized in that the insulin concentration is 2400 µM (400 U/mL).

In one embodiment, it relates to a pharmaceutical formulation characterized in that the insulin concentration is 3000 µM (500 U/mL).

In one embodiment the molar ratio of co-polyamino acid/insulin is greater than or equal to 1.

In one embodiment comprising prandial insulin, the molar ratios of co-polyamino acid/amylin, amylin receptor agonist or amylin analog are comprised from 1.5 to 75.

In one embodiment comprising prandial insulin, the molar ratios of co-polyamino acid/amylin, amylin receptor agonist or amylin analog are comprised from 1.8 to 50.

In one embodiment comprising prandial insulin, the molar ratios of co-polyamino acid/amylin, amylin receptor agonist or amylin analog are comprised from 2 to 35.

In one embodiment comprising prandial insulin, the molar ratios of co-polyamino acid/amylin, amylin receptor agonist or amylin analog are comprised from 2.5 to 30.

In one embodiment comprising prandial insulin, the molar ratios of co-polyamino acid/amylin, amylin receptor agonist or amylin analog are comprised from 3 to 30.

In one embodiment comprising prandial insulin, the molar ratios of co-polyamino acid/amylin, amylin receptor agonist or amylin analog are comprised from 3.5 to 30.

In one embodiment comprising prandial insulin, the molar ratios of co-polyamino acid/amylin, amylin receptor agonist or amylin analog are comprised from 4 to 30.

In one embodiment comprising prandial insulin, the molar ratios of co-polyamino acid/amylin, amylin receptor agonist or amylin analog are comprised from 5 to 30.

In one embodiment comprising prandial insulin, the molar ratios of co-polyamino acid/amylin, amylin receptor agonist or amylin analog are comprised from 7 to 30.

In one embodiment comprising prandial insulin, the molar ratios of co-polyamino acid/amylin, amylin receptor agonist or amylin analog are comprised from 9 to 30.

In one embodiment comprising prandial insulin, the molar ratios of co-polyamino acid/amylin are comprised from 5 to 75.

In one embodiment comprising prandial insulin, the molar ratios of co-polyamino acid/amylin are comprised from 10 to 50.

In one embodiment comprising prandial insulin, the molar ratios of co-polyamino acid/amylin are comprised from 15 to 30.

In one embodiment comprising prandial insulin, the molar ratios of co-polyamino acid/pramlintide are comprised from 1.5 to 75.

In one embodiment comprising prandial insulin, the molar ratios of co-polyamino acid/pramlintide are comprised from 2 to 50.

In one embodiment comprising prandial insulin, the molar ratios of co-polyamino acid/pramlintide are comprised from 3 to 30.

In one embodiment comprising prandial insulin, the molar ratios of co-polyamino acid/pramlintide are comprised from 4 to 30.

In one embodiment comprising prandial insulin, the molar ratios of co-polyamino acid/pramlintide are comprised from 5 to 30.

In one embodiment comprising prandial insulin, the molar ratios of co-polyamino acid/pramlintide are comprised from 8 to 30.

In one embodiment comprising prandial insulin, the molar ratios of co-polyamino acid/pramlintide are comprised from 10 to 30.

In one embodiment comprising prandial insulin, the molar ratios of hydrophobic radical -Hy/amylin, amylin receptor agonist or amylin analog are comprised from 1.5 to 150.

In one embodiment comprising prandial insulin, the molar ratios of hydrophobic radical -Hy/amylin, amylin receptor agonist or amylin analog are comprised from 1.8 to 100.

In one embodiment comprising prandial insulin, the molar ratios of hydrophobic radical -Hy/amylin, amylin receptor agonist or amylin analog are comprised from 2 to 70.

In one embodiment comprising prandial insulin, the molar ratios of hydrophobic radical -Hy/amylin, amylin receptor agonist or amylin analog are comprised from 2.5 to 60.

In one embodiment comprising prandial insulin, the molar ratios of hydrophobic radical -Hy/amylin, amylin receptor agonist or amylin analog are comprised from 3 to 60.

In one embodiment comprising prandial insulin, the molar ratios of hydrophobic radical -Hy/amylin, amylin receptor agonist or amylin analog are comprised from 3.5 to 60.

In one embodiment comprising prandial insulin, the molar ratios of hydrophobic radical -Hy/amylin, amylin receptor agonist or amylin analog are comprised from 4 to 60.

In one embodiment comprising prandial insulin, the molar ratios of hydrophobic radical -Hy/amylin, amylin receptor agonist or amylin analog are comprised from 5 to 60.

In one embodiment comprising prandial insulin, the molar ratios of hydrophobic radical -Hy/amylin, amylin receptor agonist or amylin analog are comprised from 7 to 60.

In one embodiment comprising prandial insulin, the molar ratios of hydrophobic radical -Hy/amylin, amylin receptor agonist or amylin analog are comprised from 9 to 60.

In one embodiment comprising prandial insulin, the molar ratios of hydrophobic radical -Hy/amylin are comprised from 5 to 60.

In one embodiment comprising prandial insulin, the molar ratios of hydrophobic radical -Hy/amylin are comprised from 10 to 60.

In one embodiment comprising prandial insulin, the molar ratios of hydrophobic radical -Hy/amylin are comprised from 15 to 60.

In one embodiment comprising prandial insulin, the molar ratios of hydrophobic radical -Hy/pramlintide are comprised from 1.5 to 60.

In one embodiment comprising prandial insulin, the molar ratios of hydrophobic radical -Hy/pramlintide are comprised from 2 to 60.

In one embodiment comprising prandial insulin, the molar ratios of hydrophobic radical -Hy/pramlintide are comprised from 3 to 60.

In one embodiment comprising prandial insulin, the molar ratios of hydrophobic radical -Hy/pramlintide are comprised from 4 to 60.

In one embodiment comprising prandial insulin, the molar ratios of hydrophobic radical -Hy/pramlintide are comprised from 5 to 60.

In one embodiment comprising prandial insulin, the molar ratios of hydrophobic radical -Hy/pramlintide are comprised from 8 to 60.

In one embodiment comprising prandial insulin, the molar ratios of hydrophobic radical -Hy/pramlintide are comprised from 10 to 60.

In one embodiment comprising prandial insulin, the mass ratios of co-polyamino acid/amylin, amylin receptor agonist or amylin analog are comprised from 1.0 to 70.

In one embodiment comprising prandial insulin, the mass ratios of co-polyamino acid/amylin, amylin receptor agonist or amylin analog are comprised from 1.2 to 45.

In one embodiment comprising prandial insulin, the mass ratios of co-polyamino acid/amylin, amylin receptor agonist or amylin analog are comprised from 1.3 to 30.

In one embodiment comprising prandial insulin, the mass ratios of co-polyamino acid/amylin, amylin receptor agonist or amylin analog are comprised from 1.7 to 27.

In one embodiment comprising prandial insulin, the mass ratios of co-polyamino acid/amylin, amylin receptor agonist or amylin analog are comprised from 2.0 to 27.

In one embodiment comprising prandial insulin, the mass ratios of co-polyamino acid/amylin, amylin receptor agonist or amylin analog are comprised from 2.3 to 27.

In one embodiment comprising prandial insulin, the mass ratios of co-polyamino acid/amylin, amylin receptor agonist or amylin analog are comprised from 2.7 to 27.

In one embodiment comprising prandial insulin, the mass ratios of co-polyamino acid/amylin, amylin receptor agonist or amylin analog are comprised from 3.3 to 27.

In one embodiment comprising prandial insulin, the mass ratios of co-polyamino acid/amylin, amylin receptor agonist or amylin analog are comprised from 4.7 to 27.

In one embodiment comprising prandial insulin, the mass ratios of co-polyamino acid/amylin, amylin receptor agonist or amylin analog are comprised from 6.0 to 27.

In one embodiment comprising prandial insulin, the mass ratios of co-polyamino acid/amylin are comprised from 3.3 to 67.

In one embodiment comprising prandial insulin, the mass ratios of co-polyamino acid/amylin are comprised from 6.6 to 27.

In one embodiment comprising prandial insulin, the mass ratios of co-polyamino acid/amylin are comprised from 10 to 27.

In one embodiment comprising prandial insulin, the mass ratios of co-polyamino acid/pramlintide are comprised from 1.0 to 67.

In one embodiment comprising prandial insulin, the mass ratios of co-polyamino acid/pramlintide are comprised from 1.2 to 45.

In one embodiment comprising prandial insulin, the mass ratios of co-polyamino acid/pramlintide are comprised from 1.3 to 27.

In one embodiment comprising prandial insulin, the mass ratios of co-polyamino acid/pramlintide are comprised from 1.7 to 27.

In one embodiment comprising prandial insulin, the mass ratios of co-polyamino acid/pramlintide are comprised from 2.0 to 27.

In one embodiment comprising prandial insulin, the mass ratios of co-polyamino acid/pramlintide are comprised from 2.3 to 27.

In one embodiment comprising prandial insulin, the mass ratios of co-polyamino acid/pramlintide are comprised from 2.7 to 27.

In one embodiment comprising prandial insulin, the mass ratios of co-polyamino acid/pramlintide are comprised from 3.3 to 27.

In one embodiment comprising prandial insulin, the mass ratios of co-polyamino acid/pramlintide are comprised from 4.7 to 27.

In one embodiment comprising prandial insulin, the mass ratios of co-polyamino acid/pramlintide are comprised from 6.0 to 27.

Moreover, it is particularly advantageous to combine amylin, an amylin receptor agonist or an amylin analog, optionally in combination with a prandial insulin, with GLP-1, GLP-1 analogs, GLP-1 receptor agonists, which are commonly known as GLP-1 RA. This particularly makes it possible to potentiate the effect of insulin and is recommended in some types of diabetes treatment.

In one embodiment, the GLP-1, GLP-1 analogs, or GLP-1 RAs are referred to as "short-acting". The term "short-acting" denotes GLP-1, GLP-1 analogs, or GLP-1 RAs, wherein the apparent elimination half-life after subcutaneous injection in humans is less than 8 hours, in particular less than 5 hours, preferably less than 4 hours or less than 3 hours, such as for example exenatide and lixisenatide.

In one embodiment, the GLP-1, GLP-1 analogs, or GLP-1 RA are chosen in the group consisting of exenatide or Byetta® (ASTRA-ZENECA), lixisenatide or Lyxumia® (SANOFI), the analogs or derivatives thereof and the pharmaceutically acceptable salts thereof.

In one embodiment, the GLP-1, GLP-1 analog, or GLP-1 RA is exenatide or Byetta®, the analogs or derivatives thereof and the pharmaceutically acceptable salts thereof.

In one embodiment, the GLP-1, GLP-1 analog, or GLP-1 RA is lixisenatide or Lyxumia®, the analogs or derivatives thereof and the pharmaceutically acceptable salts thereof.

In one embodiment, the concentration of exenatide, the analogs or derivatives thereof and the pharmaceutically acceptable salts thereof is within a range from 0.01 to 1.0 mg per 100 U of insulin.

In one embodiment, the concentration of exenatide, the analogs or derivatives thereof and the pharmaceutically acceptable salts thereof is comprised from 0.01 to 0.5 mg per 100 U of insulin.

In one embodiment, the concentration of exenatide, the analogs or derivatives thereof and the pharmaceutically acceptable salts thereof is comprised from 0.02 to 0.4 mg per 100 U of insulin.

In one embodiment, the concentration of exenatide, the analogs or derivatives thereof and the pharmaceutically acceptable salts thereof is comprised from 0.03 to 0.3 mg per 100 U of insulin.

In one embodiment, the concentration of exenatide, the analogs or derivatives thereof and the pharmaceutically acceptable salts thereof is comprised from 0.04 to 0.2 mg per 100 U of insulin.

In one embodiment, the concentration of exenatide, the analogs or derivatives thereof and the pharmaceutically acceptable salts thereof is comprised from 0.04 to 0.15 mg per 100 U of insulin.

In one embodiment, the concentration of lixisenatide, the analogs or derivatives thereof and the pharmaceutically acceptable salts thereof is within a range from 0.01 to 1 mg per 100 U of insulin.

In one embodiment, the concentration of lixisenatide, the analogs or derivatives thereof and the pharmaceutically acceptable salts thereof is comprised from 0.01 to 0.5 mg per 100 U of insulin.

In one embodiment, the concentration of lixisenatide, the analogs or derivatives thereof and the pharmaceutically acceptable salts thereof is comprised from 0.02 to 0.4 mg per 100 U of insulin.

In one embodiment, the concentration of lixisenatide, the analogs or derivatives thereof and the pharmaceutically acceptable salts thereof is comprised from 0.03 to 0.3 mg per 100 U of insulin.

In one embodiment, the concentration of lixisenatide, the analogs or derivatives thereof and the pharmaceutically acceptable salts thereof is comprised from 0.04 to 0.2 mg per 100 U of insulin.

In one embodiment, the concentration of lixisenatide, the analogs or derivatives thereof and the pharmaceutically acceptable salts thereof is comprised from 0.04 to 0.15 mg per 100 U of insulin.

In one embodiment, the compositions according to the invention are produced by mixing amylin solutions and commercial solutions of GLP-1, GLP-1 analog or GLP-1 RA receptor agonists in volume ratios within a range of 10:90 to 90:10 in the presence of a co-polyamino acid.

The invention also relates to compositions further comprising ionic species, said ionic species being suitable for improving the stability of the compositions.

The invention also relates to the use of ionic species chosen in the group of anions, cations and/or zwitterions for improving the physicochemical stability of the compositions.

In one embodiment, the ionic species comprise less than 10 carbon atoms.

Said ionic species are chosen in the group of anions, cations and/or zwitterions. The term zwitterion denotes a species bearing at least one positive charge and at least one negative charge on two non-adjacent atoms.

Said ionic species are used alone or in a mixture and preferably in a mixture.

In one embodiment, the anions are chosen among organic anions.

In one embodiment, the organic anions comprise less than 10 carbon atoms.

In one embodiment, the organic anions are chosen in the group consisting of acetate, citrate and succinate In one embodiment, the anions are chosen among inorganic anions.

In one embodiment, the inorganic anions are chosen in the group consisting of sulfates, phosphates and halides, particularly chlorides.

In one embodiment, the cations are chosen among organic cations.

In one embodiment, the organic cations comprise less than 10 carbon atoms.

In one embodiment, the organic cations are chosen in the group consisting of ammoniums, for example 2-Amino-2-(hydroxymethyl)propane-1,3-diol where the amine is in ammonium form.

In one embodiment, the cations are chosen among inorganic cations.

In one embodiment, the inorganic cations are chosen in the group consisting of zinc, in particular Zn2+ and alkali metals, in particular Na+ and K+, In one embodiment, the zwitterions are chosen among organic zwitterions.

In one embodiment, the organic zwitterions are chosen among amino acids.

In one embodiment, the amino acids are chosen among aliphatic amino acids in the group consisting of glycine, alanine, valine, isoleucine and leucine.

In one embodiment, the amino acids are chosen among cyclic amino acids in the group consisting of proline.

In one embodiment, the amino acids are chosen among hydroxylated amino acids in the group consisting of cysteine, serine, threonine, and methionine.

In one embodiment, the amino acids are chosen among aromatic amino acids in the group consisting of phenylalanine, tyrosine and tryptophan.

In one embodiment, the amino acids are chosen among amino acids wherein the carboxyl function of the side chain is amidified in the group consisting of asparagine and glutamine.

In one embodiment, the organic zwitterions are chosen in the group consisting of amino acids having a non-charged side chain.

In one embodiment, the organic zwitterions are chosen in the group consisting of amino diacids or acidic amino acids.

In one embodiment, the amino diacids are chosen in the group consisting of glutamic acid and aspartic acid, optionally in salt form.

In one embodiment, the organic zwitterions are chosen in the group consisting of basic or so-called "cationic" amino acids.

In one embodiment, the so-called "cationic" amino acids are chosen among arginine, histidine and lysine, in particular arginine and lysine.

Most particularly, the zwitterions comprise as many negative charges as positive charges and therefore a nil overall charge at the isoelectric point and/or at a pH comprised from 6 to 8.

Said ionic species are introduced into the compositions in salt form. The introduction thereof may be made in solid form prior to placing in solution in the compositions, or in solution form, in particular concentrated solution.

For example, the inorganic cations are added in the form of salts chosen among sodium chloride, zinc chloride, sodium phosphate, sodium sulfate, etc.

For example, the organic cations are added in the form of salts chosen among sodium or potassium citrate, sodium acetate.

For example, the amino acids are added in the form of salts chosen among arginine hydrochloride, histidine hydrochloride or in the non-salified form such as for example histidine, arginine.

In one embodiment, the total molar concentration of ionic species in the composition is greater than or equal to 10 mM.

In one embodiment, the total molar concentration of ionic species in the composition is greater than or equal to 20 mM.

In one embodiment, the total molar concentration of ionic species in the composition is greater than or equal to 30 mM.

In one embodiment, the total molar concentration of ionic species in the composition is greater than or equal to 50 mM.

In one embodiment, the total molar concentration of ionic species in the composition is greater than or equal to 75 mM.

In one embodiment, the total molar concentration of ionic species in the composition is greater than or equal to 100 mM.

In one embodiment, the total molar concentration of ionic species in the composition is greater than or equal to 200 mM.

In one embodiment, the total molar concentration of ionic species in the composition is greater than or equal to 300 mM.

In one embodiment, the total molar concentration of ionic species in the composition is greater than or equal to 500 mM.

In one embodiment, the total molar concentration of ionic species in the composition is greater than or equal to 600 mM.

In one embodiment, the total molar concentration of ionic species in the composition is greater than or equal to 700 mM.

In one embodiment, the total molar concentration of ionic species in the composition is greater than or equal to 800 mM.

In one embodiment, the total molar concentration of ionic species in the composition is greater than or equal to 900 mM.

In one embodiment, the total molar concentration of ionic species in the composition is less than or equal to 1000 mM.

In one embodiment, the total molar concentration of ionic species in the composition is less than or equal to 1500 mM.

In one embodiment, the total molar concentration of ionic species in the composition is less than or equal to 1200 mM.

In one embodiment, the total molar concentration of ionic species in the composition is less than or equal to 1000 mM.

In one embodiment, the total molar concentration of ionic species in the composition is less than or equal to 900 mM.

In one embodiment, the total molar concentration of ionic species in the composition is less than or equal to 800 mM.

In one embodiment, the total molar concentration of ionic species in the composition is less than or equal to 700 mM.

In one embodiment, the total molar concentration of ionic species in the composition is less than or equal to 600 mM.

In one embodiment, the total molar concentration of ionic species in the composition is less than or equal to 500 mM.

In one embodiment, the total molar concentration of ionic species in the composition is less than or equal to 400 mM.

In one embodiment, the total molar concentration of ionic species in the composition is less than or equal to 300 mM.

In one embodiment, the total molar concentration of ionic species in the composition is less than or equal to 200 mM.

In one embodiment, the total molar concentration of ionic species in the composition is less than or equal to 100 mM.

In one embodiment, the total molar concentration of ionic species in the composition is comprised from 10 to 1000 mM.

In one embodiment, the total molar concentration of ionic species in the composition is comprised from 20 to 1000 mM.

In one embodiment, the total molar concentration of ionic species in the composition is comprised from 30 to 1000 mM.

In one embodiment, the total molar concentration of ionic species in the composition is comprised from 50 to 1000 mM.

In one embodiment, the total molar concentration of ionic species in the composition is comprised from 75 to 1000 mM.

In one embodiment, the total molar concentration of ionic species in the composition is comprised from 100 to 1000 mM.

In one embodiment, the total molar concentration of ionic species in the composition is comprised from 200 to 1000 mM.

In one embodiment, the total molar concentration of ionic species in the composition is comprised from 300 to 1000 mM.

In one embodiment, the total molar concentration of ionic species in the composition is comprised from 400 to 1000 mM.

In one embodiment, the total molar concentration of ionic species in the composition is comprised from 500 to 1000 mM.

In one embodiment, the total molar concentration of ionic species in the composition is comprised from 600 to 1000 mM.

In one embodiment, the total molar concentration of ionic species in the composition is comprised from 10 to 900 mM.

In one embodiment, the total molar concentration of ionic species in the composition is comprised from 20 to 900 mM.

In one embodiment, the total molar concentration of ionic species in the composition is comprised from 30 to 900 mM.

In one embodiment, the total molar concentration of ionic species in the composition is comprised from 50 to 900 mM.

In one embodiment, the total molar concentration of ionic species in the composition is comprised from 75 to 900 mM.

In one embodiment, the total molar concentration of ionic species in the composition is comprised from 100 to 900 mM.

In one embodiment, the total molar concentration of ionic species in the composition is comprised from 200 to 900 mM.

In one embodiment, the total molar concentration of ionic species in the composition is comprised from 300 to 900 mM.

In one embodiment, the total molar concentration of ionic species in the composition is comprised from 400 to 900 mM.

In one embodiment, the total molar concentration of ionic species in the composition is comprised from 500 to 900 mM.

In one embodiment, the total molar concentration of ionic species in the composition is comprised from 600 to 900 mM.

In one embodiment, the total molar concentration of ionic species in the composition is comprised from 10 to 800 mM.

In one embodiment, the total molar concentration of ionic species in the composition is comprised from 20 to 800 mM.

In one embodiment, the total molar concentration of ionic species in the composition is comprised from 30 to 800 mM.

In one embodiment, the total molar concentration of ionic species in the composition is comprised from 50 to 800 mM.

In one embodiment, the total molar concentration of ionic species in the composition is comprised from 75 to 800 mM.

In one embodiment, the total molar concentration of ionic species in the composition is comprised from 100 to 800 mM.

In one embodiment, the total molar concentration of ionic species in the composition is comprised from 200 to 800 mM.

In one embodiment, the total molar concentration of ionic species in the composition is comprised from 300 to 800 mM.

In one embodiment, the total molar concentration of ionic species in the composition is comprised from 400 to 800 mM.

In one embodiment, the total molar concentration of ionic species in the composition is comprised from 500 to 800 mM.

In one embodiment, the total molar concentration of ionic species in the composition is comprised from 600 to 800 mM.

In one embodiment, the total molar concentration of ionic species in the composition is comprised from 10 to 700 mM.

In one embodiment, the total molar concentration of ionic species in the composition is comprised from 20 to 700 mM.

In one embodiment, the total molar concentration of ionic species in the composition is comprised from 30 to 700 mM.

In one embodiment, the total molar concentration of ionic species in the composition is comprised from 50 to 700 mM.

In one embodiment, the total molar concentration of ionic species in the composition is comprised from 75 to 700 mM.

In one embodiment, the total molar concentration of ionic species in the composition is comprised from 100 to 700 mM.

In one embodiment, the total molar concentration of ionic species in the composition is comprised from 200 to 700 mM.

In one embodiment, the total molar concentration of ionic species in the composition is comprised from 300 to 700 mM.

In one embodiment, the total molar concentration of ionic species in the composition is comprised from 400 to 700 mM.

In one embodiment, the total molar concentration of ionic species in the composition is comprised from 500 to 700 mM.

In one embodiment, the total molar concentration of ionic species in the composition is comprised from 600 to 700 mM.

In one embodiment, the total molar concentration of ionic species in the composition is comprised from 10 to 600 mM.

In one embodiment, the total molar concentration of ionic species in the composition is comprised from 20 to 600 mM.

In one embodiment, the total molar concentration of ionic species in the composition is comprised from 30 to 600 mM.

In one embodiment, the total molar concentration of ionic species in the composition is comprised from 50 to 600 mM.

In one embodiment, the total molar concentration of ionic species in the composition is comprised from 75 to 600 mM.

In one embodiment, the total molar concentration of ionic species in the composition is comprised from 100 to 600 mM.

In one embodiment, the total molar concentration of ionic species in the composition is comprised from 200 to 600 mM.

In one embodiment, the total molar concentration of ionic species in the composition is comprised from 300 to 600 mM.

In one embodiment, the total molar concentration of ionic species in the composition is comprised from 400 to 600 mM.

In one embodiment, the total molar concentration of ionic species in the composition is comprised from 500 to 600 mM.

In one embodiment, the total molar concentration of ionic species in the composition is comprised from 10 to 500 mM.

In one embodiment, the total molar concentration of ionic species in the composition is comprised from 20 to 500 mM.

In one embodiment, the total molar concentration of ionic species in the composition is comprised from 30 to 500 mM.

In one embodiment, the total molar concentration of ionic species in the composition is comprised from 50 to 500 mM.

In one embodiment, the total molar concentration of ionic species in the composition is comprised from 75 to 500 mM.

In one embodiment, the total molar concentration of ionic species in the composition is comprised from 100 to 500 mM.

In one embodiment, the total molar concentration of ionic species in the composition is comprised from 200 to 500 mM.

In one embodiment, the total molar concentration of ionic species in the composition is comprised from 300 to 500 mM.

In one embodiment, the total molar concentration of ionic species in the composition is comprised from 400 to 500 mM.

In one embodiment, the total molar concentration of ionic species in the composition is comprised from 10 to 400 mM.

In one embodiment, the total molar concentration of ionic species in the composition is comprised from 20 to 400 mM.

In one embodiment, the total molar concentration of ionic species in the composition is comprised from 30 to 400 mM.

In one embodiment, the total molar concentration of ionic species in the composition is comprised from 50 to 400 mM.

In one embodiment, the total molar concentration of ionic species in the composition is comprised from 75 to 400 mM.

In one embodiment, the total molar concentration of ionic species in the composition is comprised from 100 to 400 mM.

In one embodiment, the total molar concentration of ionic species in the composition is comprised from 200 to 400 mM.

In one embodiment, the total molar concentration of ionic species in the composition is comprised from 300 to 400 mM.

In one embodiment, the total molar concentration of ionic species in the composition is comprised from 10 to 300 mM.

In one embodiment, the total molar concentration of ionic species in the composition is comprised from 20 to 300 mM.

In one embodiment, the total molar concentration of ionic species in the composition is comprised from 30 to 300 mM.

In one embodiment, the total molar concentration of ionic species in the composition is comprised from 50 to 300 mM.

In one embodiment, the total molar concentration of ionic species in the composition is comprised from 75 to 300 mM.

In one embodiment, the total molar concentration of ionic species in the composition is comprised from 100 to 300 mM.

In one embodiment, the total molar concentration of ionic species in the composition is comprised from 200 to 300 mM.

In one embodiment, the total molar concentration of ionic species in the composition is comprised from 10 to 200 mM.

In one embodiment, the total molar concentration of ionic species in the composition is comprised from 20 to 200 mM.

In one embodiment, the total molar concentration of ionic species in the composition is comprised from 30 to 200 mM.

In one embodiment, the total molar concentration of ionic species in the composition is comprised from 50 to 200 mM.

In one embodiment, the total molar concentration of ionic species in the composition is comprised from 75 to 200 mM.

In one embodiment, the total molar concentration of ionic species in the composition is comprised from 100 to 200 mM.

In one embodiment, the total molar concentration of ionic species in the composition is comprised from 10 to 100 mM.

In one embodiment, the total molar concentration of ionic species in the composition is comprised from 20 to 100 mM.

In one embodiment, the total molar concentration of ionic species in the composition is comprised from 30 to 100 mM.

In one embodiment, the total molar concentration of ionic species in the composition is comprised from 50 to 100 mM.

In one embodiment, the total molar concentration of ionic species in the composition is comprised from 75 to 100 mM.

In one embodiment, the total molar concentration of ionic species in the composition is comprised from 10 to 75 mM.

In one embodiment, the total molar concentration of ionic species in the composition is comprised from 20 to 75 mM.

In one embodiment, the total molar concentration of ionic species in the composition is comprised from 30 to 75 mM.

In one embodiment, the total molar concentration of ionic species in the composition is comprised from 50 to 75 mM.

In one embodiment, the total molar concentration of ionic species in the composition is comprised from 10 to 50 mM.

In one embodiment, the total molar concentration of ionic species in the composition is comprised from 20 to 50 mM.

In one embodiment, the total molar concentration of ionic species in the composition is comprised from 30 to 50 mM.

In one embodiment, said ionic species are present at a concentration ranging from 5 to 400 mM.

In one embodiment, said ionic species are present at a concentration ranging from 5 to 300 mM.

In one embodiment, said ionic species are present at a concentration ranging from 5 to 200 mM.

In one embodiment, said ionic species are present at a concentration ranging from 5 to 100 mM.

In one embodiment, said ionic species are present at a concentration ranging from 5 to 75 mM.

In one embodiment, said ionic species are present at a concentration ranging from 5 to 50 mM.

In one embodiment, said ionic species are present at a concentration ranging from 5 to 25 mM.

In one embodiment, said ionic species are present at a concentration ranging from 5 to 20 mM.

In one embodiment, said ionic species are present at a concentration ranging from 5 to 10 mM.

In one embodiment, said ionic species are present at a concentration ranging from 10 to 400 mM.

In one embodiment, said ionic species are present at a concentration ranging from 10 to 300 mM.

In one embodiment, said ionic species are present at a concentration ranging from 10 to 200 mM.

In one embodiment, said ionic species are present at a concentration ranging from 10 to 100 mM.

In one embodiment, said ionic species are present at a concentration ranging from 10 to 75 mM.

In one embodiment, said ionic species are present at a concentration ranging from 10 to 50 mM.

In one embodiment, said ionic species are present at a concentration ranging from 10 to 25 mM.

In one embodiment, said ionic species are present at a concentration ranging from 10 to 20 mM.

In one embodiment, said ionic species are present at a concentration ranging from 20 to 300 mM.

In one embodiment, said ionic species are present at a concentration ranging from 20 to 200 mM.

In one embodiment, said ionic species are present at a concentration ranging from 20 to 100 mM.

In one embodiment, said ionic species are present at a concentration ranging from 20 to 75 mM.

In one embodiment, said ionic species are present at a concentration ranging from 20 to 50 mM.

In one embodiment, said ionic species are present at a concentration ranging from 20 to 25 mM.

In one embodiment, said ionic species are present at a concentration ranging from 50 to 300 mM.

In one embodiment, said ionic species are present at a concentration ranging from 50 to 200 mM.

In one embodiment, said ionic species are present at a concentration ranging from 50 to 100 mM.

In one embodiment, said ionic species are present at a concentration ranging from 50 to 75 mM.

In the case of inorganic cations and in particular of $Zn^{2+}$, the molar concentration thereof in the composition may be from 0.25 to 20 mM, in particular from 0.25 to 10 mM or from 0.25 to 5 mM.

In one embodiment, the composition comprises zinc.

In one embodiment, the composition comprises from 0.2 to 2 mM of zinc.

In one embodiment, the composition comprises NaCl.

In one embodiment, the composition comprises from 10 to 250 mM of NaCl.

In one embodiment, the composition comprises from 15 to 200 mM of NaCl.

In one embodiment, the composition comprises from 20 to 150 mM of NaCl.

In one embodiment, the composition comprises from 25 to 100 mM of NaCl.

In one embodiment, the compositions according to the invention further comprise zinc salts at a concentration from 0 to 500 µM per 100 U of insulin.

In one embodiment, the compositions according to the invention further comprise zinc salts at a concentration from 0 to 400 µM per 100 U of insulin.

In one embodiment, the compositions according to the invention further comprise zinc salts at a concentration from 0 to 300 µM per 100 U of insulin.

In one embodiment, the compositions according to the invention further comprise zinc salts at a concentration from 0 to 200 µM per 100 U of insulin.

In one embodiment, the compositions according to the invention further comprise zinc salts at a concentration from 0 to 100 µM per 100 U of insulin.

In one embodiment, the compositions according to the invention further comprise buffers.

In one embodiment, the compositions according to the invention comprise buffers at concentrations from 0 to 100 mM.

In one embodiment, the compositions according to the invention comprise buffers at concentrations from 15 to 50 mM.

In one embodiment, the compositions according to the invention comprise a buffer chosen in the group consisting of a phosphate buffer, Tris (trishydroxymethylaminomethane) and sodium citrate.

In one embodiment, the buffer is sodium phosphate.

In one embodiment, the buffer is Tris (trishydroxymethylaminomethane).

In one embodiment, the buffer is sodium citrate.

In one embodiment, the compositions according to the invention further comprise preservatives.

In one embodiment, the preservatives are chosen in the group consisting of m-cresol and phenol, alone or in a mixture.

In one embodiment, the concentration of the preservatives is comprised from 10 to 50 mM.

In one embodiment, the concentration of the preservatives is comprised from 10 to 40 mM.

In one embodiment, the compositions according to the invention further comprise a surfactant.

In one embodiment, the surfactant is chosen in the group consisting of propylene glycol and polysorbate.

The compositions according to the invention may further comprise additives such as tonicity agents.

In one embodiment, the tonicity agents are chosen in the group consisting of glycerin, sodium chloride, mannitol and glycine.

The compositions according to the invention may further comprise any excipients complying with the pharmacopeias and compatible with insulins used at customary concentrations.

The invention also relates to a pharmaceutical formulation according to the invention, characterized in that it is obtained by drying and/or freeze-drying.

In the case of local and systemic releases, the modes of administration envisaged are by the intravenous, subcutaneous, intradermal or intramuscular route.

The transdermal, oral, nasal, vaginal, ocular, buccal, pulmonary administration routes are also envisaged.

The invention also relates to an implantable or transportable pump comprising a composition according to the invention.

The invention also relates to the use of a composition according to the invention intended to be placed in an implantable or transportable pump.

The invention also relates to unit-dose formulations at pH comprised from 6.0 to 8.0 comprising amylin, an amylin receptor agonist or an amylin analog and a co-polyamino acid according to the invention.

The invention also relates to unit-dose formulations at pH comprised from 6.0 to 8.0 comprising amylin, an amylin receptor agonist or an amylin analog and a co-polyamino acid according to the invention and a GLP-1, a GLP-1 analog or a GLP-1 RA, as defined above.

The invention also relates to unit-dose formulations at pH comprised from 6.6 to 7.8 comprising amylin, an amylin receptor agonist or an amylin analog and a co-polyamino acid according to the invention.

The invention also relates to unit-dose formulations at pH comprised from 6.6 to 7.8 comprising amylin, an amylin receptor agonist or an amylin analog and a co-polyamino acid according to the invention and a prandial insulin, as defined above.

The invention also relates to unit-dose formulations at pH comprised from 6.6 to 7.6 comprising amylin, an amylin receptor agonist or an amylin analog and a co-polyamino acid according to the invention.

The invention also relates to unit-dose formulations at pH comprised from 6.6 to 7.6 comprising amylin, an amylin receptor agonist or an amylin analog and a co-polyamino acid according to the invention and a prandial insulin, as defined above.

In one embodiment, the single-dose formulations further comprise a co-polyamino acid as defined above.

In one embodiment, the formulations are in the form of an injectable solution.

The preparation of a composition according to the invention offers the advantage of being suitable for being carried out by merely mixing an aqueous solution of amylin or an amylin analog, and a co-polyamino acid bearing carboxylate charges and at least one hydrophobic radical according to the invention, in aqueous solution or in freeze-dried form. If required, the pH of the preparation is adjusted to pH comprised from 6 to 8.

The preparation of a composition according to the invention offers the advantage of being suitable for being carried out by merely mixing an aqueous solution of amylin, an amylin receptor agonist or an amylin analog, prandial insulin, and a co-polyamino acid bearing carboxylate charges and at least one hydrophobic radical according to the invention, in aqueous solution or in freeze-dried form. If required, the pH of the preparation is adjusted to pH comprised from 6 to 8.

In one embodiment, the mixture of prandial insulin and co-polyamino acid is concentrated by ultrafiltration.

If required, the composition of the mixture is adjusted with excipients such as glycerin, m-cresol, zinc chloride, and polysorbate (Tween®) by adding concentrated solutions of these excipients in the mixture. If required, the pH of the preparation is adjusted to pH comprised from 6 to 8.

In one embodiment, the compositions are characterized in that said compositions have a stability measured by ThT greater than that of a reference composition comprising amylin, an amylin receptor agonist or an amylin agonist but not comprising co-polyamino acid bearing carboxylate charges and hydrophobic radicals -Hy.

In one embodiment, the compositions are characterized in that said compositions have a stability measured by ThT greater than that of a reference composition comprising amylin, an amylin receptor agonist or an amylin agonist in combination with an insulin but not comprising co-polyamino acid bearing carboxylate charges and hydrophobic radicals -Hy.

In one embodiment, the compositions are characterized in that said compositions have a stability measured by ThT greater than that of a reference composition comprising amylin, an amylin receptor agonist or an amylin agonist in combination with a GLP-1, a GLP-1 analog or a GLP-1 receptor agonist, but not comprising co-polyamino acid bearing carboxylate charges and hydrophobic radicals Hy.

In one embodiment, the compositions are characterized in that said compositions have a stability measured by ThT greater than that of a reference composition comprising amylin, an amylin receptor agonist or an amylin agonist in combination with an insulin and a GLP-1, a GLP-1 analog or a GLP-1 receptor agonist, but not comprising co-polyamino acid bearing carboxylate charges and hydrophobic radicals Hy.

The invention also relates to a use of a co-polyamino acid bearing carboxylate charges and hydrophobic radicals Hy for stabilizing a composition comprising amylin, an amylin receptor agonist or an amylin analog.

The invention also relates to a use of a co-polyamino acid bearing carboxylate charges and hydrophobic radicals Hy for stabilizing a composition comprising amylin, an amylin receptor agonist or an amylin analog and a prandial insulin, and optionally a GLP-1, a GLP-1 analog, or a GLP-1 receptor agonist.

The invention also relates to a method for stabilizing a composition comprising amylin, an amylin receptor agonist or an amylin analog or a method for stabilizing a composition comprising amylin, an amylin receptor agonist or an amylin analog and a prandial insulin, and optionally a GLP-1, a GLP-1 analog, or a GLP-1 receptor agonist.

The examples hereinafter illustrate, in a non-limiting manner, the invention.

Part A—Synthesis of Hydrophobic Intermediate Compounds Hyd for Obtaining the Radicals -Hy.

| # | HYDROPHOBIC INTERMEDIATE COMPOUNDS |
|---|---|
| A1 | (structure: proline with N-acyl chain terminating in CH$_3$) |

-continued
| # | HYDROPHOBIC INTERMEDIATE COMPOUNDS |
|---|---|
| A2 | 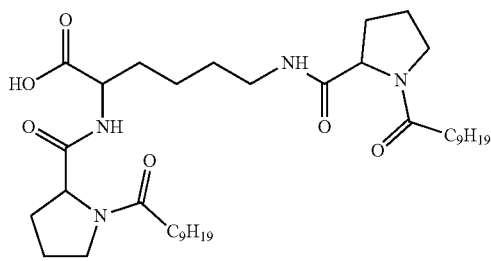 |
| A3 | 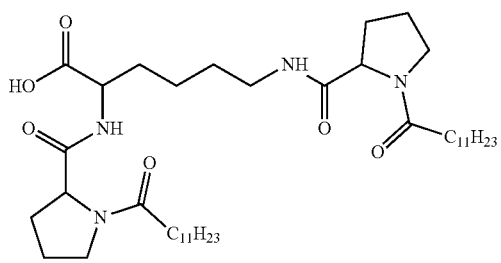 |
| A4 | 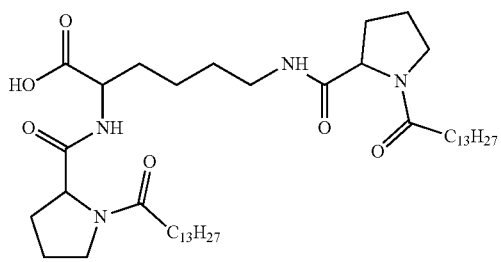 |
| A5 | 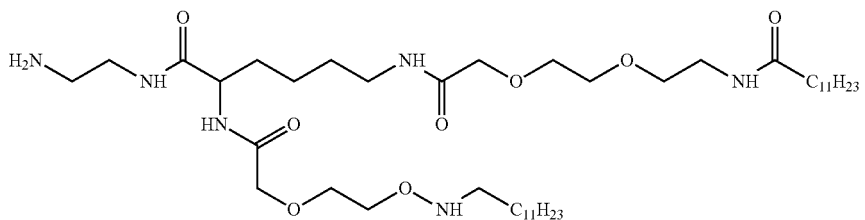 |
| A6 | 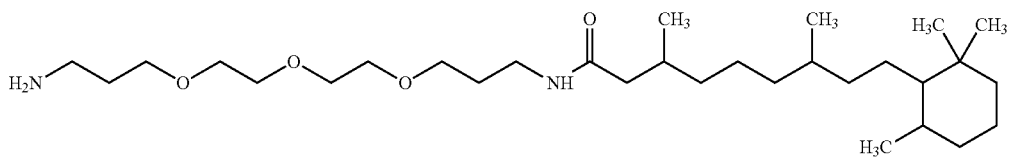 [SMILES: CC(CCCC(C)CC(=O)NCCCOCCOCCOCCCN)CCC1C(C)CCCC1(C)C] |

| # | HYDROPHOBIC INTERMEDIATE COMPOUNDS |
|---|---|
| A7 | 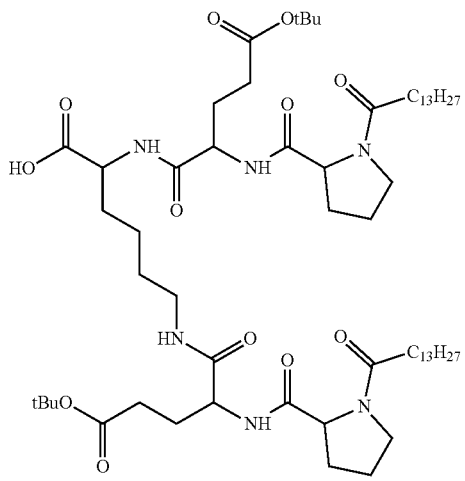 |
| A8 | 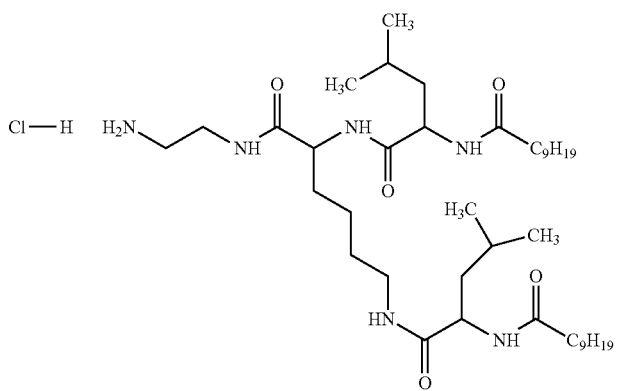 |
| A9 | 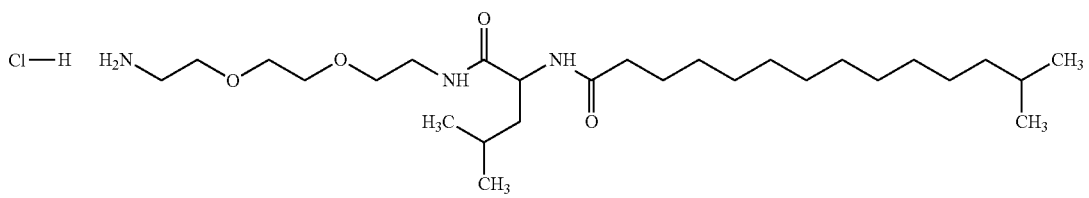 [SMILES: Cl ; CC(C)CCCCCCCCCCCC(=O)NC(CC(C)C)C(=O)NCCOCCOCCN] |

| # | HYDROPHOBIC INTERMEDIATE COMPOUNDS |
|---|---|
| A10 | 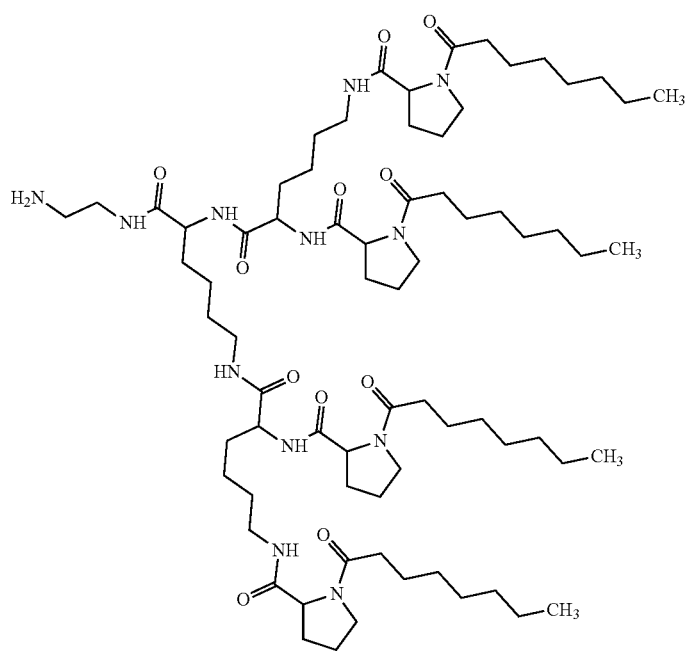 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |
| A11 | 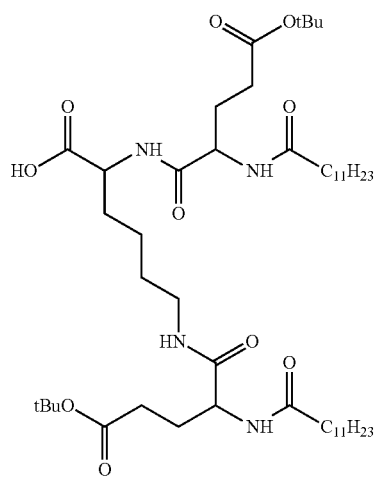 |
| A12 | 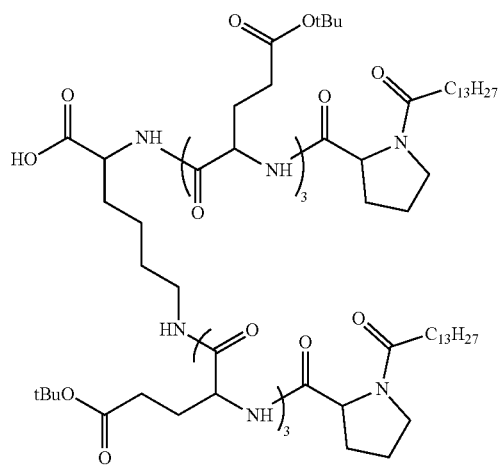 |

| # | HYDROPHOBIC INTERMEDIATE COMPOUNDS |
|---|---|
| A14 | 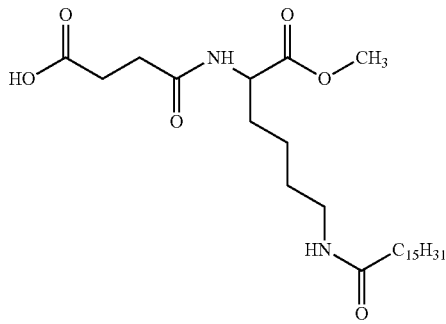 |
| A15 | 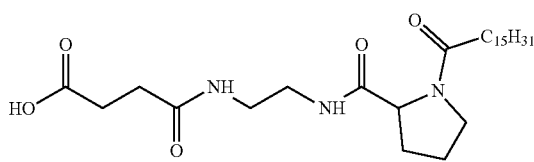 |
| A16 | 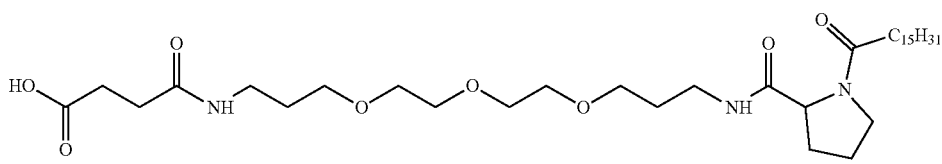 |
| A17 | 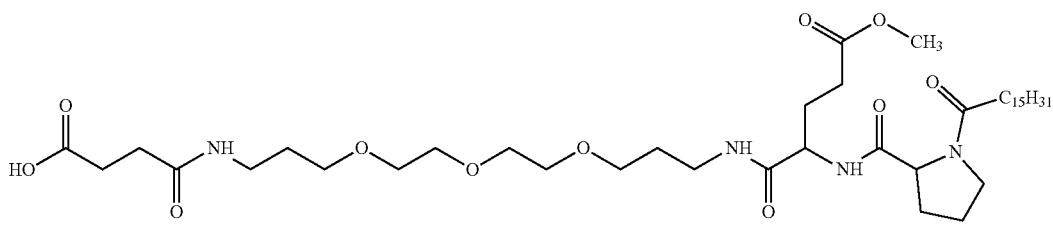 |
| A18 | 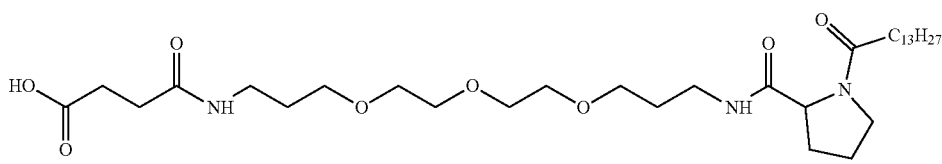 |
| A19 | 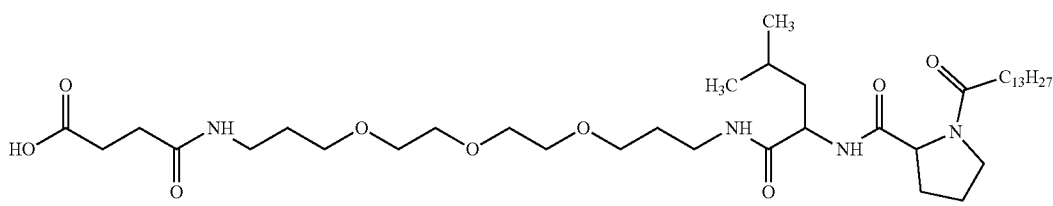 |
| A21 | 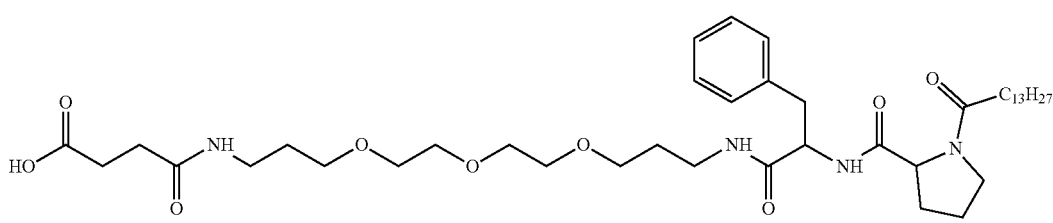 |

-continued

| # | HYDROPHOBIC INTERMEDIATE COMPOUNDS |
|---|---|
| A22 | [structure] |
| A23 | [structure] |
| A26 | [structure] |
| A27 | [structure] |

EXAMPLE A1

Molecule A1

To a solution of L-proline (300.40 g, 2.61 mol) in 2 N aqueous sodium hydroxide (1.63 L) at 0° C. is added slowly over 1 h myristoyl chloride (322 g, 1.30 mol) in solution in dichloromethane (DCM, 1.63 L). At the end of the addition, the reaction medium is returned to 20° C. in 3 h, then stirred for a further 2 h. The mixture is cooled to 0° C. then a 37% HCl aqueous solution (215 mL) is added in 15 min. The reaction medium is stirred for 3 h from 0° C. to 20° C., then cooled to 3° C. 37% HCl (213 mL) is added in 15 min and the mixture is stirred for 1 h from 0° C. to 20° C. The organic phase is separated, washed with a 10% HCl aqueous solution (3×430 mL), an aqueous solution saturated with NaCl (430 mL), dried on $Na_2SO_4$, filtered on cotton then concentrated at reduced pressure. The residue is solubilized in heptane (1.31 L) at 50° C., then the solution is progressively returned to ambient temperature. After priming crystallization using a glass rod, the medium is once again heated to 40° C. for 30 min then returned to ambient temperature for 4 h. A white solid of molecule A1 is obtained after filtration on a sintered filter, washing with heptane (2×350 mL) and drying at reduced pressure.

Yield: 410 g (97%)

$^1H$ NMR $CDCl_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7; (calculated ($[M+H]^+$): 326.3; ($[2M+H]^+$): 651.6).

EXAMPLE A2

Molecule A2

Molecule 1: Product obtained by reacting decanoyl chloride and L-proline.

By means of a similar method to that used for the preparation of molecule A1 and applied to decanoyl chloride (75.0 g, 393.27 mmol) and to L-proline (90.55 g, 786.53 mmol), a colorless oil of molecule 1 is obtained after washing the organic phase with a 10% HCl aqueous solution (3×125 mL), an aqueous solution saturated with NaCl (125 mL), drying on Na2SO4, filtration on cotton followed by concentration at reduced pressure.

Yield: 104.64 g (99%)

$^1H$ NMR $CDCl_3$, ppm): 0.86 (3H); 1.10-1.51 (12H); 1.56-1.80 (2H); 1.83-2.46 (6H); 3.42-3.66 (2H); 4.37-4.41 (0.1H); 4.53-4.60 (0.9H); 10.12 (1H).

LC/MS (ESI): 270.1; (calculated ($[M+H]^+$): 270.2).

Molecule A2

To a solution of molecule 1 (90.0 g, 334.09 mmol) in THF (600 mL) at 0° C. are added successively N-hydroxysuccinimide (NHS, 40.4 g, 350.80 mmol) followed by dicyclohexylcarbodiimide (DCC, 72.38 g, 350.80 mmol) in solution in THF (60 mL). After 16 h of stirring at ambient temperature, the reaction medium is filtered and introduced onto a solution of L-lysine hydrochloride (30.51 g, 167.05 mmol) and N,N-diisopropylethylamine (DIPEA, 97.16 g, 751.71 mmol) in water (66 mL) and the mixture is stirred for 48 h at 20° C. After concentration at reduced pressure, water (360 mL) is added and the mixture obtained is treated by successive addition of ethyl acetate (AcOEt, 500 mL) followed by a 5% Na$_2$CO$_3$ aqueous solution (1 L). The aqueous phase is then washed once again with AcOEt (200 mL), acidified by adding a 6 N HCl aqueous solution and the product is extracted with dichloromethane (DCM, 3×250 mL). The organic phase is dried on Na$_2$SO$_4$, filtered and concentrated under vacuum. The white solid obtained after crystallization in AcOEt is solubilized in DCM (400 mL), the organic phase is washed with a 1 N HCl aqueous solution (200 mL) followed by an aqueous solution saturated with NaCl (200 mL), dried on Na$_2$SO$_4$, filtered and concentrated under vacuum. A white solid of molecule A2 is obtained after crystallization in AcOEt.

Yield: 75.90 g (70%)

$^1$H NMR (DMSO-d6, ppm): 0.85 (6H); 1.10-2.04 (42H); 2.07-2.30 (4H); 2.92-3.08 (2H); 3.28-3.57 (4H); 4.07-4.28 (2H); 4.32-4.40 (1H); 7.66-7.73 (0.6H); 7.96-8.09 (1H); 8.27 (0.4H); 12.51 (1H).

LC/MS (ESI): 649.5 (calculated ([M+H]$^+$): 649.5).

EXAMPLE A3

Molecule A3

Molecule 2: Product obtained by reacting lauroyl chloride and L-Proline.

By means of a similar method to that used for the preparation of molecule A1 and applied to lauroyl chloride (27.42 g, 685.67 mmol) and to L-proline (60.0 g, 247.27 mmol), a white solid of molecule 2 is obtained.

Yield: 78.35 g (96%)

$^1$H NMR CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI): 298.1 (calculated ([M+H]$^+$): 298.2).

Molecule A3:

By means of a similar method to that used for the preparation of molecule A2 applied to molecule 2 (42.49 g, 142.86 mmol) and to L-lysine hydrochloride (13.7 g, 75.0 mmol), a white solid of molecule A3 is obtained after crystallization in acetone.

Yield: 30.17 g (60%)

$^1$H NMR (DMSO-d6, ppm): 0.86 (6H); 1.07-2.05 (50H); 2.08-2.30 (4H); 2.93-3.09 (2H); 3.28-3.57 (4H); 4.08-4.29 (2H); 4.33-4.41 (1H); 7.70 (0.6H); 7.97-8.07 (1H); 8.28 (0.4H); 12.52 (1H).

LC/MS (ESI): 705.6; (calculated ([M+H]$^+$): 705.6).

EXAMPLE A4

Molecule A4

By means of a similar method to that used for the preparation of molecule A2 applied to molecule A1 (200.0 g, 614.44 mmol) and to L-lysine hydrochloride (56.11 g, 307.22 mmol), a white solid of molecule A4 is obtained after crystallization in ethyl acetate.

Yield: 176.0 g (95%)

$^1$H NMR (DMSO-d$_6$, ppm): 0.85 (6H); 1.08-1.51 (48H); 1.53-2.04 (10H); 2.08-2.30 (4H); 2.93-3.09 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+H]$^+$): 761.6).

EXAMPLE A5

Molecule A5

Molecule 3: Product obtained by reacting Fmoc-Lys (Fmoc)-OH and 2-Cl-trityl chloride resin.

To a suspension of Fmoc-Lys(Fmoc)-OH (7.32 g, 12.40 mmol) in DCM (60 mL) at ambient temperature is added DIPEA (4.32 mL, 24.80 mmol). After complete solubilization (10 min), the solution obtained is poured onto 2-Cl-trityl chloride resin (100-200 mesh, 1% DVB, 1.24 mmol/g) (4.00 g, 4.96 mmol) previously washed with DCM, in a reaction vessel suitable for solid substrate peptide synthesis. After 2 h of stirring at ambient temperature, HPLC grade methanol (0.8 mL/g resin, 3.2 mL) is added and the medium is stirred at ambient temperature for 15 min. The resin is filtered, washed successively with DCM (3×60 mL), DMF (2×60 mL), DCM (2×60 mL), isopropanol (1×60 mL) and DCM (3×60 mL).

Molecule 4: Product obtained by reacting molecule 3 and an 80:20 DMF/piperidine mixture.

Molecule 3, previously washed with DMF, is treated with an 80:20 DMF/piperidine mixture (60 mL). After 30 min of stirring at ambient temperature, the resin is filtered, washed successively with DMF (3×60 mL), isopropanol (1×60 mL) and DCM (3×60 mL).

Molecule 5: Product Obtained by Reacting Molecule 4 and 8-(9-Fluorenylmethyloxycarbonyl-amino)-3,6-dioxaoctanoic acid (Fmoc-O2Oc-OH).

To a suspension of Fmoc-O2Oc-OH (9.56 g, 24.80 mmol) and 1-[bis(dimethylamino)methylene]-1H-1,2,3-triazolo[4,5-b]pyridinium 3-oxide hexafluorophosphate (HATU, 9.43 g, 24.80 mmol) in a 1:1 DMF/DCM mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and DCM (3×60 mL).

Molecule 6: Product obtained by reacting molecule 5 and an 80:20 DMF/piperidine mixture.

By Means of a similar method to that used for molecule 4 applied to molecule 5, molecule 6 is obtained.

Molecule 7: Product obtained by reacting molecule 6 and lauric acid.

By means of a similar method to that used for molecule 5 applied to molecule 6 and to lauric acid (4.97 g, 24.80 mmol) in DMF (60 mL), molecule 7 is obtained.

Molecule 8: Product obtained by reacting molecule 7 and an 80:20 dichloromethane/1,1,1,3,3,3-hexafluoro-2-propanol (HFIP) mixture.

Molecule 7 is treated with an 80:60 dichloromethane/1,1,1,3,3,3-hexafluoro-2-propanol (HFIP) mixture (60 mL). After 20 min of stirring at ambient temperature, the resin is filtered and washed successively with dichloromethane (2×60 mL). The solvents are evaporated at reduced pressure. Two co-evaporations are then carried out on the residue with dichloromethane (60 mL) followed by diisopropylether (60 mL). A white solid of molecule 8 is obtained after recrystallization in acetonitrile.

Yield: 2.63 g (66% in 6 stages)

$^1$H NMR CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (1H); 7.38-7.54 (1H).

LC/MS (ESI): 801.6 (calculated ([M+H]$^+$): 801.6).

Molecule 9: Product obtained by reacting molecule 8 and N-Boc ethylenediamine.

To a solution of molecule 8 (2.63 g, 3.29 mmol) in chloroform (20 mL) at ambient temperature are added successively N-hydroxybenzotriazole (HOBt, 654 mg, 4.27 mmol) and N-Boc ethylenediamine (BocEDA, 580 mg, 3.62 mmol). The mixture is cooled to 0° C. then (3-dimethyl-aminopropyl)-N'-ethylcarbodiimide hydrochloride (EDC 819 mg, 4.27 mmol) is added. The reaction medium is stirred for 15 min at 0° C. followed by 18 h at ambient temperature. The organic phase is washed with an aqueous solution saturated with $NH_4Cl$ (2×10 mL), an aqueous solution saturated with $NaHCO_3$ (2×10 mL), and an aqueous solution saturated with NaCl (2×10 mL). The organic phase is dried on $Na_2SO_4$, filtered and concentrated at reduced pressure. A white solid of molecule 9 is obtained after purification by silica gel chromatography (eluent: dichloromethane, methanol).

Yield: 2.37 g (76%)

$^1$H NMR $CDCl_3$, ppm): 0.87 (6H); 1.08-1.47 (34H); 1.43 (9H); 1.48-1.70 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5

To a solution of molecule 9 (2.37 g, 2.51 mmol) in dichloromethane (50 mL) at ambient temperature is added a 4 M HCl solution in dioxane (6.3 mL) then the medium is stirred for 2 h at ambient temperature. After concentration at reduced pressure, the residue is solubilized in dichloromethane (50 mL) then washed with a 1 N NaOH aqueous solution (2×12.5 mL) and an aqueous solution saturated with NaCl (25 mL). The organic phase is dried on $Na_2SO_4$, filtered and concentrated at reduced pressure. A white solid of molecule A5 is obtained after recrystallization in acetonitrile.

Yield: 1.57 g (74%)

$^1$H NMR $CDCl_3$, ppm): 0.87 (6H); 1.08-1.43 (34H); 1.48-1.71 (7H); 1.74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).

LC/MS (ESI): 843.6 (calculated ([M+H]$^+$): 843.7).

EXAMPLE A6

Molecule A6

Molecule 10: Product obtained by hydrogenating retinoic acid.

A solution of retinoic acid (19.0 g, 63.24 mmol) in methanol (450 mL) in the presence of 10% palladium on carbon (1.9 g) is placed in a hydrogen atmosphere (1 atm) at ambient temperature. After placing overnight, the reaction medium is filtered on a sintered filter and the filtrate is then concentrated at reduced pressure. A colorless oil of molecule 10 is obtained.

Yield: 19.50 g (99%)

$^1$H NMR $CDCl_3$, ppm): 0.45-2.01 (35H); 2.10-2.17 (1H); 2.33-2.38 (1H); 11.14 (1H).

LC/MS (ESI): 309.3; (calculated ([M−H]$^−$): 309.3).

Molecule 11: Product obtained by coupling Boc-1-amino-4,7,10-trioxa-13-tridecane amine (BocTOTA) and molecule 10.

By means of a similar method to that used for the preparation of molecule 9 applied to molecule 10 (19.3 g, 62.15 mmol) and to BocTOTA (23.9 g, 74.58 mmol), an orange oil of molecule 11 is obtained.

Yield: 37.05 g (97%)

$^1$H NMR $CDCl_3$, ppm): 0.43-1.71 (49H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).

LC/MS (ESI): 613.5; (calculated ([M+H]$^+$): 613.5).

Molecule A6

By means of a similar method to that used for the preparation of molecule A5 applied to molecule 11 (34.9 g, 56.94 mmol), an orange oil of molecule A6 is obtained.

Yield: 28.5 g (97%)

$^1$H NMR $CDCl_3$, ppm): 0.41-1.96 (42H); 2.13 (1H); 2.78 (2H); 3.31-3.36 (2H); 3.53 (4H); 3.55-3.58 (4H); 3.60-3.63 (4H); 6.43 (1H).

LC/MS (ESI): 513.5; (calculated ([M+H]$^+$): 513.5).

EXAMPLE A7

Molecule A7

Molecule 12: Product Obtained by Reacting Molecule 4 and Fmoc-Glu(OtBu)-OH.

To a suspension of Fmoc-Glu(OtBu)-OH (10.55 g, 24.80 mmol) and HATU (9.43 g, 24.80 mmol) in a 1:1 DMF/dichloromethane mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and dichloromethane (3×60 mL).

Molecule 13: Product obtained by reacting Molecule 12 and a 50:50 DMF/morpholine mixture.

Molecule 12, previously washed with DMF, is treated with a 50:50 DMF/morpholine mixture (60 mL). After 1 h 15 of stirring at ambient temperature, the resin is filtered, washed successively with DMF (3×60 mL), isopropanol (1×60 mL) and dichloromethane (3×60 mL).

Molecule 14: Product obtained by reacting molecule A1 and molecule 13.

By means of a similar method to that used for molecule 12 applied to molecule 13 and to molecule A1 (8.07 g, 24.80 mmol) in DMF (60 mL), molecule 14 is obtained.

Molecule A7

By means of a similar method to that used for the preparation of molecule 8 and applied to molecule 14, a white solid of molecule A7 is obtained after purification by silica gel chromatography (eluent: DCM, methanol).

Yield: 2.92 g (52% in 6 stages)

$^1$H NMR (DMSO-d6, ppm): 0.85 (6H); 1.07-2.32 (88H); 2.95-3.09 (2H); 3.28-3.60 (4H); 4.06-4.19 (1.7H); 4.21-4.38 (2.6H); 4.40-4.46 (0.7H); 7.56-7.63 (0.7H); 7.78-8.09 (2.6H); 8.22-8.31 (0.7H); 12.64 (1H).

LC/MS (ESI): 1131.8 (calculated ([M+H]$^+$): 1131.8).

EXAMPLE A8

Molecule A8

Molecule 15: Product obtained by reacting decanoic acid and L-leucine.

By means of a similar method to that used for the preparation of molecule A2 applied to decanoic acid (8.77 g, 50.94 mmol) and to L-leucine (7.00 g, 53.36 mmol), a white solid of molecule 15 is obtained.

Yield: 9.17 g (66%)

$^1$H NMR (DMSO-d6, ppm): 0.82-0.89 (9H); 1.18-1.65 (17H); 2.04-2.14 (2H); 4.19-4.23 (1H); 7.98 (1H); 12.40 (1H).

LC/MS (ESI): 286.2 (calculated ([M+H]$^+$): 286.2).

Molecule 16: Product obtained by reacting molecule 15 and L-lysine methyl ester.

To a solution of molecule 15 (9.16 g, 32.11 mmol) in THF (160 mL) are added successively triethylamine (8.12 g, 80.27 mmol) and 2-(1H-benzotriazol-1-yl)-1,1,3,3-tetramethyluronium tetrafluoroborate (TBTU) and the medium is stirred for 30 min at ambient temperature. L-lysine methyl ester dihydrochloride (3.93 g, 16.86 mmol) is added and the reaction medium is stirred for 3 h then concentrated at reduced pressure. The residue is diluted with AcOEt (200 mL), the organic phase is filtered and washed with a 1 N HCl aqueous solution then with water, dried on $Na_2SO_4$, filtered and concentrated at reduced pressure. A white solid of molecule 16 is obtained after triturating the residue in acetonitrile.

Yield: 7.33 g (66%)

$^1$H NMR (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).

LC/MS (ESI) 695.7 (calculated ([M+H]$^+$): 695.6).

Molecule 17: Product obtained by saponifying molecule 16.

To a solution of molecule 16 (7.33 g, 10.55 mmol) in a THF/methanol/water mixture (105 mL) is added LiOH (505.13 mg, 21.09 mmol) at 0° C. then the medium is stirred for 20 h at ambient temperature and concentrated at reduced pressure. The aqueous phase is acidified with a 1 N HCl solution to pH 1 and the solid formed is filtered, washed with water and dried at reduced pressure to arrive at a white solid of molecule 17.

Yield: 7.09 g (99%)

$^1$H NMR (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).

LC/MS (ESI): 681.7 (calculated ([M+H]$^+$): 681.6).

Molecule 18: Product obtained by reacting molecule 17 and N-Boc ethylenediamine.

By means of a similar method to that used for the preparation of molecule 16 applied to molecule 17 (7.09 g, 10.41 mmol) and to N-Boc ethylenediamine (1.83 g, 11.45 mmol), a white solid of molecule 18 is obtained after trituration in acetonitrile.

Yield: 6.64 g (77%)

$^1$H NMR (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).

LC/MS (ESI): 824.0 (calculated ([M+H]$^+$): 823.7).

Molecule A8

By means of a similar method to that used for molecule A5 applied to molecule 18 (3.00 g, 3.64 mmol) without basic washing, a beige solid of molecule A8 in hydrochloride salt form is obtained after co-evaporating the residue 4 times in methanol.

Yield: 2.66 g (96%)

$^1$H NMR (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).

LC/MS (ESI): 723.7 (calculated ([M+H]$^+$): 723.6).

EXAMPLE A9

Molecule A9

Molecule 19: 13-Methyltetradecanoic acid.

In a dry three-neck round-bottom flask under argon, magnesium (5.50 g, 226.3 mmol) chips are introduced. The magnesium is covered with anhydrous THF (25 mL) and a few drops of 1-bromo-2-methylpropane are added at ambient temperature to initiate the reaction. After observing an exotherm and slight turbidity of the medium, the remaining 1-bromo-2-methylpropane (28.42 g, 207 mmol) diluted in THF (60 mL) is added dropwise in 1 h whereas the temperature of the medium remains stable from 65 to 70° C. The reaction medium is then reflux heated for 2 h.

In a three-neck round-bottom flask under argon, to a solution of CuCl (280 mg, 2.83 mmol) dissolved in N-methylpyrrolidone (NMP) previously distilled at 0° C. is added dropwise a solution of 11-bromoundecanoic acid (25 g, 94.27 mmol) dissolved in THF (60 mL). To this solution is then added dropwise the slightly warm organomagnesium solution diluted in THF (50 mL) so as to maintain the temperature of the medium below 25° C. The mixture is then stirred at ambient temperature for 16 h. The medium is cooled to 0° C. and the reaction is stopped by slowly adding a 1 N HCl aqueous solution to pH 1 (300 mL) and the medium is extracted with hexane (100 mL) and with ethyl acetate (2×75 mL). After washing the organic phase with a 1 N HCl aqueous solution (100 mL), water (100 mL) and drying on $Na_2SO_4$, the solution is filtered and concentrated under vacuum to produce a brown solid. After purification by flash chromatography (cyclohexane, ethyl acetate), a white solid is obtained.

Yield: 18.1 g (79%)

$^1$H NMR CDCl$_3$, ppm): 0.87 (6H); 1.11-1.18 (2H); 1.20-1.38 (16H); 1.51 (1H); 1.63 (2H); 2.35 (2H).

Molecule 20: Product obtained by reacting molecule 19 and L-leucine.

To a solution of molecule 19 (18.05 g, 74.46 mmol) in THF (745 mL) at ambient temperature are added successively DCC (14.63 g, 70.92 mmol) and NHS (8.16 g, 70.92 mmol). After 40 h of stirring at ambient temperature, the medium is cooled to 0° C. for 20 min, filtered on a sintered filter. L-leucine (9.77 g, 74.46 mmol), DIPEA (86 mL) and water (150 mL) are added to the filtrate. After 20 h of stirring at ambient temperature, the medium is diluted with a saturated aqueous solution of NaHCO$_3$ (200 mL). The aqueous phase is washed with ethyl acetate (2×200 mL) and acidified with a 2 N HCl solution to pH 1. The precipitate is filtered, rinsed with plenty of water and vacuum-dried at 50° C. Three times, the solid is triturated in pentane, sonicated then filtered to produce a white solid.

Yield: 18.8 g (75%)

$^1$H NMR CDCl$_3$, ppm): 0.86 (6H); 0.96 (6H); 1.12-1.18 (2H); 1.20-1.78 (22H); 2.24 (2H); 4.58-4.63 (1H); 5.89 (1H).

LC/MS (ESI): 356.2; (calculated ([M+H]$^+$): 356.6).

Molecule 21: Product obtained by reacting molecule 20 and Boc-tri(ethyleneglycol)diamine.

To a solution of molecule 20 (16.7 g, 46.97 mmol) in THF (235 mL) are added successively DIPEA (20.3 mL) and TBTU at ambient temperature. After 20 min of stirring, Boc-tri(ethyleneglycol)diamine (14 g, 56.36 mmol) is added. After stirring at ambient temperature for 5 h, the mixture is concentrated under vacuum. The residue is taken up with ethyl acetate (500 mL), washed with a saturated aqueous solution of NaHCO$_3$ (3×200 mL), a 1 N HCl aqueous solution (3×200 mL) and an aqueous solution saturated with NaCl (3×200 mL). After drying on $Na_2SO_4$, filtration and concentration under vacuum, the residue is purified by flash chromatography (cyclohexane, ethyl acetate, methanol) to produce a colorless oil.

Yield: 23.5 g (85%)

$^1$H NMR CDCl$_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

By means of a similar method to that used for the preparation of molecule A5 applied to molecule 21 (23.46 g, 40.04 mmol) without basic washing, the residue obtained after concentration under vacuum is triturated in an acetonitrile/acetone mixture. The supernatant is removed and the pasty residue is vacuum-dried. The residue is triturated in acetone (150 mL) and the white solid of molecule A9 in hydrochloride salt form is filtered, rinsed with acetone then vacuum-dried.

Yield: 13.0 g (64%)

$^1$H NMR (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H).

LC/MS (ESI): 486.4; (calculated ([M−Cl]$^+$): 486.8).

EXAMPLE A10

Molecule A10

Molecule 22: Product obtained by reacting octanoyl chloride and L-proline.

By means of a similar method to that used for the preparation of molecule A1 and applied to octanoyl chloride (150.0 g, 0.922 mol) and to L-proline (212.3 g, 1.844 mol), a colorless oil of molecule 22 is obtained after washing the organic phase with a 10% HCl aqueous solution (3×300 mL), an aqueous solution saturated with NaCl (300 mL), drying on Na$_2$SO$_4$, filtration on cotton, concentration at reduced pressure, then the residue is purified by flash chromatography (eluent: DCM, MeOH)

Yield: 134 g (60%)

$^1$H NMR CDCl$_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1; (calculated ([M+H]$^+$): 242.2).

Molecule 23: Product obtained by coupling molecule 22 and L-leucine.

To a solution of molecule 22 (132 g, 0.547 mol) in THF (924 mL) cooled to a temperature below 5° C. are added successively NHS (66.1 g, 0.574 mol) and DCC (118.5 g, 0.574 mol). After 21 h of stirring, the precipitate is removed by precipitation and the filtrate is added in 30 min to a solution of L-lysine (41.98 g, 0.287 mol) in a mixture of deionized water (82 mL) and DIPEA (476 mL, 2.735 mol) at 15° C. After 23 h of stirring at ambient temperature, the reaction medium is concentrated at reduced pressure to produce an oily residue which is diluted in water (1.3 L). The aqueous phase is washed twice with AcOEt (2×0.5 L), cooled to a temperature below 10° C., acidified by adding a 6 N HCl solution (120 mL) to attain a pH of 1 then extracted three times with DCM (3×0.6 L). The organic phases are combined, washed with a saturated NaCl solution (0.6 L), dried on Na$_2$SO$_4$ then concentrated at reduced pressure. The foam obtained is taken up with acetone (240 mL) under reflux for 2 h. After leaving overnight at 10° C., pentane (240 mL) is added dropwise. After 1 h of stirring, the precipitate is retrieved by filtering under vacuum, washed with a 1:1 mixture of pentane and acetone (150 mL) then vacuum-dried.

Yield: 83.9 g (52%)

$^1$H NMR CDCl$_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5; (calculated ([M+H]$^+$): 593.4).

Molecule 24: Product obtained by coupling molecule 23 and L-lysine methyl ester (LysOMe).

To molecule 23 (76.26 g, 0.129 mol) are successively added HOPO (3.57 g, 32.1 mmol), LysOMe dihydrochloride (15.0 g, 64.3 mmol) and EDC (34.53 g, 0.18 mol). Then DMF (600 mL) previously cooled to 5° C. is added. After dissolution, triethylamine (43.9 mL, 0.315 mol) is added dropwise while maintaining the temperature below 5° C. for 2 h after addition. After leaving overnight at ambient temperature, the reaction medium is poured onto a mixture of water/ice (2 kg) and DCM (0.5 L). After 15 min of stirring, the phases are separated. The aqueous phase is extracted twice with DCM (2×0.4 L). The organic phases are combined, washed with a 1 N HCl solution (0.5 L) then with a saturated NaCl solution (0.5 L), dried on Na$_2$SO$_4$, concentrated at reduced pressure, then the residue is purified by flash chromatography (eluent: DCM, MeOH).

Yield: 56.7 g (67%)

$^1$H NMR CDCl$_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated at 50° C. overnight. The reaction medium is then diluted with methyl-tetrahydrofuran then the organic phase is washed 4 times with a saturated NaCl solution (4×30 mL) then 2 times with water (2×50 mL) before being dried on Na$_2$SO$_4$ and concentrated at reduced pressure. The residue is solubilized in acetonitrile under reflux for 30 min then the solution is cooled to ambient temperature under stirring overnight. The white precipitate is then retrieved by filtering under vacuum, washed with cold acetonitrile (2×20 mL) then dried under vacuum.

Yield: 3.0 g (74%)

$^1$H NMR CDCl$_3$, ppm): 0.87 (12H); 1.09-2.37 (84H); 2.74-4.56 (25H); 6.85-8.00 (7H). LC/MS (ESI): 1338.0 (calculated ([M+H]$^+$): 1338.0).

EXAMPLE A11

Molecule A11

Molecule 25: Product obtained by reacting molecule 13 and lauric acid.

By means of a similar method to that used for molecule 5 applied to molecule 13 (28 mmol) and lauric acid (28.04 g, 140 mmol) in DMF (330 mL), molecule 25 is obtained.

Molecule A11

By means of a similar method to that used for molecule 8 applied to molecule 25, a white solid of molecule A11 is obtained after recrystallization in acetonitrile.

Yield: 13.9 g (56% in 6 stages)

$^1$H NMR (DMSO-d6, ppm): 0.85 (6H); 1.05-1.61 (60H); 1.62-1.75 (2H); 1.78-1.91 (2H); 2.04-2.27 (8H); 2.96-3.06 (2H); 4.08-4.13 (1H); 4.17-4.22 (1H); 4.27-4.34 (1H); 7.82 (1H); 7.86 (1H); 7.90 (1H); 8.03 (1H); 12.54 (1H).

LC/MS (ESI+): 881.7 (calculated ([M+H]$^+$): 881.7).

EXAMPLE A12

Molecule A12

Molecule 26: Product obtained by reacting molecule 13 and Fmoc-Glu(OtBu)-OH.

By means of a similar method to that used for molecule 5 applied to molecule 13 (9.92 mmol) and to Fmoc-Glu (OtBu)-OH (21.10 g, 49.60 mmol) in N-methyl-2-pyrrolidone (NMP, 120 mL), molecule 26 is obtained.

Molecule 27: Product obtained by reacting molecule 26 and an 80:20 NMP/piperidine mixture.

By means of a similar method to that used for molecule 4 applied to molecule 26, using NMP instead of DMF, molecule 27 is obtained.

Molecule 28: Product obtained by reacting molecule 27 and Fmoc-Glu(OtBu)-OH.

By means of a similar method to that used for molecule 26 applied to molecule 27 and to Fmoc-Glu(OtBu)-OH (21.10 g, 49.60 mmol), molecule 28 is obtained.

Molecule 29: Product obtained by reacting molecule 28 and an 80:20 NMP/piperidine mixture.

By means of a similar method to that used for molecule 27 applied to molecule 28, molecule 29 is obtained.

Molecule 30: Product obtained by reacting molecule 29 and molecule A1.

By means of a similar method to that used for molecule 26 applied to molecule 29 (4.96 mmol) and to molecule A1 (8.07 g, 24.80 mmol), molecule 30 is obtained.

Molecule A12

By means of a similar method to that used for molecule 8 applied to molecule 30, a white solid of molecule A12 is obtained after purification by flash chromatography (DCM, MeOH).

Yield: 4.6 g (50% in 10 stages)

$^1$H NMR (CD$_3$OD, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+Na]$^+$): 1894.2).

EXAMPLE A14

Molecule A14

Molecule 33: Product obtained by reacting N-☐-Boc-L-Lysine and palmitoyl chloride By means of a similar method to that used for the preparation of molecule A1 applied to N-☐-Boc-L-Lysine (53.76 g, 218.28 mmol) and to palmitoyl chloride (50.00 g, 181.90 mmol), a white solid of molecule 33 is obtained after recrystallizing 2 times in acetonitrile and purification by flash chromatography (eluent: dichloromethane, methanol).

Yield: 49.10 g (70%)

$^1$H NMR (DMSO-d$_6$, ppm): 0.85 (3H); 1.09-1.66 (32H); 1.37 (9H); 2.01 (2H); 2.93-3.06 (2H); 3.78-3.85 (1H); 6.61-6.68 (0.2H); 6.96-6.98 (0.8H); 7.66-7.75 (1H); 12.38 (1H).

LC/MS (ESI): 385.1 (calculated ([M−Boc+H]$^+$): 385.3).

Molecule 34: Product obtained by reacting molecule 33 and methyl iodide.

To a solution of molecule 33 (23.40 g, 48.28 mmol) in DMF (200 mL) at ambient temperature are added K$_2$CO$_3$ (10.01 g, 72.41 mmol) followed by methyl iodide (5.96 mL, 98.55 mmol). The medium is stirred for 48 h. Water (350 mL) is added and the suspension is stirred for 15 min. The latter is then filtered on a sintered filter and the solid obtained is rinsed with water (2×250 mL) and vacuum-dried. The solid is then solubilized in DCM (300 mL). The solution is washed with water (200 mL) then with an aqueous solution saturated with NaCl (200 mL), dried on Na$_2$SO$_4$, filtered and concentrated at reduced pressure. A white solid of molecule 34 is obtained after recrystallization in acetonitrile.

Yield: 19.22 g (80%)

$^1$H NMR CDCl$_3$, ppm): 0.87 (3H); 1.06-2.23 (34H); 1.43 (9H); 3.09-3.33 (2H); 3.72 (3H); 3.94-4.35 (1H); 4.69-5.23 (1H); 5.33-5.75 (1H).

LC/MS (ESI): 543.3 (calculated ([M−H+HCOOH]$^−$): 543.4).

Molecule 35: Product obtained by hydrolyzing molecule 34 with hydrochloric acid

By means of a similar method to that used for the preparation of molecule A5 applied to molecule 34 in solution in a 1:1 DCM/methanol mixture (385 mL), a white solid of molecule 35 is obtained after concentration at reduced pressure and co-evaporation with DCM followed by methanol.

Yield: 16.73 g (99%)

$^1$H NMR (DMSO-d$_6$, ppm): 0.85 (3H); 1.08-1.50 (30H); 1.67-1.84 (2H); 2.03 (2H); 2.94-3.13 (2H); 3.74 (3H); 3.92-4.01 (1H); 7.77-7.87 (1H); 8.25-8.73 (3H).

LC/MS (ESI): 399.2 (calculated ([M+H]$^+$): 399.4).

Molecule A14

To a suspension of molecule 35 (14.70 g, 33.79 mmol) in a mixture of methyl-THF (338 mL) and DMF (30 mL) are added successively DIPEA (17.70 mL, 101.40 mmol) followed by a solution of succinic anhydride (5.07 g, 50.68 mmol) in THF (60 mL). The medium is stirred for 4 h at ambient temperature. Methyl-THF (100 mL) is added and the organic phase is washed with a 5% HCl aqueous solution (300 mL). The aqueous phase is extracted with methyl-DCM (2×150 mL). The combined organic phases are washed with water (2×150 mL) then with an aqueous solution saturated with NaCl (150 mL), dried on Na$_2$SO$_4$, filtered and concentrated at reduced pressure. The crude product is purified by flash chromatography (eluent: DCM, methanol) then solubilized in methyl-THF. The purified product is then suspended in water. The suspension is stirred by sonication for 20 min followed by magnetic stirring for 30 min. A white solid of molecule A14 is obtained after filtration and drying at reduced pressure.

Yield: 12.99 g (77%)

$^1$H NMR (DMSO-d$_6$, ppm): 0.85 (3H); 1.08-1.71 (32H); 2.02 (2H); 2.29-2.45 (4H); 2.94-3.04 (2H); 3.61 (3H); 4.14-4.22 (1H); 7.70 (1H); 8.20 (1H); 12.04 (1H).

LC/MS (ESI): 499.3 (calculated ([M+H]$^+$): 499.4).

EXAMPLE A15

Molecule A15

Molecule 36: Product obtained by coupling L-proline and palmitoyl chloride

By means of a similar method to that used for the preparation of molecule A1 applied to L-proline (38.05 g, 906.00 mmol) and to palmitoyl chloride (14.01 g, 350.16 mmol), a white solid of molecule 36 is obtained.

Yield: 47.39 g (96%)

$^1$H NMR CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

LC/MS (ESI): 354.5 (calculated ([M+H]$^+$): 354.3).

Molecule 37: Product obtained by reacting molecule 36 and N-Bocethylenediamine.

By means of a similar method to that used for molecule 9 applied to molecule 36 (75.1 g, 212.4 mmol), a white solid of molecule 37 is obtained after trituration in diisopropylether (3×400 mL) and vacuum-drying at 40° C.

Yield: 90.4 g (86%).

$^1$H NMR CDCl$_3$, ppm): 0.88 (3H); 1.20-1.37 (24H); 1.44 (9H); 1.54-1.70 (2H); 1.79-1.92 (1H); 1.92-2.04 (1H); 2.03-2.17 (1H); 2.17-2.44 (3H); 3.14-3.36 (4H); 3.43 (1H); 3.56

(1H); 4.29 (0.1H); 4.51 (0.9H); 4.82 (0.1H); 5.02 (0.9H); 6.84 (0.1H); 7.22 (0.9H).

Molecule 38: Product obtained by hydrolyzing molecule 37 with hydrochloric acid

By means of a similar method to that used for the preparation of molecule A5 applied to molecule 37 (38.17 g, 76.99 mmol), a white solid of molecule 38 is obtained.

$^1$H NMR CDCl$_3$, ppm): 0.88 (3H); 1.07-1.40 (24H); 1.49-1.63 (2H); 1.77-2.18 (4H); 2.18-2.45 (2H); 3.14-3.32 (2H); 3.42-3.63 (2H); 3.63-3.84 (2H); 4.37 (0.1H); 4.48 (0.9H); 6.81-8.81 (4H).

LC/MS (ESI): 396.5; (calculated ([M+H]$^+$): 396.4).

Molecule A15

By means of a similar method to that used for the preparation of molecule A14 applied to molecule 38 (10.00 g, 253.00 mmol), a white solid of molecule A15 is obtained.

Yield: 10.00 g (80%)

$^1$H NMR (DMSO, ppm): 0.85 (3H); 1.07-1.51 (26H); 1.69-2.02 (4H); 2.08-2.53 (6H); 3.01-3.18 (4H); 3.39-3.58 (2H); 4.13-4.18 (0.7H); 4.23-4.27 (0.3H); 7.70-7.78 (1.4H); 7.81-7.86 (0.3H); 8.00-8.04 (0.3H); 12.08 (1H).

LC/MS (ESI): 496.3 (calculated ([M+H]$^+$): 496.4).

EXAMPLE A16

Molecule A16

Molecule 39: Product obtained by reacting molecule 36 and Boc-1-amino-4,7,10-trioxa-13-tridecane amine.

By means of a similar method to that used for the preparation of molecule 9 applied to molecule 36 (17.00 g, 48.08 mmol) and to Boc-1-amino-4,7,10-trioxa-13-tridecane amine (18.49 g, 57.70 mmol), a pale yellow oil of molecule 39 is obtained.

Yield: 31.11 g (98%)

$^1$H NMR (DMSO-d$_6$, ppm): 0.85 (3H); 1.17-1.31 (24H); 1.37 (9H); 1.41-1.51 (2H); 1.54-1.67 (4H); 1.69-2.02 (4H); 2.08-2.29 (2H); 2.91-3.00 (2H); 3.01-3.17 (2H); 3.31-3.58 (14H); 4.20 (0.65H); 4.26 (0.35H); 6.29-6.82 (1H); 7.68 (0.65H); 8.02 (0.35H).

LC/MS (ESI): 656.4 (calculated ([M+H]$^+$): 656.5).

Molecule 40: Product obtained by hydrolyzing molecule 39 with hydrochloric acid

By means of a similar method to that used for the preparation of molecule A5 applied to molecule 39 (31.11 g, 47.43 mmol), a yellow wax of molecule 40 is obtained.

Yield: 27 g (97%)

$^1$H NMR (DMSO-d$_6$, ppm): 0.85 (3H); 1.18-1.31 (24H); 1.40-1.51 (2H); 1.55-1.67 (2H); 1.70-2.04 (6H); 2.09-2.30 (2H); 2.78-2.89 (2H); 2.99-3.18 (2H); 3.33-3.58 (14H); 4.19 (0.65H); 4.27 (0.35H); 7.55-8.14 (4H).

LC/MS (ESI): 556.3 (calculated ([M+H]$^+$): 556.5).

Molecule A16

Molecule 40 (26.40 g, 44.50 mmol) in hydrochloride form is solubilized in a mixture of DCM (350 mL) and an aqueous solution of NaHCO$_3$ (350 mL). The organic phase is separated and the aqueous phase is extracted with DCM (2×150 mL). The organic phases are combined dried on Na$_2$SO$_4$, filtered and concentrated at reduced pressure to produce a colorless oil. By means of a similar method to that used for the preparation of molecule A14, a yellow resin of molecule A16 is obtained after purification by flash chromatography (eluent: DCM, methanol).

Yield: 19.93 g (68%)

$^1$H NMR (DMSO-d$_6$, ppm): 0.85 (3H); 1.18-1.30 (24H); 1.40-1.51 (2H); 1.55-1.67 (4H); 1.70-2.02 (4H); 2.07-2.45 (6H); 2.99-3.18 (4H); 3.33-3.57 (14H); 4.19 (0.65H); 4.26 (0.35H); 7.68 (0.65H); 7.78 (1H); 8.02 (0.35H); 12.03 (1H).

LC/MS (ESI): 656.3 (calculated ([M+H]$^+$): 656.5).

EXAMPLE A17

Molecule A17

Molecule 41: Product obtained by solid phase peptide synthesis (SPPS)

Molecule 41 is obtained by means of the conventional solid phase peptide synthesis (SPPS) method on 2-chlorotrityl resin To a solution of 4,7,10-trioxa-1,13-tridecanediamine (TOTA, 76.73 mL, 350 mmol) in DCM (350 mL) is added DIPEA (60.96 mL, 350 mmol). This solution is then poured onto the 2-chlorotrityl resin (47.30 g, 0.74 mmol/g) previously washed with DCM in a reaction vessel suitable for SPPS. After 1.5 h of stirring at ambient temperature, methanol (26 mL) is added and the medium is stirred for 15 min. The resin is filtered, washed successively with DCM (3×350 mL), DMF (2×350 mL), DCM (2×350 mL), isopropanol (1×350 mL) and DCM (3×350 mL). The □-methyl ester of N-Fmoc-L-glutamic acid (1.5 eq) followed by molecule 36 (1.5 eq) are coupled using the coupling agent 1-[bis(dimethylamino)methylene]-1H-1,2,3-triazolo[4,5-b]pyridinium 3-oxide hexafluorophosphate (HATU, 1.5 equivalents) and DIPEA (3 equivalents) in a 1:1 DCM/DMF mixture. A 1:1 DMF/morpholine mixture is used for the cleavage step of the Fmoc protecting group. The resin is washed with DCM, DMF and methanol after each coupling and deprotection step. The cleavage of the product from the resin is carried out using a 1:1 TFA/DCM mixture. The solvents are then evaporated under vacuum; the residue is solubilized in DCM (500 mL) and the organic phase is washed with a 5% Na$_2$CO$_3$ aqueous solution (500 mL). After drying on Na$_2$SO$_4$, the organic phase is filtered, concentrated under vacuum and a yellow oil of molecule 41 is obtained after drying at reduced pressure.

Yield: 15.95 g (65%)

1H NMR (DMSO-d6, ppm): 0.85 (3H); 1.16-1.31 (24H); 1.38-1.68 (6H); 1.68-2.37 (12H); 2.58 (2H); 3.01-3.17 (2H); 3.31-3.55 (14H); 3.58 (3H); 4.09-4.18 (0.7H); 4.18-4.29 (1H); 4.36-4.43 (0.3H); 7.62 (0.7H); 7.86 (0.7H); 7.98 (0.3H); 8.23 (0.3H).

LC/MS (ESI): 699.4 (calculated ([M+H]+): 699.5).

Molecule A17

By means of a similar method to that used for the preparation of molecule A14 applied to molecule 41 (14.05 g, 20.10 mmol), a yellow resin of molecule A17 is obtained after purification by flash chromatography (eluent: DCM, methanol).

Yield: 7.70 g (48%)

1H NMR (DMSO-d6, ppm): 0.85 (3H); 1.17-1.31 (24H); 1.38-1.54 (2H); 1.54-1.68 (4H); 1.68-2.21 (7H); 2.21-2.36 (5H); 2.36-2.44 (2H); 3.01-3.16 (4H); 3.34-3.55 (14H); 3.57 (3H); 4.10-4.18 (0.7H); 4.18-4.30 (1H); 4.40 (0.3H); 7.60 (0.7H); 7.78 (1H); 7.85 (0.7H); 7.95 (0.3H); 8.22 (0.3H); 12.06 (1H).

LC/MS (ESI): 799.5 (calculated ([M+H]+): 799.5).

EXAMPLE A18

Molecule A18

Molecule 42: Product obtained by reacting molecule A1 and Boc-1-amino-4,7,10-trioxa-13-tridecane amine.

By means of a similar method to that used for the preparation of molecule 18 applied to molecule A1 (44.80 g, 137.64 mmol) and to Boc-1-amino-4,7,10-trioxa-13-tridecane amine (52.92 g, 165.16 mmol), an orange oil of molecule 42 is obtained.

Yield: 85.63 g (99%)

1H NMR CDCl$_3$, ppm): 0.87 (3H); 1.08-1.56 (20H); 1.43 (9H); 1.58-1.67 (2H); 1.70-2.00 (6H); 2.04-2.41 (4H); 3.16-3.77 (18H); 4.26-4.29 (0.2H); 4.50-4.54 (0.8H); 4.68-5.10 (1H); 6.74 (0.2H); 7.19 (0.8H).

LC/MS (ESI): 628.4; (calculated ([M+H]$^+$): 628.5).

Molecule 43: Product obtained by hydrolyzing molecule 42 with hydrochloric acid

By means of a similar method to that used for the preparation of molecule A5 applied to molecule 42 (43.40 g, 69.12 mmol), a white solid of molecule 43 in hydrochloride salt form is obtained after trituration in diethylether, solubilizing the residue in water and freeze-drying.

Yield: 38.70 g (98%)

1H NMR (DMSO, ppm): 0.85 (3H); 1.07-1.38 (20H); 1.41-1.52 (2H); 1.55-1.66 (2H); 1.70-2.02 (6H); 2.08-2.30 (2H); 2.78-2.87 (2H); 3.00-3.16 (2H); 3.29-3.66 (14H); 4.16-4.22 (0.65H); 4.25-4.30 (0.35H); 7.74 (0.65H); 7.86 (3H); 8.10 (0.35H).

LC/MS (ESI): 528.4; (calculated ([M+H]$^+$): 528.4).

Molecule A18

By means of a similar method to that used for the preparation of molecule A14 applied to molecule 43 (13.09 g, 24.8 mmol), a yellow resin of molecule A18 is obtained after purification by flash chromatography (eluent: DCM, methanol).

Yield: 8.53 g (55%)

1H NMR (DMSO-d6, ppm): 0.86 (3H); 1.10-1.39 (20H); 1.42-1.51 (2H); 1.57-1.67 (4H); 1.71-2.03 (4H); 2.09-2.32 (4H); 2.42 (2H); 3.01-3.17 (4H); 3.36-3.57 (14H); 4.18-4.21 (0.65H); 4.24-4.28 (0.35H); 7.69 (0.65H); 7.80 (1H); 8.03 (0.35H); 12.04 (1H).

LC/MS (ESI): 628.5 (calculated ([M+H]$^+$): 628.5).

EXAMPLE A19

Molecule A19

Molecule 44: Product obtained by SPPS

By means of a similar SPPS method to that used for the preparation of molecule 41 and applied to TOTA, to N-Fmoc-L-Leucine, N-Fmoc-L-proline and to myristic acid, an orange oil of molecule 44 is obtained.

Yield: 19.87 g (69%)

$^1$H NMR CDCl$_3$, ppm): 0.72-1.06 (9H); 1.09-1.42 (20H); 1.42-2.40 (17H); 2.80 (2H); 3.22-3.81 (16H); 4.25-4.61 (2H); 6.56-7.23 (2H).

LC/MS (ESI): 641.5; (calculated ([M+H]$^+$): 641.5).

Molecule A19

After a similar method to that used for the preparation of molecule A14 applied to molecule 44 (13.09 g, 204.42 mmol), 4.81 g of the product obtained by purification by flash chromatography (eluent: DCM, methanol) is solubilized in a mixture of DCM (50 mL) and THF (5.5 mL) then washed with an aqueous solution saturated with NaCl (50 mL), a 0.1 N HCl aqueous solution (50 mL) and an aqueous solution saturated with NaCl (50 mL). The organic phase is dried on Na$_2$SO$_4$, filtered and concentrated at reduced pressure. A yellow oil of molecule A19 is obtained.

Yield: 4.20 g $^1$H NMR (DMSO-d$_6$, ppm): 0.72-1.02 (9H); 1.08-1.34 (20H); 1.34-2.23 (14H); 2.23-2.35 (3H); 2.42 (2H); 3.01-3.17 (4H); 3.17-3.66 (14H); 4.15-4.44 (2H); 7.53-8.23 (3H); 12.06 (1H).

LC/MS (ESI): 741.5; (calculated ([M+H]$^+$): 741.5).

EXAMPLE A21

Molecule A21

Molecule 46: Product obtained by SPPS

By means of a similar SPPS method to that used for the preparation of molecule 41 and applied to TOTA, to N-Fmoc-L-phenylalanine and to molecule A1, an orange oil of molecule 46 is obtained and used without purification.

Yield: 15.07 g (72%)

$^1$H NMR CDCl$_3$, ppm): 0.87 (3H); 1.08-1.42 (20H); 1.42-1.62 (2H); 1.62-1.99 (7H); 1.99-2.26 (3H); 2.72 (2H); 2.86 (2H); 2.94-3.72 (18H); 4.20-4.72 (2H); 6.63-7.37 (7H).

LC/MS (ESI): 675.65; (calculated ([M+H]$^+$): 675.5).

Molecule A21

By means of a similar method to that used for the preparation of molecule A19 applied to molecule 46 (13.79 g, 20.43 mmol), a white solid of molecule A21 is obtained.

Yield: 7.56 g (48%)

$^1$H NMR (DMSO-d$_6$, ppm): 0.86 (3H); 1.02-1.42 (21H); 1.42-2.20 (10H); 2.23-2.38 (3H); 2.42 (2H); 2.78-3.18 (6H); 3.23-3.59 (14H); 4.12-4.58 (2H); 7.10-7.30 (5H); 7.53-8.33 (3H); 12.08 (1H).

LC/MS (ESI): 775.5; (calculated ([M+H]$^+$): 775.5).

EXAMPLE A22

Molecule A22

By means of a similar method to that used for the preparation of molecule A14 applied to molecule A6 (22.15 g, 43.19 mmol), a yellow oil of molecule A22 is obtained.

Yield: 25.19 g (95%)

$^1$H NMR (DMSO-d$_6$, ppm): 0.42-1.51 (33H); 1.51-2.05 (8H); 2.29 (2H); 2.41 (2H); 3.07 (4H); 3.38 (4H); 3.43-3.54 (8H); 7.72 (1H); 7.79 (1H); 12.03 (1H).

LC/MS (ESI): 613.5 (calculated ([M+H]$^+$): 613.5).

EXAMPLE A23

Molecule A23

Molecule 47: Product obtained by hydrogenating phytol.

To a solution of phytol (30.00 g, 101.20 mmol) in THF (450 mL) in argon is added platinum dioxide (PtO$_2$, 1.15 g, 6.61 mmol). The medium is placed under 1 bar of dihydrogen then stirred for 4 h at ambient temperature. After filtering on celite by rinsing with THF, a black oil of molecule 47 is obtained after concentration at reduced pressure.

Yield: 29.00 g (96%)

$^1$H NMR CDCl$_3$, ppm): 0.84 (6H); 0.86 (6H); 0.89 (3H); 1.00-1.46 (22H); 1.46-1.68 (3H); 3.61-3.73 (2H).

Molecule 48: Product obtained by oxidizing molecule 47

To a solution of molecule 47 (29.0 g, 97.13 mmol) in a dichloroethane/water mixture (485 mL/388 mL) are added successively tetrabutylammonium bromide (16.90 g, 52.45 mmol), acetic acid (150 mL, 2.62 mol) followed by KMnO$_4$ (46.05 g, 291.40 mmol) in small fractions while maintaining the temperature from 16 to 19° C. The reaction medium is then stirred for 4.5 h under reflux, cooled to 10° C. then acidified to pH 1 with a 6 N HCl solution (20 mL). Na$_2$SO$_3$ (53.90 g) is added progressively while maintaining the temperature at 10° C. and the medium is stirred until completely discolored. Water (200 mL) is added, the phases are separated and the aqueous phase is extracted with DCM (2×400 mL). The combined organic phases are washed with a 10% HCl aqueous solution (20 mL), water (2×200 mL), an aqueous solution saturated with NaCl (200 mL), dried on Na$_2$SO$_4$, filtered and concentrated at reduced pressure. A yellow oil of molecule 48 is obtained after purification by flash chromatography (eluent: cyclohexane, AcOEt).

Yield: 28.70 g (94%)

$^1$H NMR CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^−$): 311.3).

Molecule 49: Product obtained by coupling molecule 48 and methyl L-prolinate.

By means of a similar method to that used for the preparation of molecule 9 applied to molecule 48 (18.00 g, 57.59 mmol) and to methyl L-prolinate hydrochloride (14.31 g, 86.39 mmol) in DCM (380 mL), a yellow oil of molecule 49 is obtained after washing the organic phase with an aqueous solution saturated with NaHCO$_3$ (2×150 mL), a 10% HCL aqueous solution (2×150 mL), an aqueous solution saturated with NaCl (2×150 mL), followed by drying on Na$_2$SO$_4$, filtration and concentration at reduced pressure.

Yield: 23.20 g (95%)

$^1$H NMR (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 50: Product obtained by saponifying molecule 49.

By means of a similar method to that used for the preparation of molecule 17 applied to molecule 49 (21.05 g, 49.68 mmol), a yellow oil of molecule 50 is obtained.

Yield: 20.40 g (99%)

$^1$H NMR (DMSO-d$_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule 51: Product obtained by coupling molecule 50 and Boc-1-amino-4,7,10-trioxa-13-tridecane amine.

By means of a similar method to that used for the preparation of molecule 9 applied to molecule 50 (8.95 g, 21.85 mmol) and to TOTA (8.40 g, 26.21 mmol), a colorless oil of molecule 51 is obtained after purification by flash chromatography (eluent: DCM, AcOEt, methanol).

Yield: 10.08 g (65%)

$^1$H NMR (DMSO-d$_6$, ppm): 0.78-0.89 (15H); 0.97-1.43 (29H); 1.43-1.55 (1H); 1.55-1.66 (4H); 1.71-2.30 (7H); 2.95 (2H); 3.00-3.19 (2H); 3.34-3.58 (14H); 4.17-4.29 (1H); 6.30-6.79 (1H); 7.67 (0.65H); 8.00 (0.35H).

LC/MS (ESI): 712.6 (calculated ([M+H]$^+$): 712.6).

Molecule 52: Product obtained by hydrolyzing molecule 42 with hydrochloric acid

By means of a similar method to that used for the preparation of molecule A5 applied to molecule 51 (10.08 g, 14.16 mmol), the residue obtained after concentration at reduced pressure is solubilized in DCM (200 mL). The organic phase is washed with a 2 N NaOH aqueous solution (2×100 mL), dried on Na$_2$SO$_4$, filtered and concentrated at reduced pressure. A colorless oil of molecule 52 in neutral amine form is obtained.

Yield: 8.23 g (95%)

$^1$H NMR (DMSO-d$_6$, ppm): 0.78-0.89 (15H); 0.97-1.43 (20H); 1.43-1.69 (6H); 1.69-2.30 (8H); 2.56 (2H); 2.99-3.19 (2H); 3.31-3.58 (14H); 4.15-4.29 (1H); 7.70 (0.65H); 8.04 (0.35H).

LC/MS (ESI): 612.5 (calculated ([M+H]+): 612.5).

Molecule A23

By means of a similar method to that used for the preparation of molecule A14 applied to molecule 52 (15.40 g, 25.17 mmol), a yellow oil of molecule A23 is obtained.

Yield: 15.19 g (85%)

$^1$H NMR (DMSO-d$_6$, ppm): 0.76-0.91 (15H); 0.98-2.26 (32H); 2.29 (2H); 2.41 (2H); 2.98-3.18 (4H); 3.32-3.63 (14H); 4.15-4.29 (1H); 7.68 (0.7H); 7.78 (1H); 8.01 (0.3H); 12.02 (1H).

LC/MS (ESI): 712.5 (calculated ([M+H]$^+$): 712.5).

EXAMPLE A26

Molecule A26

Molecule 55: Product obtained by SPPS

Molecule 55 is obtained by means of the conventional solid phase peptide synthesis (SPPS) method on 2-chlorotrityl chloride (CTC) resin (47.56 g, 0.74 mmol/g).

The grafting of the first amino acid Fmoc-Glu(OtBu)-OH (2.5 equivalents) is performed in DCM (10 V), in the presence of DIPEA (5.0 equivalents). The unreacted sites are capped with methanol (0.8 mL/g resin) at the end of the reaction.

The protected amino acids Fmoc-Glu(OtBu)-OH (1.5 equivalents (×2)) and molecule A1 (1.5 equivalents) are coupled in DMF (10 V), in the presence of HATU (1.0 equivalent with respect to the acid) and DIPEA (2.0 equivalents with respect to the acid).

The protecting groups Fmoc are removed using an 80:20 DMF/piperidine solution (10 V).

The product is cleaved from the resin using an 80:20 DCM/HFIP solution (10 V).

After concentration at reduced pressure, two co-evaporations are performed on the residue with dichloromethane followed by diisopropylether. The product is purified by silica gel chromatography (dichloromethane, methanol). A colorless gum of molecule 55 is obtained.

Yield: 21.4 g (69% in 8 stages)

$^1$H NMR (DMSO-d6, ppm): 0.85 (3H); 1.16-1.30 (20H); 1.34-1.41 (27H); 1.41-1.53 (2H); 1.67-2.33 (18H); 3.26-3.60 (2H); 4.09-4.44 (4H); 7.73 (0.65H); 7.85 (0.65H); 7.93-8.04 (1H); 8.17 (0.35H); 8.27 (0.35H); 12.64 (1H).

LC/MS (ESI+): 881.7 (calculated ([M+H]$^+$): 881.6).

Molecule 56: Product obtained by reacting molecule 55 and 2-phthalimido ethylamine.

By means of a similar method to that used for the preparation of molecule 9 applied to molecule 55 (21.38 g, 24.26 mmol) and to 2-phthalimido ethylamine hydrochloride (HCl.PhthalEDA, 6.60 g, 29.12 mmol) in DCM and in the presence of DIPEA (5.07 mL, 29.12 mmol), a beige foam of molecule 56 is obtained without purification.

Yield: 25.56 g (100%)

$^1$H NMR (DMSO-d6, ppm): 0.85 (3H); 1.17-1.30 (20H); 1.34-1.41 (27H); 1.41-1.52 (2H); 1.56-2.32 (18H); 3.18-3.69 (6H); 4.01-4.43 (4H); 7.64-8.30 (8H).

LC/MS (ESI): 1053.8; (calculated ([M+H]$^+$): 1053.6).

Molecule A26

Molecule 56 (25.56 g, 24.26 mmol) is solubilized in a solution of 40% methylamine in MeOH (242.5 mL, 2.38 mol) at 4° C. then the mixture is stirred at ambient temperature for 5 h. Silica is added to the reaction medium then the latter is concentrated at reduced pressure. The residue is purified by silica gel chromatography (solid deposition, dichloromethane, methanol, NH$_3$) to produce molecule A26 in the form a pale yellow gum. This product is solubilized in DCM (250 mL) then the solution is washed with a 10% HCl aqueous solution. The aqueous phase is extracted with DCM (100 mL). The combined organic phases are dried on Na$_2$SO$_4$, filtered then concentrated at reduced pressure to produce the hydrochloride of molecule A26 in the form of a white solid.

Yield: 13.5 g (58%)

$^1$H NMR (DMSO-d6, ppm): 0.85 (3H); 1.18-1.30 (20H); 1.34-1.42 (27H); 1.42-1.53 (2H); 1.66-2.02 (9H); 2.02-2.39 (9H); 2.79-2.91 (2H); 3.25-3.64 (4H); 4.08-4.46 (4H); 7.68-8.37 (7H).

LC/MS (ESI): 923.8; (calculated ([M+H]$^+$): 923.6).

EXAMPLE A27

Molecule A27

Molecule A27 is obtained by means of the conventional solid phase peptide synthesis (SPPS) method on 2-chlorotrityl chloride (CTC) resin (24.00 g, 1.37 mmol/g).

The grafting of the first amino acid Fmoc-6-aminohexanoic acid (1.5 equivalents) is performed in DCM (10 V), in the presence of DIPEA (2.5 equivalents). The unreacted sites are capped with methanol (0.8 mL/g resin) at the end of the reaction.

The protected amino acid Fmoc-Glu-OMe (1.5 equivalents) and palmitic acid (1.5 equivalents) are coupled in DMF (10 V), in the presence of HATU (1.0 equivalent with respect to the acid) and DIPEA (1.5 equivalents with respect to the acid).

The protecting groups Fmoc are removed using an 80:20 DMF/piperidine solution (10 V).

The product is cleaved from the resin using an 80:20 DCM/HFIP solution (10 V).

After concentration at reduced pressure, two co-evaporations are performed on the residue with dichloromethane followed by toluene. The product is purified by recrystallization in ethyl acetate. A white solid of molecule A27 is obtained.

Yield: 11.54 g (68% in 6 stages)

$^1$H NMR CDCl$_3$, ppm): 0.88 (3H); 1.19-1.35 (24H); 1.35-1.44 (2H); 1.50-1.70 (6H); 1.91-2.01 (1H); 2.14-2.40 (7H); 3.14-3.34 (2H); 3.75 (3H); 4.51-4.59 (1H); 6.53 (1H); 6.70 (1H).

LC/MS (ESI+): 513.4 (calculated ([M+H]$^+$): 513.4).

Part B—Hydrophobic Co-Polyamino Acid Synthesis

| | CO-POLYAMINO ACIDS BEARING CARBOXYLATE CHARGES AND HYDROPHOBIC RADICALS |
|---|---|
| B1 | 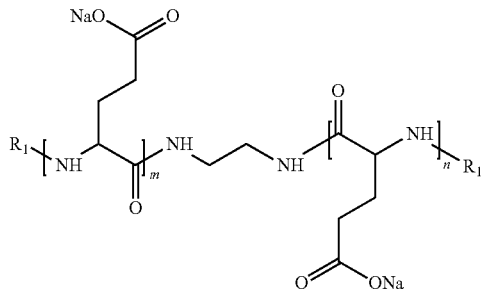<br>i = 0.050, DP (m + n) = 40<br>R$_1$ = H, pyroglutamate or<br>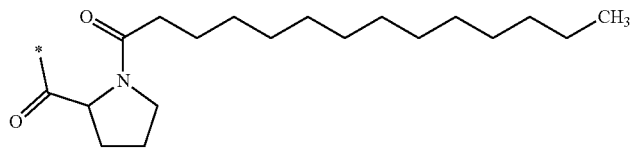 |

| # | CO-POLYAMINO ACIDS BEARING CARBOXYLATE CHARGES AND HYDROPHOBIC RADICALS |
|---|---|
| B2 | 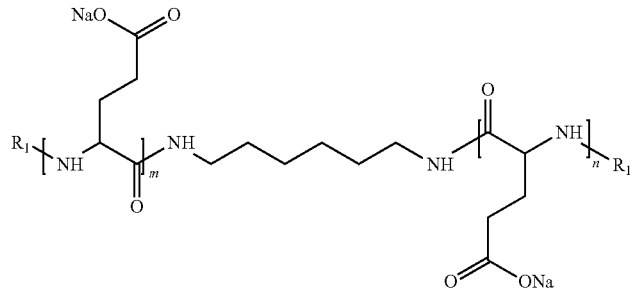<br>i = 0.0657, DP (m + n) = 30<br>$R_1$ = H, pyroglutamate or<br>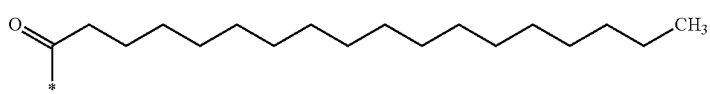 |
| B3 | 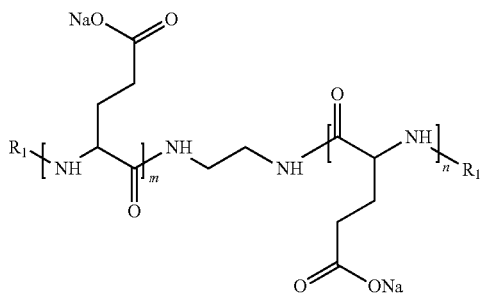<br>i = 0.0808, DP (m + n) = 24<br>$R_1$ = H, pyroglutamate or<br>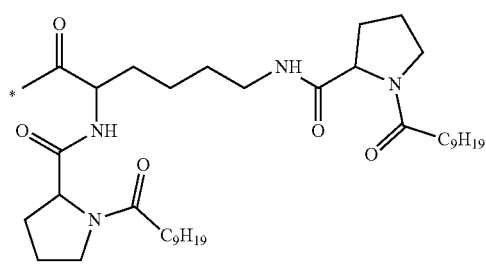 |

| # | CO-POLYAMINO ACIDS BEARING CARBOXYLATE CHARGES AND HYDROPHOBIC RADICALS |
|---|---|
| B4 | 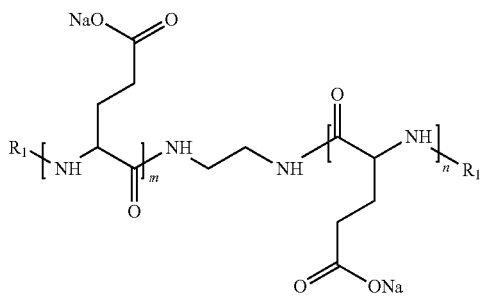<br>i = 0.134, DP (m + n) = 14<br>$R_1$ = H, pyroglutamate or<br>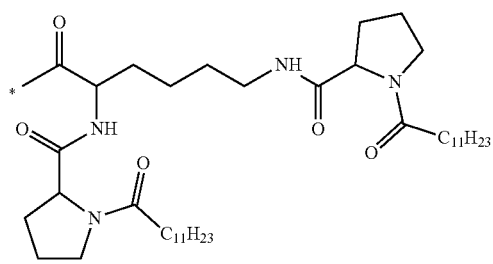 |
| B5 | 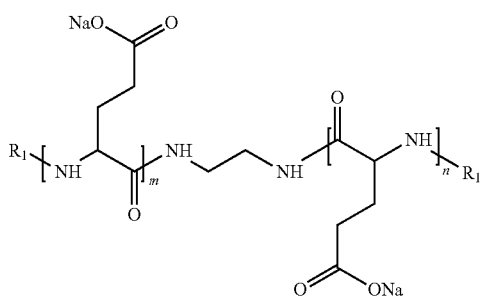<br>i = 0.077, DP (m + n) = 24<br>$R_1$ = H, pyroglutamate or<br>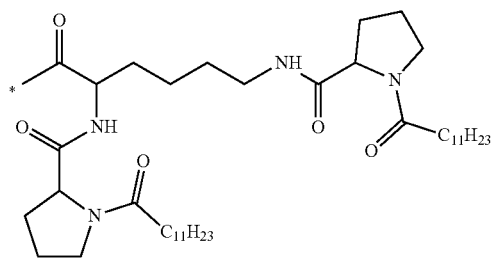 |

| # | CO-POLYAMINO ACIDS BEARING CARBOXYLATE CHARGES AND HYDROPHOBIC RADICALS |
|---|---|
| B6 | 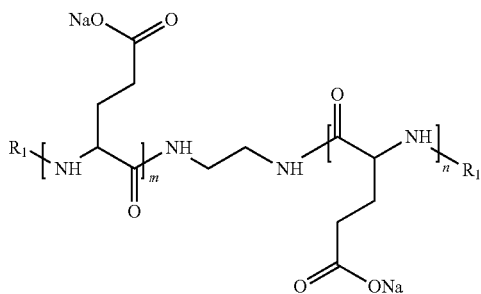<br>i = 0.0812, DP (m + n) = 24<br>$R_1$ = H, pyroglutamate or<br>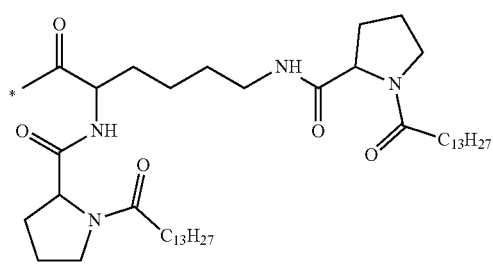 |
| B9 | 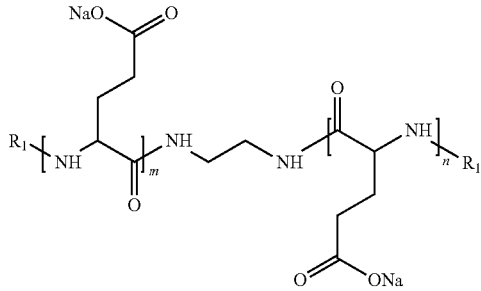<br>i = 0.0833, DP (m + n) = 24<br>$R_1$ = H, pyroglutamate or<br>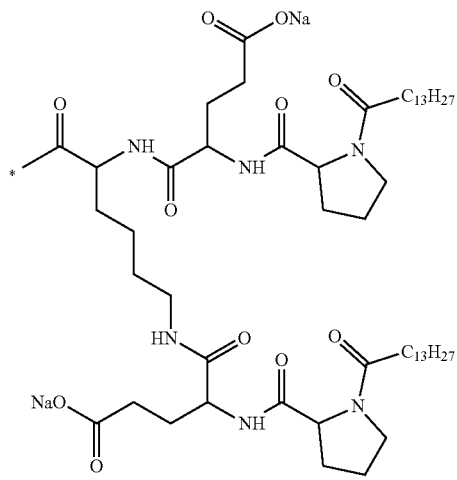 |

| # | CO-POLYAMINO ACIDS BEARING CARBOXYLATE CHARGES AND HYDROPHOBIC RADICALS |
|---|---|
| B13 | 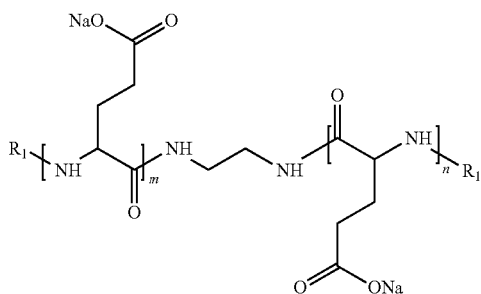<br>i = 0.079, DP (m + n) = 24<br>R₁ = H, pyroglutamate or<br><br>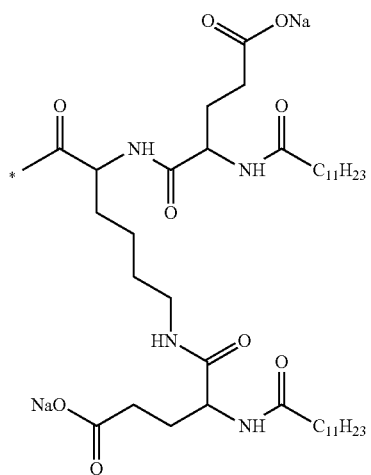 |
| B14 | 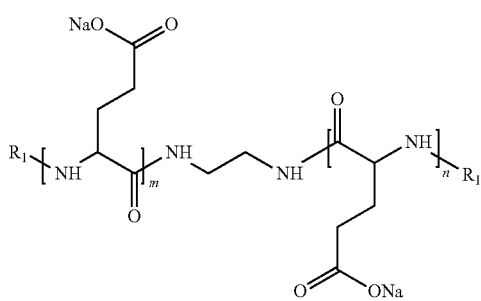<br>i = 0.072, DP (m + n) = 24<br>R₁ = H, pyroglutamate or |

| # | CO-POLYAMINO ACIDS BEARING CARBOXYLATE CHARGES AND HYDROPHOBIC RADICALS |
|---|---|
| | 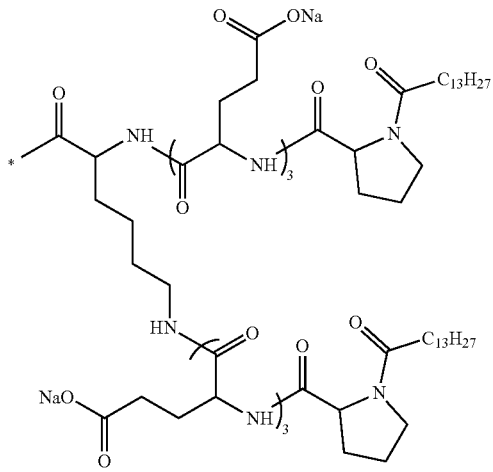 |
| B15 | 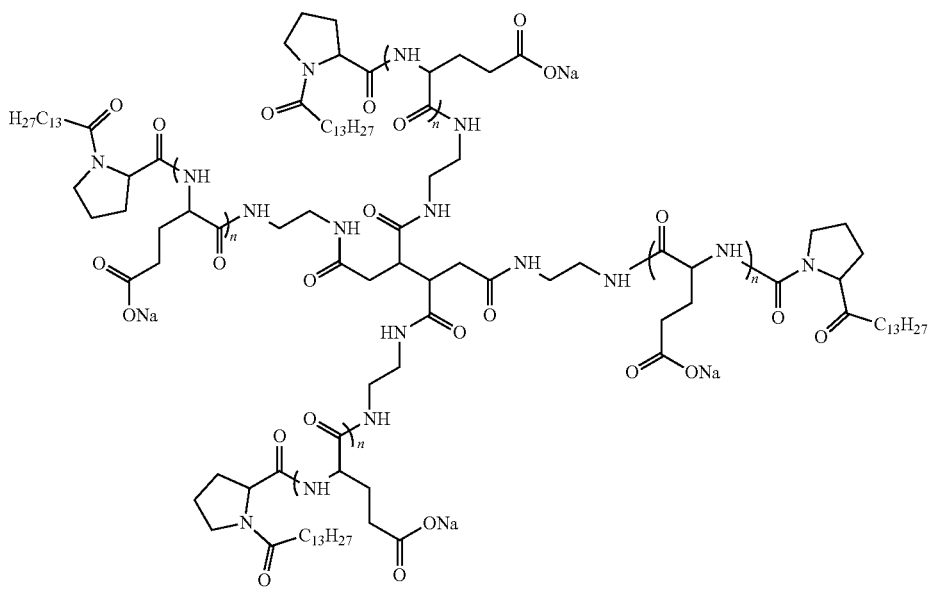
DP (n) = 5.5
i = 3.4 |
| B16 | 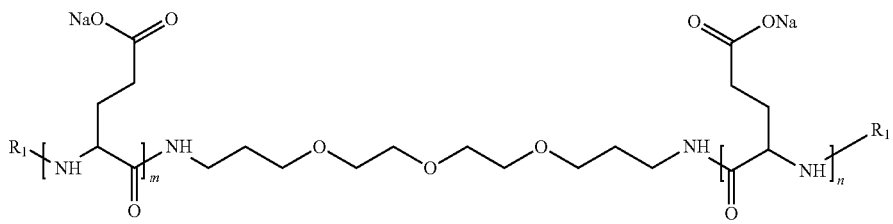
i = 0.078, DP (m + n) = 24
$R_1$ = H, pyroglutamate or |

| # | CO-POLYAMINO ACIDS BEARING CARBOXYLATE CHARGES AND HYDROPHOBIC RADICALS |
|---|---|
| | 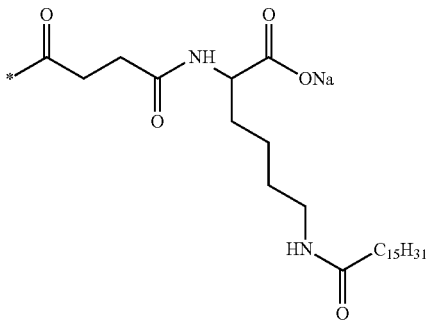 |
| B17 | 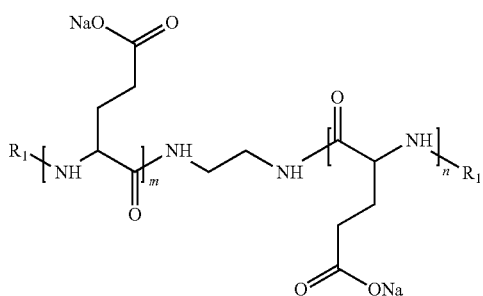<br>i = 0.048, DP (m + n) = 24<br>$R_1$ = H, pyroglutamate or<br>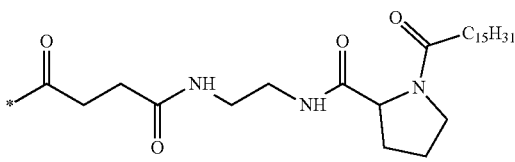 |
| B18 | 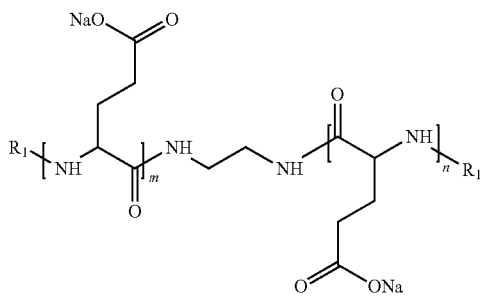<br>i = 0.075, DP (m + n) = 24<br>$R_1$ = H, pyroglutamate or<br>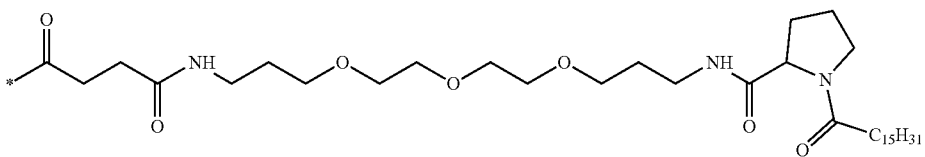 |

| # | CO-POLYAMINO ACIDS BEARING CARBOXYLATE CHARGES AND HYDROPHOBIC RADICALS |
|---|---|
| B19 | 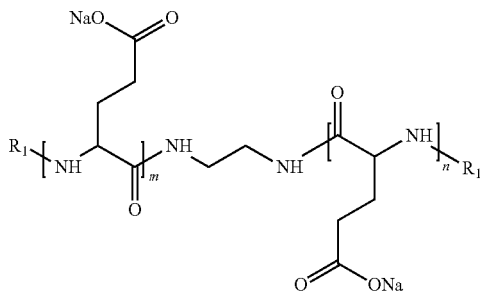<br>i = 0.066, DP (m + n) = 24<br>R₁ = H, pyroglutamate or<br>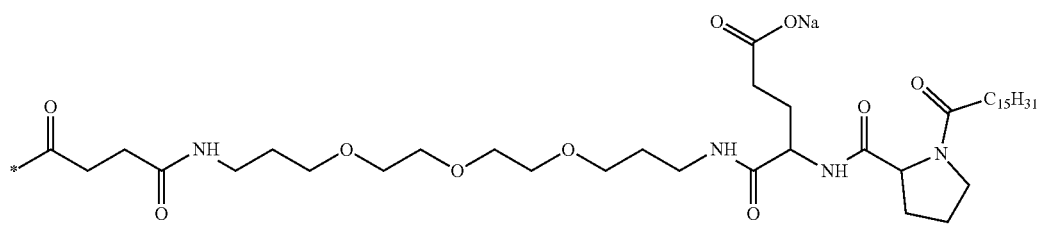 |
| B20 | 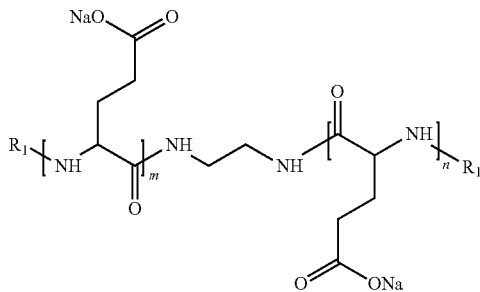<br>i = 0.075, DP (m + n) = 24<br>R₁ = H, pyroglutamate or<br>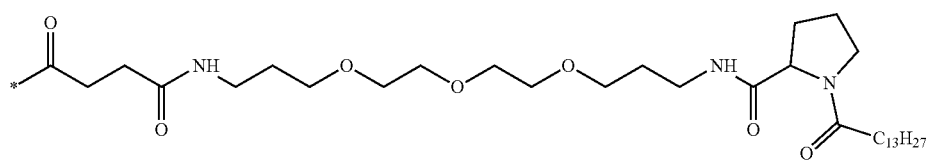 |

| # | CO-POLYAMINO ACIDS BEARING CARBOXYLATE CHARGES AND HYDROPHOBIC RADICALS |
|---|---|
| B21 | 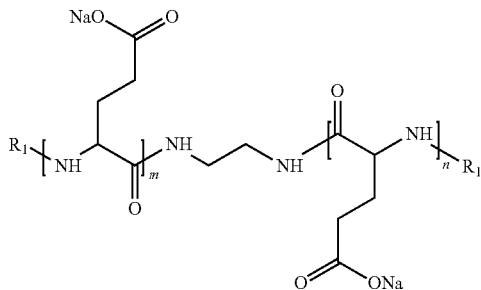<br>i = 0.077, DP (m + n) = 24<br>R₁ = H, pyroglutamate or<br>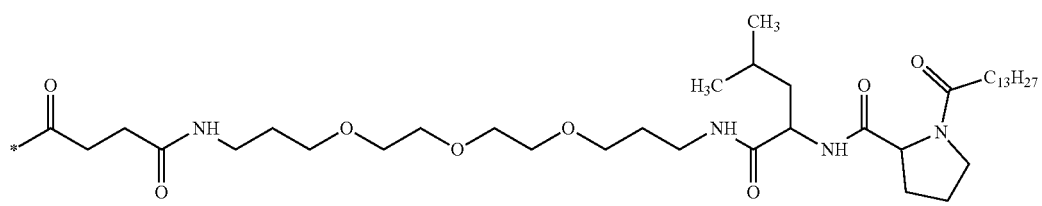 |
| B23 | 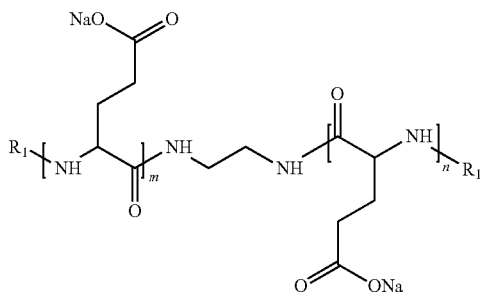<br>i = 0.080, DP (m + n) = 24<br>R₁ = H, pyroglutamate or<br>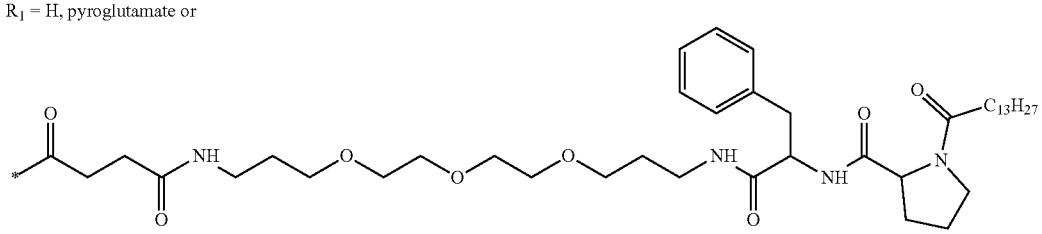 |

| # | CO-POLYAMINO ACIDS BEARING CARBOXYLATE CHARGES AND HYDROPHOBIC RADICALS |
|---|---|
| B24 | 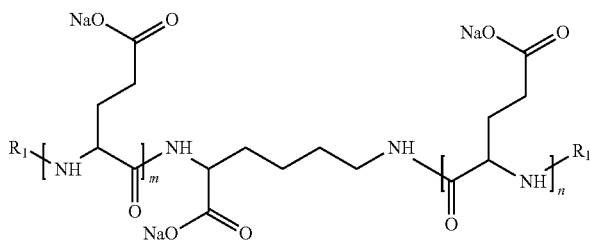<br>i = 0.143, DP (m + n) = 14<br>$R_1$ = H, pyroglutamate or<br>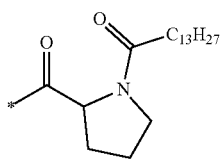 |
| B25 | 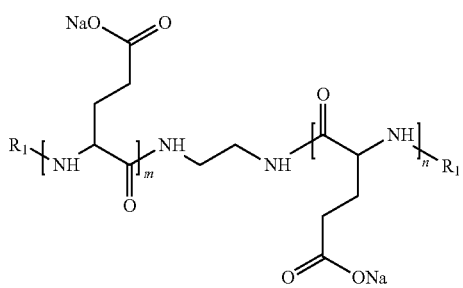<br>i = 0.079, DP (m + n) = 24<br>$R_1$ = H, pyroglutamate or<br>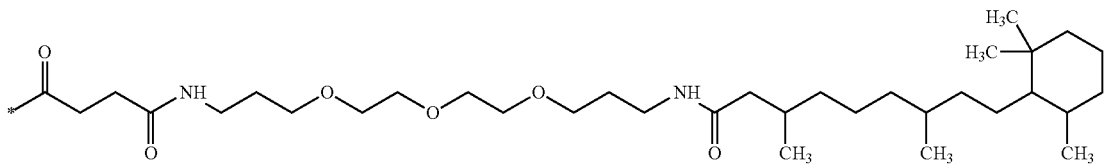 |
| B26 | 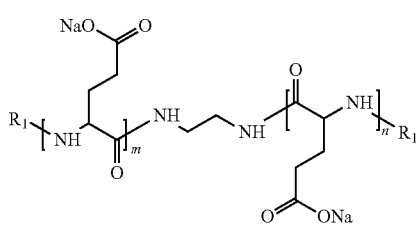<br>i = 0.073, DP (m + n) = 24<br>$R_1$ = H, pyroglutamate or<br>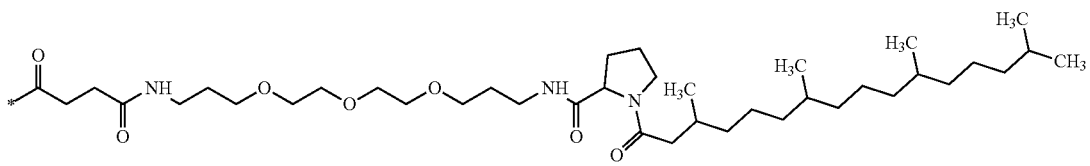 |

| # | CO-POLYAMINO ACIDS BEARING CARBOXYLATE CHARGES AND HYDROPHOBIC RADICALS |
|---|---|
| B27 | 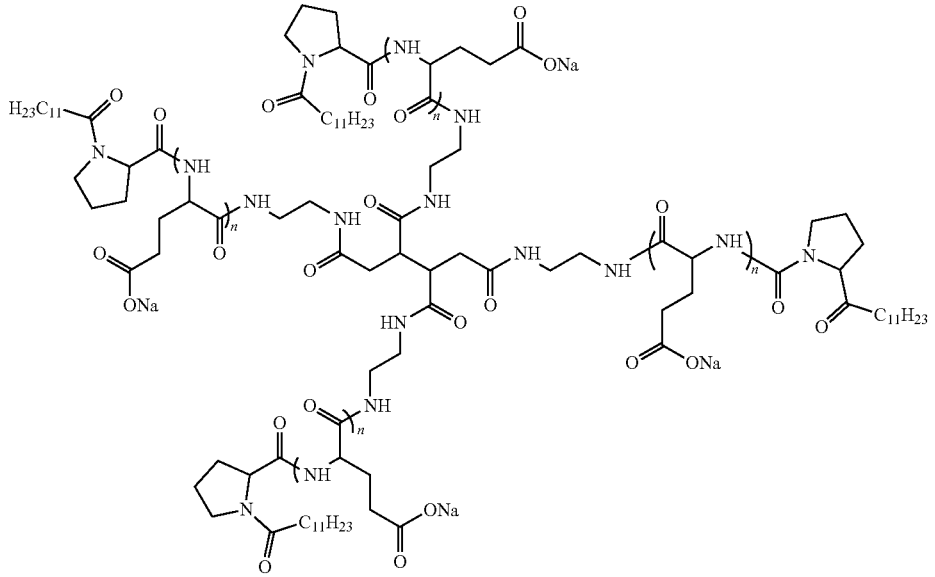<br>DP (n) = 4.75<br>i = 3.7 |
| B28 | 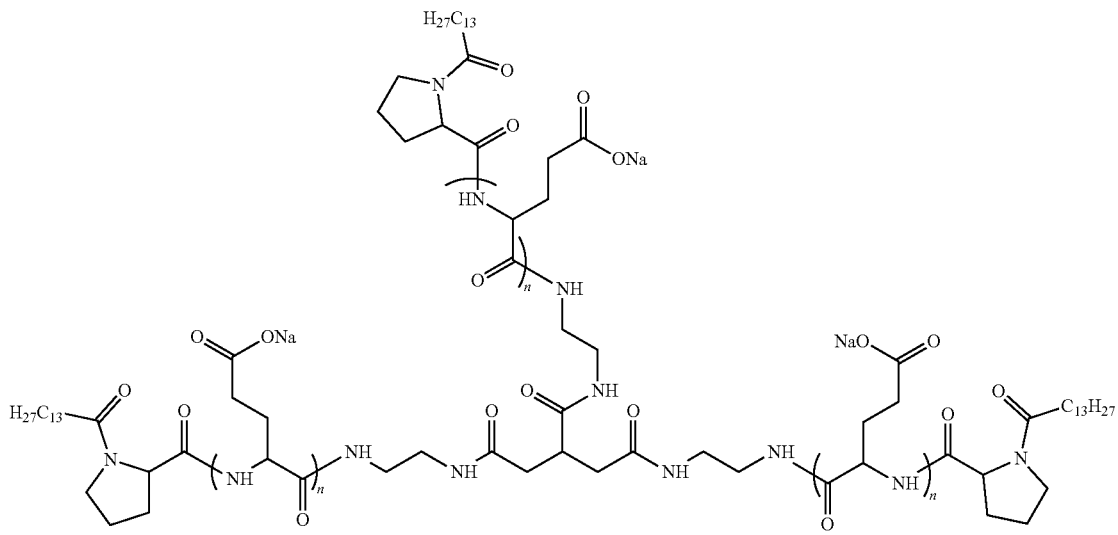<br>DP (n) = 5.15<br>i = 3.0 |
| B29 | 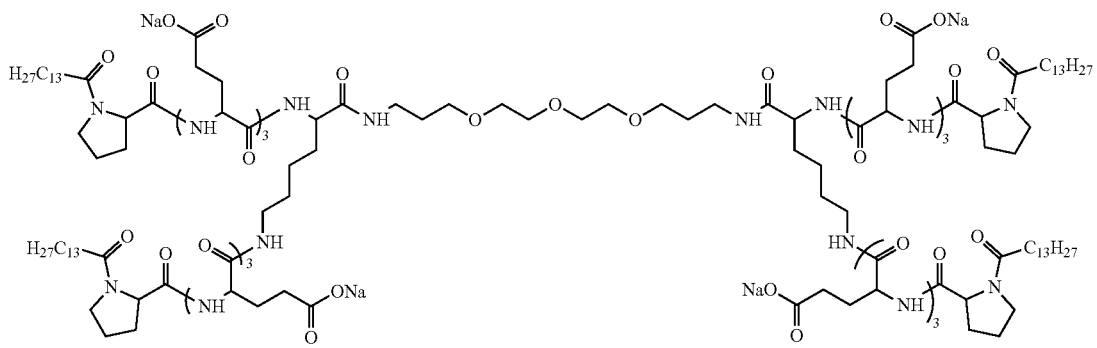 |

| # | CO-POLYAMINO ACIDS BEARING CARBOXYLATE CHARGES AND HYDROPHOBIC RADICALS |
|---|---|
| B30 | 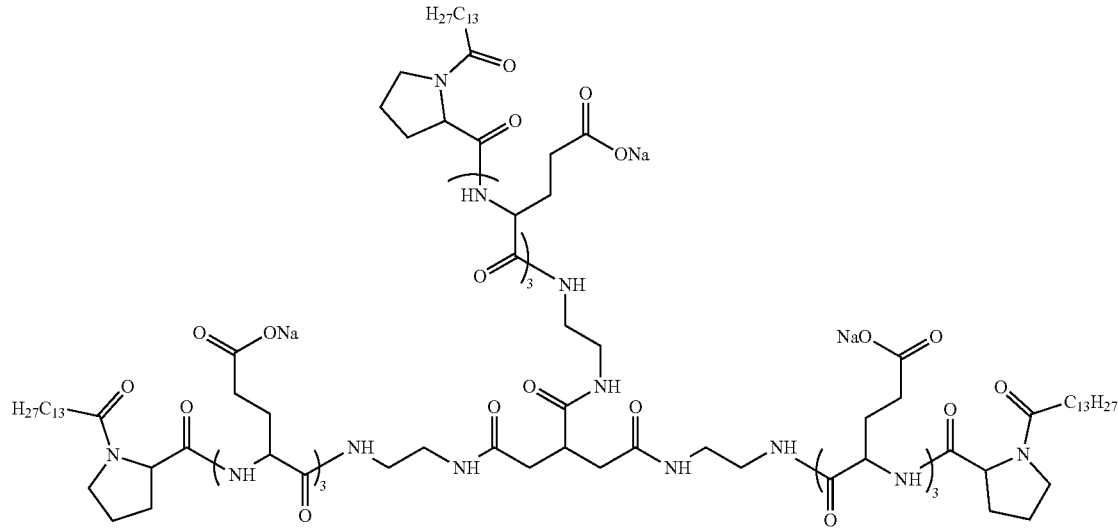 |
| B31 | 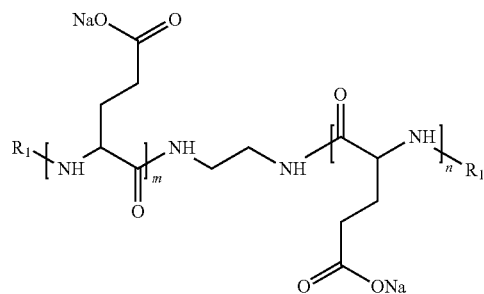<br>i = 0.075, DP (m + n) = 24<br>$R_1$ = H, pyroglutamate or<br>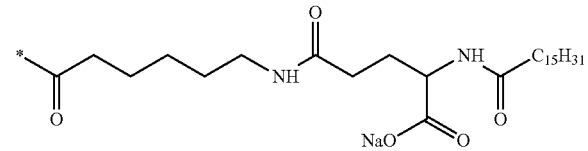 |

EXAMPLE B1

Co-Polyamino Acid B1—Sodium Poly-L-Glutamate Modified at the Extremities thereof by Molecule A1 and having a Number Average Molar Mass (Mn) of 3600 g/mol Co-polyamino acid B1-1: poly-L-benzylglutamate obtained from the polymerization of γ-benzyl-L-glutamate N-carboxyanhydride initiated by ethylenediamine and modified at the extremities thereof by molecule A1.

In a previously oven-dried flask, γ-benzyl-L-glutamate N-carboxyanhydride (34.74 g, 132 mmol) is solubilized in anhydrous DMF (78 mL). The mixture is then stirred until complete dissolution, cooled to 0° C., then ethylene diamine (0.205 g, 3.41 mmol) is introduced rapidly and the medium is stirred at 0° C.

In parallel, molecule A1 (2.26 g, 6.94 mmol) is solubilized in DMF (44 mL), then NHS (0.82 g, 7.12 mmol) and DCC (1.47 g, 7.12 mmol) are added successively. After stirring overnight at ambient temperature, the heterogeneous mixture is filtered on a sintered filter. The filtrate is then added to the polymer solution kept at 0° C. After 24 h, the solution is placed at ambient temperature. After 6 h of stirring, the reaction medium is poured onto diisopropylether (IPE, 1.8 L). The precipitate is filtered on a sintered filter, washed with IPE (3×30 mL) and dried at 30° C. at reduced pressure.

Co-Polyamino Acid B1

Co-polyamino acid B1-1 is diluted in trifluoroacetic acid (TFA, 132 mL), then the solution is cooled to 4° C. A 33% HBr solution in acetic acid (92.5 mL, 0.528 mol) is then added dropwise. The mixture is stirred at ambient temperature for 2 h, then poured dropwise onto a 1:1 (v/v) mixture of diisopropylether and water under stirring (0.8 L). After 2 h of stirring, the heterogeneous mixture is left to stand overnight. The white precipitate is retrieved by filtration, washed with IPE (2×66 mL) then with water (2×66 mL). The solid obtained is then solubilized in water (690 mL) by adjusting the pH to 7 by adding an aqueous solution of 1 N sodium hydroxide. After solubilization, the theoretical concentration is adjusted to 20 g/L theoretical by adding water (310 mL), the solution is filtered on a 0.45 µm filter then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 24.3 mg/g
DP (estimated as per $^1$H NMR): 40
As per $^1$H NMR: i=0.050
The calculated average molar mass of co-polyamino acid B1 is 6719 g/mol.
HPLC-Organic SEC (PEG calibrator): Mn=3600 g/mol.

EXAMPLE B2

Co-Polyamino Acid B2—Sodium Poly-L-Glutamate Modified at the Extremities Thereof by Stearic Acid and Having a Number Average Molar Mass (Mn) of 3400 g/Mol Co-polyamino acid B2-1: poly-L-benzylglutamate obtained from the polymerization of γ-benzyl-L-glutamate N-carboxyanhydride initiated by hexamethylenediamine.

In a previously oven-dried flask, γ-benzyl-L-glutamate N-carboxyanhydride (30.0 g, 114 mmol) is solubilized in anhydrous DMF (67 mL). The mixture is then stirred until complete dissolution, cooled to 0° C., then hexamethylenediamine (0.442 g, 3.8 mmol) is introduced rapidly. After 23 h of stirring at 0° C., a 4 M HCl solution in dioxane (4.7 mL, 18.8 mmol) is added then the reaction medium is poured in 5 min onto a mixture of methanol (94 mL) and IPE (375 mL). The precipitate is filtered on a sintered filter, washed with IPE (2×70 mL) and dried at 30° C. at reduced pressure.

Co-polyamino acid B2-2: poly-L-benzylglutamate modified at the extremities thereof by stearic acid.

To a solution of stearic acid (0.851 g, 2.99 mmol) in DMF (20 mL) at 0° C. are added successively HATU (1.484 g, 3.89 mmol) and DIPEA (1.166 g, 9.02 mmol). The solution is then introduced onto a solution of co-polyamino acid B2-1 (10.0 g) and triethylamine (TEA, 0.309 g, 3.04 mmol) in DMF (110 mL) at 0° C., and the medium is stirred for 18 h from 0° C. to ambient temperature. Dichloromethane (390 mL) is added, the organic phase is washed with 0.1 N HCl aqueous solution (3×190 mL), an aqueous solution saturated with $NaHCO_3$ (2×190 mL), an aqueous solution saturated with NaCl (2×190 mL) followed by water (190 mL). The medium is then poured onto IPE (1.4 L). The precipitate is filtered on a sintered filter, washed with IPE (2×100 mL) and dried at 30° C. at reduced pressure.

Co-Polyamino Acid B2

By means of a similar method to that used for the preparation of co-polyamino acid B1 applied to co-polyamino acid B2-2 (8.80 g, 36.5 mmol), a sodium poly-L-glutamate modified at the extremities thereof with stearic acid is obtained.

Dry extract: 17.9 mg/g
DP (estimated as per $^1$H NMR): 30
As per $^1$H NMR: i=0.0657
The calculated average molar mass of co-polyamino acid B2 is 5174 g/mol.
HPLC-Organic SEC (PEG calibrator): Mn=3400 g/mol.

EXAMPLE B3

Co-Polyamino Acid B3—Sodium Poly-L-Glutamate Modified at the Extremities Thereof by Molecule A2 and Having a Number Average Molar Mass (Mn) of 3000 g/Mol Co-polyamino acid B3-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (0.765 g, 12.73 mmol) and to γ-benzyl-L-glutamate N-carboxyanhydride (80.0 g, 304 mmol), co-polyamino acid B3-1 is obtained.

Co-polyamino acid B3-2: poly-L-benzylglutamate modified at the extremities thereof by molecule A2.

By means of a similar method to that used for the preparation of co-polyamino acid B2-2 applied to co-polyamino acid B3-1 (30.0 g, 5.56 mmol) and to molecule A2 (7.94 g, 12.24 mmol), a poly-L-benzylglutamate modified at the extremities thereof with molecule A2 is obtained.

Co-Polyamino Acid B3

To a solution of co-polyamino acid B3-2 (36.6 g, 133.5 mmol) in N,N-dimethylacetamide (DMAc, 146 mL) is added 5% palladium on alumina (7.3 g), then the solution is placed at 60° C. at 10 bar hydrogen. After leaving overnight, the reaction medium is filtered on a sintered filter then on a 0.2 µm PTFE filter. The filtrate is then placed under stirring before adding water (1.4 L) previously acidified to pH 2 with a 1 N HCl solution (14 mL) dropwise. After placing overnight, the precipitate is filtered on a sintered filter, washed with water (4×110 mL) and dried at 30° C. at reduced pressure.

The solid obtained is then solubilized in water (1.09 L) by adjusting the pH to 7 by adding an aqueous solution of 1 N sodium hydroxide (121 mL). After solubilization, the solution is basified by adding 1 N sodium hydroxide (26 mL) up to a pH of 12. After 2 h, the solution is neutralized by adding 1 N HCl solution (28 mL). The theoretical concentration is adjusted to 12 g/L theoretical by adding water (650 mL) and ethanol (1040 mL) then the solution is filtered on an R53SLP carbon filter (3M) at a rate of 12 mL/min, then on a 0.2 µm PES filter. The solution is then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 21.6 mg/g
DP (estimated as per $^1$H NMR): 24
As per $^1$H NMR: i=0.0808
The calculated average molar mass of co-polyamino acid B3 is 4948 g/mol.
HPLC-Organic SEC (PEG calibrator): Mn=3000 g/mol.

EXAMPLE B4

Co-Polyamino Acid B4—Sodium Poly-L-Glutamate Modified at the Extremities Thereof by Molecule A3 and Having a Number Average Molar Mass (Mn) of 2500 g/Mol Co-polyamino acid B4-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (1.644 g, 27.35 mmol) and to γ-benzyl-L-glutamate N-carboxyanhydride (100.0 g, 380 mmol), co-polyamino acid B4-1 is obtained.

Co-polyamino acid B4-2: poly-L-benzylglutamate modified at the extremities thereof by molecule A3.

By means of a similar method to that used for the preparation of co-polyamino acid B2-2 applied to co-polyamino acid B4-1 (10.0 g, 3.12 mmol) and to molecule A3 (4.412 g, 6.26 mmol), a poly-L-benzylglutamate modified at the extremities thereof with molecule A3 is obtained.

Co-Polyamino Acid B4

By means of a similar method to that used for the preparation of co-polyamino acid B3 applied to co-polyamino acid B4-2 (12.0 g, 37.3 mmol), a sodium poly-L-glutamate modified at the extremities thereof with molecule A3 is obtained.

Dry extract: 21.7 mg/g

DP (estimated as per $^1$H NMR): 14

As per $^1$H NMR: i=0.134

The calculated average molar mass of co-polyamino acid B4 is 3464 g/mol.

HPLC-Organic SEC (PEG calibrator): Mn=2500 g/mol.

EXAMPLE B5

Co-Polyamino Acid B5—Sodium Poly-L-Glutamate Modified at the Extremities Thereof by Molecule A3 and Having a Number Average Molar Mass (Mn) of 2800 g/Mol Co-polyamino acid B5-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (0.95 g, 15.83 mmol) and to γ-benzyl-L-glutamate N-carboxyanhydride (100.0 g, 380 mmol), co-polyamino acid B5-1 is obtained.

Co-polyamino acid B5-2: poly-L-benzylglutamate modified at the extremities thereof by molecule A3.

By means of a similar method to that used for the preparation of co-polyamino acid B2-2 applied to co-polyamino acid B5-1 (20.0 g, 3.71 mmol) and to molecule A3 (5.233 g, 7.42 mmol), a poly-L-benzylglutamate modified at the extremities thereof with molecule A3 is obtained.

Co-Polyamino Acid B5

By means of a similar method to that used for the preparation of co-polyamino acid B1 applied to co-polyamino acid B5-2 (15.6 g, 55.93 mmol), a sodium poly-L-glutamate modified at the extremities thereof with molecule A3 is obtained.

Dry extract: 27.4 mg/g

DP (estimated as per $^1$H NMR): 24

As per $^1$H NMR: i=0.077

The calculated average molar mass of co-polyamino acid B5 is 4956 g/mol.

HPLC-Organic SEC (PEG calibrator): Mn=2800 g/mol.

EXAMPLE B6

Co-Polyamino Acid B6: Sodium Poly-L-Glutamate Modified at the Extremities Thereof by Molecule A4 and Having a Number Average Molar Mass (Mn) of 2900 g Mol Co-polyamino acid B6-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (0.951 g, 15.83 mmol) and to γ-benzyl-L-glutamate N-carboxyanhydride (100.0 g, 380 mmol), co-polyamino acid B6-1 is obtained.

Co-polyamino acid B6-2: poly-L-benzylglutamate modified at the extremities thereof by molecule A4.

By means of a similar method to that used for the preparation of co-polyamino acid B2-2 applied to co-polyamino acid B6-1 (20.0 g, 3.71 mmol) and to molecule A4 (6.649 g, 8.74 mmol), a poly-L-benzylglutamate modified at the extremities thereof with molecule A4 is obtained.

Co-Polyamino Acid B6

By means of a similar method to that used for the preparation of co-polyamino acid B1 applied to co-polyamino acid B6-2 (19.7 g, 69.47 mmol), a sodium poly-L-glutamate modified at the extremities thereof with molecule A4 is obtained.

Dry extract: 28.7 mg/g

DP (estimated as per $^1$H NMR): 24

As per $^1$H NMR: i=0.0812

The calculated average molar mass of co-polyamino acid B6 is 5135 g/mol.

HPLC-Organic SEC (PEG calibrator): Mn=2900 g/mol.

EXAMPLE B9

Co-Polyamino Acid B9—Sodium Poly-L-Glutamate Modified at the Extremities Thereof by Molecule A7 Wherein the Side Chains are Deprotected and Having a Number Average Molar Mass (Mn) of 3200 g/Mol Co-polyamino acid B9-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (0.96 g, 15.94 mmol) and to γ-benzyl-L-glutamate N-carboxyanhydride (100.0 g, 380 mmol), co-polyamino acid B9-1 is obtained.

Co-polyamino acid B9-2: poly-L-benzylglutamate modified at the extremities thereof by molecule A7.

By means of a similar method to that used for the preparation of co-polyamino acid B2-2 applied to co-polyamino acid B9-1 (25.0 g, 4.64 mmol) and to molecule A7 (10.49 g, 9.27 mmol), a poly-L-benzylglutamate modified at the extremities thereof with molecule A7 is obtained.

Co-polyamino acid B9-3: poly-L-benzylglutamate modified at the extremities thereof by molecule A7 wherein the side chains are deprotected.

Co-polyamino acid B9-2 (18.6 g) is solubilized in TFA (100 mL). After 2 h under stirring, the reaction medium is concentrated at reduced pressure.

Co-Polyamino Acid B9

By means of a similar method to that used for the preparation of co-polyamino acid B3 applied to co-polyamino acid B9-3 (18.0 g, 59.0 mmol), a sodium poly-L-glutamate modified at the extremities thereof with molecule A7 is obtained.

Dry extract: 21.8 mg/g

DP (estimated as per $^1$H NMR): 24

As per $^1$H NMR: i=0.0833

The calculated average molar mass of co-polyamino acid B9 is 5776 g/mol.

HPLC-Organic SEC (PEG calibrator): Mn=3200 g/mol.

EXAMPLE B13

Co-Polyamino Acid B13—Sodium Poly-L-Glutamate Modified at the Extremities Thereof by Molecule A11 Wherein the Esters are Deprotected and Having a Number Average Molar Mass (Mn) of 3200 g/Mol Co-polyamino acid B13-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B13-1 is obtained.

Co-polyamino acid B13-2: poly-L-benzylglutamate modified at the extremities thereof by molecule A11.

To a solution of co-polyamino acid B13-1 (12.0 g) in DMF (40 mL) at 0° C. are successively added a solution of molecule A11 (5.88 g, 6.67 mmol) in DMF (20 mL), N-2-hydroxypyridine oxide (HOPO, 0.82 g, 7.34 mmol), N-(3-dimethylaminopropyl)-N'-ethylcarbodiimide (EDC) (1.66 g, 8.68 mmol), followed by DIPEA (0.97 mL, 5.56 mmol). The reaction medium is stirred at 0° C. for 16 h and at 20° C. for 2 h. Dichloromethane (150 mL) is added and the organic phase is washed with a 0.1 N HCl aqueous solution (6×75 mL), dried on Na$_2$SO$_4$ then filtered. The organic phase is then poured onto IPE (600 mL), then left to stand for 18 h. The white precipitate is retrieved by filtration, washed with IPE (2×150 mL) then dried at reduced pressure at 30° C.

Co-polyamino acid B13-3: poly-L-benzylglutamate modified at the extremities thereof by molecule A11 wherein the esters are deprotected Co-polyamino acid B13-2 is solubilized in TFA (60 mL), and the solution is stirred for 2 h at ambient temperature then is poured dropwise onto diisopropylether under stirring (600 mL). After 18 h, the white precipitate is retrieved by filtration, triturated with IPE and dried at reduced pressure.

Co-Polyamino Acid B13

By means of a similar method to that used for the preparation of co-polyamino acid B3 applied to co-polyamino acid B13-3 (14.5 g), a sodium poly-L-glutamate modified at the extremities thereof with molecule A11 wherein the esters are deprotected is obtained.

Dry extract: 18.0 mg/g

DP (estimated as per $^1$H NMR): 24

As per $^1$H NMR: i=0.079

The calculated average molar mass of co-polyamino acid B13 is 5194 g/mol.

HPLC-Organic SEC (PEG calibrator): Mn=3200 g/mol

EXAMPLE B14

Co-Polyamino Acid B14—Sodium Poly-L-Glutamate Modified at the Extremities Thereof by Molecule A12 Wherein the Esters are Deprotected and Having a Number Average Molar Mass (Mn) of 3700 g/Mol Co-polyamino acid B14-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B14-1 is obtained.

Co-polyamino acid B14-2: poly-L-benzylglutamate modified at the extremities thereof by molecule A12

By means of a similar method to that used for the preparation of co-polyamino acid B2-2 applied to molecule A12 (2.67 g, 1.43 mmol) and to co-polyamino acid B14-1 (3.5 g), a poly-L-benzylglutamate modified at the two extremities thereof with molecule A2 is obtained.

Co-polyamino acid B14-3: poly-L-benzylglutamate modified at the extremities thereof by molecule A12 wherein the esters are deprotected By means of a similar method to that used for the preparation of co-polyamino acid B13-3 applied to co-polyamino acid B14-2, a poly-L-benzylglutamate modified at the two extremities thereof with molecule A12 wherein the esters are deprotected is obtained.

Co-Polyamino Acid B14

By means of a similar method to that used for the preparation of co-polyamino acid B3 applied to co-polyamino acid B14-3 (1.97 g), in a hydrogen atmosphere (1 atm, 48 h, 65° C.), a sodium poly-L-glutamate modified at the two extremities thereof with molecule A12 wherein the esters are deprotected is obtained.

Dry extract: 13.2 mg/g

DP (estimated as per $^1$H NMR): 24

As per $^1$H NMR: i=0.072

The calculated average molar mass of co-polyamino acid B14 is 6537 g/mol.

HPLC-Organic SEC (PEG calibrator): Mn=3700 g/mol

EXAMPLE B15

Co-Polyamino Acid B15—Butyltetracarboxylic Acid Substituted with Molecule A13 Wherein the Esters are Deprotected and Having a Number Average Molar Mass (Mn) of 2700 g/Mol Molecule A13

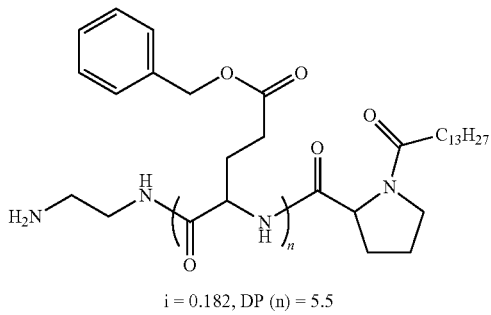

i = 0.182, DP (n) = 5.5

Molecule 31: Product obtained by polymerization of γ-benzyl-L-glutamate N-carboxyanhydride initiated by N-Boc-ethylenediamine.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to −10° C., then the BocEDA solution is introduced rapidly. The reaction medium is stirred at 0° C. for 4 h then a solution of HCl in 1,4-dioxane (3.33 M, 19.8 mL, 65.34 mmol) is added. The reaction medium is stirred at ambient temperature then the solution is poured onto a solution of MeOH/IPE (245 mL/990 mL) cooled by an ice bath. After 62 h of stirring at ambient temperature, the white precipitate is filtered on a sintered filter, washed with IPE (2×160 mL) and dried at 30° C. at reduced pressure.

$^1$H NMR (DMSO-d6, ppm): 1.35 (9H); 1.70-2.10 (10H); 2.26-2.65 (10H); 2.85-3.18 (4H); 3.85 (1H); 4.14-4.42 (4H); 4.87-5.24 (10H); 6.34-6.86 (1H); 7.11-7.56 (25H); 7.90-8.44 (7H); 8.69 (1H).

DP (estimated as per $^1$H NMR): 5.0

The calculated average molar mass of molecule 31 in hydrochloride salt form is 1292.9 g/mol.

Molecule 32: Product obtained by coupling molecule 31 and molecule A1.

Molecule 31 (10.0 g, 7.73 mmol) is solubilized in a mixture of DCM (90 mL) and DIPEA (1.585 g, 9.32 mmol) at 0° C. To this solution are added successively HOPO (1.242 g, 11.18 mmol), molecule A1 (3.335 g, 10.25 mmol) and EDC (2.141 g, 11.17 mmol). After placing under stirring overnight, the reaction medium is washed twice with a 0.1 N HCl solution (2×100 mL), twice with a 5% Na$_2$CO$_3$ aqueous solution (2×100 mL) followed by a saturated NaCl solution (100 mL). The organic phase is dried on Na$_2$SO$_4$, filtered and concentrated at reduced pressure. The residue is solubilized in DCM (30 mL) and the solution is poured onto isopropyl alcohol (600 mL) under stirring at 0° C. The precipitate formed is retrieved by vacuum filtration then vacuum-dried at 30° C.

Yield: 7.58 g (62%)

$^1$H NMR CDCl$_3$, ppm): 0.87 (3H); 1.06-2.76 (58.6H); 3.06-4.45 (12.4H); 4.88-5.25 (10.8H); 5.72-8.40 (34.4H).

DP (estimated as per $^1$H NMR): 5.4

The calculated average molar mass of molecule 32 in hydrochloride salt form is 1651.6 g/mol.

Molecule A13

After solubilizing molecule 32 (5.93 g, 3.59 mmol) in DCM (40 mL), the solution is cooled to 0° C. and TFA (40 mL) is added. The reaction medium is stirred at 0° C. for 3 h then is dry concentrated at reduced pressure at ambient temperature. The residue is taken up with DCM (120 mL) and washed with an aqueous carbonate buffer solution at pH 10.4 (3×240 mL) then by a 0.1 N HCl aqueous solution (2×240 mL). The organic solution is dried on Na$_2$SO$_4$, filtered and concentrated at reduced pressure. A white solid of molecule A13 in hydrochloride salt form is obtained.

Yield: 5.17 g (91%)

$^1$H NMR (TFA-d, ppm): 0.87 (3H); 1.06-1.46 (20H); 1.46-1.68 (2H); 1.68-2.81 (28H); 3.13-4.59 (12.5H); 4.83-5.25 (11H); 7.02-9.13 (37H)

DP (estimated as per $^1$H NMR): 5.5

The calculated average molar mass of molecule A13 in hydrochloride salt form is 1609.8 g/mol.

Co-polyamino acid B15-1: Molecule A13 (3.47 g, 2.16 mmol) is solubilized in DCM (17 mL) then is added successively at 0° C. butyltetracarboxylic acid (BTCA, 115 mg, 0.49 mmol), HOPO (275 mg, 2.48 mmol), DIPEA (377 µL, 2.16 mmol) followed by EDC (473 mg, 2.47 mmol). After placing under stirring overnight at 0° C., the reaction medium is poured onto MeOH (220 mL) under stirring at 0° C. After leaving overnight, the white precipitate is retrieved by vacuum filtration, triturated with cold MeOH then vacuum-dried at 30° C.

Co-Polyamino Acid B15

A solution of co-polyamino acid B15-1 (2.33 g, 0.362 mmol) in DMAc (33 mL) is placed in a hydrogen atmosphere (1 atm) in the presence of 5% palladium on alumina (465 mg) then the solution is heated to 60° C. After leaving overnight, the solution is cooled, filtered on Celite® then the filtrate is poured onto a 15% NaCl solution at pH 2 (500 mL). After leaving overnight, the precipitate is filtered on a sintered filter then washed twice with a 15% NaCl solution (2×8 mL). The solid obtained is then solubilized in water (70 mL) by adjusting the pH to 7 by adding an aqueous solution of 1 N sodium hydroxide. After solubilization, the solution is filtered on a 0.45 µm filter then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 25.8 mg/g $^1$H NMR (D$_2$O, ppm): 0.90 (10.2H); 1.18-1.46 (68H); 1.53-1.9 (6.8H); 1.86-3.04 (101.2H); 3.17-3.80 (20.4H); 4.19-4.68 (22.1H)

DP (estimated as per $^1$H NMR): 5.5

As per $^1$H NMR: i=3.4

The calculated average molar mass of co-polyamino acid B15 is 4261.3 g/mol.

HPLC-Organic SEC (PEG calibrator): Mn=2700 g/mol.

EXAMPLE B16

Co-Polyamino Acid B16—Sodium Poly-L-Glutamate Modified at the Extremities Thereof by Molecule A14 Wherein the Esters are Deprotected and Having a Number Average Molar Mass (Mn) of 3200 g/Mol Co-polyamino acid B16-1: poly-L-benzylglutamate obtained from the polymerization of γ-benzyl-L-glutamate N-carboxyanhydride initiated by 1-amino-4,7,10-trioxa-13-tridecane amine (TOTA).

By means of a similar method to that used for the preparation of co-polyamino acid B2-1 applied to TOTA (13.96 g, 63.37 mmol) and to γ-benzyl-L-glutamate N-carboxyanhydride (400.0 g, 1519 mmol), co-polyamino acid B16-1 is obtained.

Co-Polyamino Acid B16

To a solution of molecule A14 (6.74 g, 13.5 mmol) in DMAc (38 mL) are successively added HOPO (1.65 g, 14.8 mmol), and EDC (3.36 g, 17.6 mmol).

To a solution of co-polyamino acid B16-1 (30.0 g) in DMAc (113 mL) at ambient temperature are successively added DIPEA (1.90 mL, 13.5 mmol) followed by the solution of molecule A14 previously prepared.

After 24 h of stirring at ambient temperature, DMAc (82 mL) is added and the solution is placed at 60° C. under 10 bar hydrogen in the presence of 5% palladium on alumina (7.0 g). After 17 h of reaction, the reaction medium is filtered on a sintered filter then on a 0.2 μm PTFE filter.

The filtrate is placed under stirring, then a 300 g/L sodium carbonate solution (46 mL) followed by acetone (275 mL) are then added successively dropwise. After 3 h, the precipitate is filtered on a sintered filter, washed with acetone (3×70 mL) and dried at reduced pressure.

After solubilizing the solid obtained in water (1.3 L) then diluting with ethanol (0.7 L), the solution is basified by adding 10 N sodium hydroxide (13 mL) until a pH of 13 is obtained. After 3 h of stirring at ambient temperature, the solution is neutralized by adding 1 N HCl solution (190 mL) then the solution is filtered on an R53SLP carbon filter (3M), then on a 0.2 μm PES filter. The solution is then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 21.4 mg/g
DP (estimated as per $^1$H NMR): 24
As per $^1$H NMR: i=0.078
The calculated average molar mass of co-polyamino acid B16 is 4761 g/mol.
HPLC-Organic SEC (PEG calibrator): Mn=3200 g/mol.

EXAMPLE B17

Co-Polyaminoacid B17—Sodium Poly-L-Glutamate Modified at the Two Extremities Thereof by Molecule A15 and Having a Number Average Molar Mass (Mn) of 3200 g/Mol Co-polyamino acid B17-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylenediamine (4.77 g, 79.37 mmol) and to γ-benzyl-L-glutamate N-carboxyanhydride (500.0 g, 1899 mmol), co-polyamino acid B17-1 is obtained.

Co-Polyamino Acid B17

By means of a similar method to that used for the preparation of co-polyamino acid B16 applied to co-polyamino acid B17-1 (15.0 g) and to molecule A 15 (3.45 g) with a saponification step at pH 12 for 50 min, co-polyamino acid B17 is obtained.

Dry extract: 20.3 mg/g
DP (estimated as per $^1$H NMR): 24
As per $^1$H NMR: i=0.048
The calculated average molar mass of co-polyamino acid B17 is 4237 g/mol.
HPLC-Organic SEC (PEG calibrator): Mn=3200 g/mol

EXAMPLE B18

Co-Polyaminoacid B18—Sodium Poly-L-Glutamate Modified at the Two Extremities Thereof by Molecule A16 and Having a Number Average Molar Mass (Mn) of 3150 g/Mol Co-polyamino acid B18-1: poly-L-benzylglutamate obtained from the polymerization of γ-benzyl-L-glutamate N-carboxyanhydride initiated by ethylenediamine.

By means of a similar method to that used for the preparation of co-polyamino acid B2-1 applied to ethylenediamine (4.74 g, 78.89 mmol) and to γ-benzyl-L-glutamate N-carboxyanhydride (498.4 g, 1893 mmol), co-polyamino acid B18-1 is obtained.

Co-Polyamino Acid B18

By means of a similar method to that used for the preparation of co-polyamino acid B17 applied to co-polyamino acid B18-1 (14.0 g) and to molecule A 16 (4.26 g), co-polyamino acid B18 is obtained.

Dry extract: 9.7 mg/g
DP (estimated as per $^1$H NMR): 24
As per $^1$H NMR: i=0.075
The calculated average molar mass of co-polyamino acid B18 is 4839 g/mol.
HPLC-Organic SEC (PEG calibrator): Mn=3150 g/mol

EXAMPLE B19

Co-Polyamino Acid B19—Sodium Poly-L-Glutamate Modified at the Extremities Thereof by Molecule A17 Wherein the Esters are Deprotected and Having a Number Average Molar Mass (Mn) of 3400 g/Mol By means of a similar method to that used for the preparation of co-polyamino acid B16 applied to co-polyamino acid B18-1 (20.39 g) and to molecule A17 (7.553 g), co-polyamino acid B19 is obtained.

Dry extract: 18.6 mg/g
DP (estimated as per $^1$H NMR): 24
As per $^1$H NMR: i=0.066
The calculated average molar mass of co-polyamino acid B19 is 4936 g/mol.
HPLC-Organic SEC (PEG calibrator): Mn=3400 g/mol

EXAMPLE B20

Co-Polyaminoacid B20—Sodium Poly-L-Glutamate Modified at the Two Extremities Thereof by Molecule A18 and Having a Number Average Molar Mass (Mn) of 3200 g/Mol By means of a similar method to that used for the preparation of co-polyamino acid B17 applied to co-polyamino acid B17-1 (12.45 g) and to molecule A18 (3.56 g), co-polyamino acid B20 is obtained.

Dry extract: 16.8 mg/g
DP (estimated as per $^1$H NMR): 24
As per $^1$H NMR: i=0.075
The calculated average molar mass of co-polyamino acid B20 is 4784 g/mol.
HPLC-Organic SEC (PEG calibrator): Mn=3200 g/mol

EXAMPLE B21

Co-Polyaminoacid B21—Sodium Poly-L-Glutamate Modified at the Two Extremities Thereof by Molecule A19 and Having a Number Average Molar Mass (Mn) of 3600 g/Mol By means of a similar method to that used for the preparation of co-polyamino acid B17 applied to co-polyamino acid B17-1 (12.16 g) and to molecule A19 (4.16 g), co-polyamino acid B21 is obtained.
Dry extract: 26.4 mg/g
DP (estimated as per $^1$H NMR): 24
As per $^1$H NMR: i=0.077
The calculated average molar mass of co-polyamino acid B21 is 5023 g/mol.
HPLC-Organic SEC (PEG calibrator): Mn=3600 g/mol

EXAMPLE B23

Co-Polyaminoacid B23—Sodium Poly-L-Glutamate Modified at the Two Extremities Thereof by Molecule A21 and Having a Number Average Molar Mass (Mn) of 3350 g/Mol By means of a similar method to that used for the preparation of co-polyamino acid B17 applied to co-polyamino acid B17-1 (18.68 g) and to molecule A21 (7.03 g), co-polyamino acid B23 is obtained.
Dry extract: 23.2 mg/g
DP (estimated as per $^1$H NMR): 24
As per $^1$H NMR: i=0.080
The calculated average molar mass of co-polyamino acid B23 is 5140 g/mol.
HPLC-Organic SEC (PEG calibrator): Mn=3350 g/mol

EXAMPLE B24

Co-Polyaminoacid B24—Sodium Poly-L-Glutamate Modified at the Extremities Thereof by Molecule A1 and Having a Number Average Molar Mass (Mn) of 2300 g/Mol Co-polyamino acid B24-1: poly-L-benzylglutamate obtained from the polymerization of γ-benzyl-L-glutamate N-carboxyanhydride initiated by molecule 4 and modified at the extremities thereof by molecule A1.
To a suspension of molecule 4 (9.92 mmol) in anhydrous DMF (80 mL) cooled to 0° C. is rapidly added a solution of γ-benzyl-L-glutamate N-carboxyanhydride (26.11 g, 99.2 mmol) in anhydrous DMF (20 mL) at 0° C. After 24 h of stirring at 0° C., a freshly prepared solution of molecule A1 (16.1 g, 49.6 mmol), HATU (18.9 g, 49.6 mmol) and DIPEA (8.64 mL, 49.6 mmol) in DMF (80 mL) is added to the medium and the mixture is stirred from 0° C. to 25° C. for 3.5 h. The resin is filtered, washed successively with DMF (3×100 mL), isopropanol (1×100 mL) and DCM (3×100 mL). The resin obtained is then treated with an 80:20 DCM/HFIP mixture (120 mL). After 30 min of stirring at ambient temperature, the resin is filtered and washed successively with DCM (3×100 mL). The solvents are evaporated at reduced pressure to produce co-polyamino acid B24-1
Co-Polyamino Acid B24
By means of a similar method to that used for the hydrogenation step of co-polyamino acid B16 applied to co-polyamino acid B24-1 (27.4 g), with a saponification step at pH 12 for 50 min but without the carbofiltration step, co-polyamino acid B24 is obtained.
Dry extract: 14.1 mg/g
DP (estimated as per $^1$H NMR): 14
As per $^1$H NMR: i=0.143
The calculated average molar mass of co-polyamino acid B24 is 2899 g/mol.
HPLC-Organic SEC (PEG calibrator): Mn=2300 g/mol.

EXAMPLE B25

Co-Polyaminoacid B25—Sodium Poly-L-Glutamate Modified at the Extremities Thereof by Molecule A22 and Having a Number Average Molar Mass (Mn) of 3050 g/Mol By means of a similar method to that used for the preparation of co-polyamino acid B17 applied to co-polyamino acid B18-1 (30.0 g) and molecule A22 (8.56 g) using a four-fold greater quantity of 300 g/L sodium carbonate solution to precipitate the polymer after the hydrogenolysis step, co-polyamino acid B25 is obtained.
Dry extract: 23.7 mg/g
DP (estimated as per $^1$H NMR): 24
As per $^1$H NMR: i=0.074
The calculated average molar mass of co-polyamino acid B25 is 4743 g/mol.
HPLC-Organic SEC (PEG calibrator): Mn=3050 g/mol

EXAMPLE B26

Co-Polyaminoacid B26—Sodium Poly-L-Glutamate Modified at the Two Extremities Thereof by Molecule A23 and Having a Number Average Molar Mass (Mn) of 3400 g/Mol By means of a similar method to that used for the preparation of co-polyamino acid B25 applied to co-polyamino acid B17-1 (25.78 g) and to molecule A23 (8.27 g), co-polyamino acid B21 is obtained.
Dry extract: 11.8 mg/g
DP (estimated as per $^1$H NMR): 24
As per $^1$H NMR: i=0.073
The calculated average molar mass of co-polyamino acid B21 is 4902 g/mol.
HPLC-Organic SEC (PEG calibrator): Mn=3400 g/mol

EXAMPLE B27

Co-Polyamino Acid B27—Butyltetracarboxylic Acid Substituted with Molecule A24 Wherein the Esters are Deprotected and Having a Number Average Molar Mass (Mn) of 2500 g/Mol

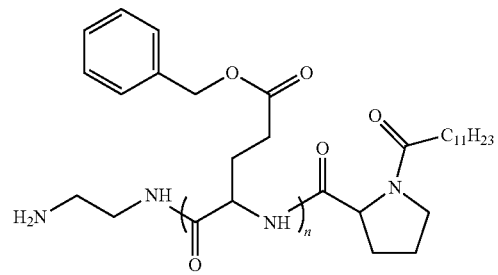

Molecule A24 i = 0.21, DP (n) = 4.75

Molecule 53: Product obtained by polymerization of γ-benzyl-L-glutamate N-carboxyanhydride initiated by N-Boc-ethylenediamine then capped with molecule 2.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to −10° C., then the BocEDA solution is introduced rapidly. The reaction medium is stirred at 0° C. for 3 h then are introduced successively DMF (100 mL), molecule 2 (26.73 g, 89.88 mmol), HOPO (9.99 g, 89.88 mmol) and EDC (17.23 g, 89.88 mmol). The reaction mixture is stirred at 0° C. for 1 h, from 0° C. to 20° C. for 2 h then at 20° C. for 16 h. It is then poured onto a 1:12-propanol/H$_2$O solution (10 V) under stirring. After 3 h, the white precipitate is filtered on a sintered filter, washed with a 1:12-propanol/H$_2$O mixture (2×360 mL) and dried at 30° C. at reduced pressure.

Yield: 70 g (71%)

$^1$H NMR (TFA-d, ppm): 0.99 (3H); 1.34-1.59 (16H); 1.68-2.85 (36H); 3.52-3.62 (2H); 3.79-3.99 (4H); 4.70-4.92 (5.75H); 5.20-5.38 (9.5H); 7.36-7.52 (23.75H).

DP (estimated as per $^1$H NMR): 4.75

The calculated average molar mass of molecule 53 is 1481.0 g/mol.

Molecule A24

By means of a similar method to that used for the preparation of molecule A13 applied to molecule 53 (34.00 g, 22.96 mmol), a white solid of molecule A24 in hydrochloride salt form is obtained.

Yield: 29.40 g (90%)

$^1$H NMR (TFA-d, ppm): 1.00 (3H); 1.35-1.61 (16H); 1.79-1.93 (2H); 2.05-2.90 (25H); 3.53-3.65 (2H); 3.79-4.02 (4H); 4.74-4.94 (5.75H); 5.20-5.43 (9.5H); 7.32-7.58 (23.75H).

DP (estimated as per $^1$H NMR): 4.75

The calculated average molar mass of molecule A13 in hydrochloride salt form is 1417.2 g/mol.

Co-Polyamino Acid B27-1:

By means of a similar method to that used for the preparation of co-polyamino acid B15-1 applied to molecule A24 (11.9 g, 8.40 mmol) and to BTCA (0.41 g, 1.75 mmol) in solution in DMF, a white solid is obtained after drying at 30° C. at reduced pressure.

Co-Polyamino Acid B27

By means of a similar method to that used for the preparation of co-polyamino acid B15 applied to co-polyamino acid B27-1 (9.31 g, 1.64 mmol), under hydrogen pressure (6 bar) and with a saponification step at pH 12 for 1 h prior to the ultrafiltration step, co-polyamino acid B27 is obtained.

Dry extract: 19.9 mg/g

DP (estimated as per $^1$H NMR): 4.75

As per $^1$H NMR: i=3.7

The calculated average molar mass of co-polyamino acid B27 is 4085.8 g/mol.

HPLC-Organic SEC (PEG calibrator): Mn=2500 g/mol.

EXAMPLE B28

Co-Polyamino Acid B28—Tricarballylic Acid Substituted with Molecule A25 Wherein the Esters are Deprotected and Having a Number Average Molar Mass (Mn) of 2200 g/Mol

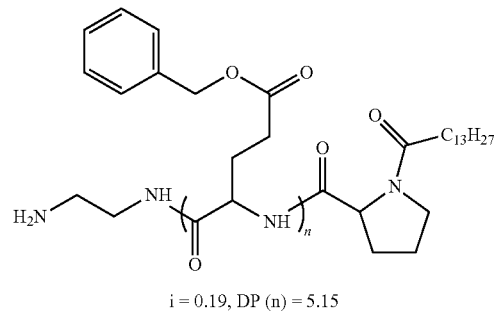

Molecule A25 i = 0.19, DP (n) = 5.15

Molecule 54: Product obtained by polymerization of γ-benzyl-L-glutamate N-carboxyanhydride initiated by N-Boc-ethylenediamine then capped with molecule A1.

By means of a similar method to that used for the preparation of molecule 53 applied to BocEDA (6.00 g, 37.45 mmol), to γ-benzyl-L-glutamate N-carboxyanhydride (39.44 g, 150.00 mmol) and to molecule A1 (14.63 g, 44.94 mmol), a white solid of molecule 54 is obtained.

Yield: 23.71 g (40%)

$^1$H NMR CDCl$_3$, ppm): 0.87 (3H); 1.12-2.76 (57.6H); 3.06-4.50 (12.15H); 4.90-5.25 (10.3H); 5.91-8.49 (32.9H).

DP (estimated as per $^1$H NMR): 5.15

The calculated average molar mass of molecule 54 is 1596.8 g/mol.

Molecule A25

By means of a similar method to that used for the preparation of molecule A13 applied to molecule 54 (23.29 g, 14.59 mmol), a translucent solid of molecule A25 in hydrochloride salt form is obtained.

Yield: 19.08 g (85%)

$^1$H NMR CDCl$_3$, ppm): 0.87 (3H); 1.17-1.32 (20H); 1.48-1.63 (2H); 1.69-2.78 (29.6H); 3.15-4.40 (12.15H); 4.89-5.18 (10.3H); 7.06-9.13 (31.9H).

DP (estimated as per $^1$H NMR): 5.15

The calculated average molar mass of molecule A25 in hydrochloride salt form is 1533.1 g/mol.

Co-Polyamino Acid B28-1:

By means of a similar method to that used for the preparation of co-polyamino acid B15-1 applied to molecule A25 (3.93 g, 2.56 mmol) and to tricarballylic acid (TCA, 125.2 mg, 0.71 mmol) in solution in DMF, a white solid is obtained after drying at 30° C. at reduced pressure.

Co-Polyamino Acid B28

By means of a similar method to that used for the preparation of co-polyamino acid B15 applied to co-polyamino acid B28-1 (2.98 g, 0.65 mmol) and with a saponification step at pH 12 for 1 h prior to the ultrafiltration step, co-polyamino acid B28 is obtained.

Dry extract: 25.8 mg/g

DP (estimated as per $^1$H NMR): 5.15

As per $^1$H NMR: i=3.0

The calculated average molar mass of co-polyamino acid B28 is 3559.2 g/mol.

HPLC-Organic SEC (PEG calibrator): Mn=2200 g/mol.

EXAMPLE B29

Co-Polyamino Acid B29—4,7,10-Trioxa-1,13-Tridecanediamine (TOTA) Substituted with Molecule A12 Wherein the Esters are Deprotected and Having a Number Average Molar Mass (Mn) of 2000 g/Mol Co-Polyamino Acid B29-1:

To a solution of molecule A12 (3.70 g, 1.98 mmol) in chloroform (31 mL) at ambient temperature are added successively HOBt (304 mg, 1.98 mmol) and 4,7,10-trioxa-1,13-tridecanediamine (TOTA, 208 mg, 0.94 mmol). The mixture is cooled to 0° C. then EDC (380 mg, 1.98 mmol) is added. The reaction medium is stirred for 15 min at 0° C. followed by 18 h at ambient temperature. The organic phase is washed with a 0.1 N NaOH aqueous solution (2×28 mL), and the organic phase is dried on $Na_2SO_4$, filtered and concentrated at reduced pressure. The solid obtained is solubilized in $CHCl_3$ (40 mL) and the solution is added dropwise to IPE (400 mL) under stirring. The suspension is placed in an ice bath without stirring for 17 h. The suspension is centrifuged at 3200 rpm for 10 min at 25° C. The colorless supernatant is removed and the solid obtained is concentrated at reduced pressure.

Yield: 4.59 g (quant.)

$^1$H NMR $CDCl_3$, ppm): 0.88 (12H); 1.12-1.58 (192H); 1.58-2.17 (48H); 2.17-2.62 (44H); 3.08 (2H); 3.13-3.38 (6H); 3.48 (4H); 3.53-3.66 (12H); 3.74-3.83 (4H); 3.92 (2H); 4.00-4.12 (4H); 4.12-4.33 (10H); 4.37 (2H); 6.72-6.84 (4H); 7.06 (2H); 7.31 (2H); 7.52 (2H); 7.82 (2H); 7.94 (2H); 8.57-8.69 (4H).

Co-Polyamino Acid B29

Molecule B29-1 (3.67 g, 0.93 mmol) is solubilized in TFA (11.5 mL) and the solution is stirred at ambient temperature for 6 h. The solution is poured dropwise onto IPE (18 mL) at 5° C. then water (18 mL) is added. The suspension is placed in an ice bath under stirring for 15 h. The suspension is filtered and triturated with IPE (10 mL) and water (2×10 mL). The residue is dried at reduced pressure then solubilized in a 1 N NaOH solution (56 mL) with regular addition of 1 N NaOH to maintain the pH at 7. The solution is diluted to 20 g/L theoretical with water then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 8.0 mg/g

The calculated average molar mass of co-polyamino acid B29 is 3520 g/mol.

HPLC-Organic SEC (PEG calibrator): Mn=2000 g/mol.

EXAMPLE B30

Co-Polyamino Acid B30—Tricarballylic Acid Substituted with Molecule A26 Wherein the Esters are Deprotected and Having a Number Average Molar Mass (Mn) of 2100 g/Mol Co-polyamino acid B30-1: By means of a similar method to that used for the preparation of co-polyamino acid B15-1 applied to molecule A26 (10.87 g, 11.33 mmol) and to tricarballylic acid (TCA, 0.605 g, 3.43 mmol) in solution in DMF, a white solid is obtained after 2 consecutive precipitations of the product in solution in DMF in a 50:50 $H_2O$/MeCN mixture (10V), filtration, trituration with a 50:50 $H_2O$/MeCN mixture followed by drying at reduced pressure at 30° C.

Co-Polyamino Acid B30

Co-polyamino acid B30-1 (8.53 g, 2.95 mmol) is solubilized in TFA (30 mL), and the solution is stirred for 3 h at ambient temperature then is poured dropwise onto water under stirring (300 mL). After 1 h, the white precipitate is retrieved by filtration, triturated with water and dried at reduced pressure. The solid obtained is then solubilized in water (350 mL) by adjusting the pH to 7 adding an aqueous solution of 1 N sodium hydroxide. The solution is filtered on a 0.2 μm filter then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 28.8 mg/g

The molar mass of co-polyamino acid B30 is 2585 g/mol.

HPLC-Organic SEC (PEG calibrator): Mn=2100 g/mol.

EXAMPLE B31

Co-Polyamino Acid B31—Sodium Poly-L-Glutamate Modified at the Extremities Thereof by Molecule A27 Wherein the Esters are Deprotected and Having a Number Average Molar Mass (Mn) of 3800 g/Mol By means of a similar method to that used for the preparation of co-polyamino acid B16 applied to co-polyamino acid B18-1 (28.6 g) and to molecule A27 (6.799 g), co-polyamino acid B31 is obtained.

Dry extract: 20.5 mg/g

DP (estimated as per $^1$H NMR): 24

As per $^1$H NMR: i=0.075

The calculated average molar mass of co-polyamino acid B31 is 4591 g/mol.

HPLC-Organic SEC (PEG calibrator): Mn=3800 g/mol

Part C: Compositions

EXAMPLE C1

Preparation of a 0.6 mg/mL Pramlintide Solution Containing m-Cresol (29 mM) and Glycerin (174 mM) at pH 6.6

A 5 mg/mL concentrated pramlintide solution is prepared by dissolving pramlintide in powder form purchased from Ambiopharm. This solution is added to a concentrated solution of excipients (m-cresol, glycerin) so as to obtain the aimed final concentration. The final pH is adjusted to pH 6.6 by adding NaOH/HCl.

EXAMPLE C2

Preparation of a 0.6 mg/mL Pramlintide Solution Containing Co-Polyamino Acid B6, m-Cresol (29 mM) and Glycerin (174 mM) at pH 6.6

A concentrated solution of co-polyamino acid B6 and excipients is prepared by adding concentrated solutions of excipients (m-cresol, glycerin) to a concentrated solution of co-polyamino acid B6.

A 5 mg/mL concentrated pramlintide solution at pH 4 is added to this concentrated solution of co-polyamino acid B6 and excipients so as to obtain the final compositions 2-1 to 2-5 (Table 1). The final pH is adjusted to pH 6.6 by adding NaOH/HCl.

TABLE 1

Compositions and visual appearance of pramlintide solutions at pH 6.6 at different co-polyamino acid B6 concentrations.

| Solution | B6/pramlintide ratio mol/mol | Co-polyamino acid B6 concentration mg/mL | mM | Visual appearance of solution |
|---|---|---|---|---|
| C1 | — | — | — | Clear |
| C2-1 | 1.5 | 1.2 | 0.23 | Clear |
| C2-2 | 2 | 1.6 | 0.30 | Clear |
| C2-3 | 2.5 | 2.0 | 0.38 | Clear |
| C2-4 | 3 | 2.3 | 0.46 | Clear |
| C2-5 | 4 | 3.1 | 0.61 | Clear |

EXAMPLE C3

Preparation of a 0.6 mg/mL Pramlintide Solution Containing Different Co-Polyamino Acids According to the Invention, m-Cresol (29 mM) and Glycerin (174 mM) at pH 6.6

By means of a similar protocol to that described in example C2, 0.6 mg/mL pramlintide solutions containing different co-polyamino acids according to the invention, m-cresol (29 mM) and glycerin (174 mM) at pH 6.6, C3-1 to C3-26 are obtained.

TABLE 2a

Compositions and visual appearance of 0.6 mg/mL pramlintide solutions at pH 6.6 in the presence of different co-polyamino acids.

| Solution | Co-polyamino acid | Co-polyamino acid concentration mg/mL | mM | Ratio of co-polyamino acid/ pramlintide mol/mol | Visual appearance of solution |
|---|---|---|---|---|---|
| C3-1 | B2 | 3.9 | 0.75 | 5 | clear |
|  |  | 7.9 | 1.5 | 10 | clear |
|  |  | 11.8 | 2.28 | 15 | clear |
| C3-2 | B3 | 7.5 | 1.5 | 10 | clear |
|  |  | 11.3 | 2.3 | 15 | clear |
| C3-3 | B5 | 1.5 | 0.3 | 2 | clear |
|  |  | 2.3 | 0.45 | 3 | clear |
|  |  | 3 | 0.6 | 4 | clear |
| C3-4 | B4 | 5.3 | 1.53 | 10 | clear |
| C3-6 | B9 | 1.8 | 0.3 | 2 | clear |
|  |  | 2.6 | 0.46 | 3 | clear |
| C3-7 | B16 | 6.2 | 1.3 | 8 | clear |
| C3-8 | B17 | 5.6 | 1.2 | 8 | clear |
| C3-9 | B19 | 6.4 | 1.3 | 8 | clear |
| C3-10 | B20 | 11.2 | 2.3 | 15 | clear |
| C3-11 | B21 | 3.9 | 0.76 | 5 | clear |
| C3-13 | B23 | 4.0 | 0.76 | 5 | clear |
| C3-14 | B24 | 4.4 | 1.5 | 10 | clear |
| C3-15 | B25 | 3.8 | 0.8 | 5 | clear |
| C3-16 | B26 | 2.6 | 0.52 | 3 | clear |
| C3-17 | B1 | 15.3 | 2.28 | 15 | clear |
| C3-18 | B14 | 2.1 | 0.30 | 2 | clear |
| C3-19 | B14 | 2.9 | 0.42 | 3 | clear |
| C3-20 | B19 | 6 | 1.21 | 8 | clear |
| C3-21 | B23 | 12 | 2.31 | 15 | clear |
| C3-22 | B27 | 3.1 | 0.76 | 5 | clear |
| C3-23 | B28 | 1.1 | 0.3 | 2 | clear |
| C3-24 | B29 | 1.1 | 0.3 | 2 | clear |

TABLE 2a-continued

Compositions and visual appearance of 0.6 mg/mL pramlintide solutions at pH 6.6 in the presence of different co-polyamino acids.

| Solution | Co-polyamino acid | Co-polyamino acid concentration mg/mL | mM | Ratio of co-polyamino acid/ pramlintide mol/mol | Visual appearance of solution |
|---|---|---|---|---|---|
| C3-25 | B30 | 0.8 | 0.3 | 2 | clear |
| C3-26 | B31 | 10.5 | 2.3 | 15 | clear |

EXAMPLE C4

Preparation of a 0.6 mg/mL Pramlintide and 100 IU/mL Human Insulin Solution Containing m-Cresol (29 mM), Glycerin (174 mM) and Zinc Chloride (229 μM) at pH 6.6

The 5 mg/mL concentrated pramlintide solution C1 is added to a concentrated solution of excipients (m-cresol, glycerin, zinc chloride). A 500 IU/mL human insulin solution is prepared by dissolving human insulin in powder form purchased from Amphastar. This solution is added to the concentrated solution of Pramlintide and excipients so as to obtain the sought final concentration. The final pH is adjusted to pH 6.6 by adding NaOH/HCl.

EXAMPLE C5

Preparation of a 0.6 mg/mL Pramlintide and 100 IU/mL Human Insulin Solution Containing Co-Polyamino Acid B6, m-Cresol (29 mM), Glycerin (174 mM) and Zinc Chloride (229 μM) at pH 6.6

A concentrated solution of co-polyamino acid B6 and excipients is prepared by adding concentrated solutions of excipients (m-cresol, glycerin, zinc chloride) to a concentrated solution of co-polyamino acid B6.

A 5 mg/mL concentrated pramlintide solution at pH 4 followed by a 500 IU/mL human insulin solution are added to the concentrated solution of co-polyamino acid B6 and excipients so as to obtain the sought final composition (Table 3). The final pH is adjusted to pH 6.6 by adding NaOH/HCl.

Solutions C5-1 to C5-5 are prepared according to the above protocol.

TABLE 3

Compositions and visual appearance of 0.6 mg/mL pramlintide and human insulin solutions at pH 6.6 at different co-polyamino acid B6 concentrations.

| Solution | B6/pramlintide ratio mol/mol | Co-polyamino acid B6 concentration mg/mL | mM | Visual appearance of solution |
|---|---|---|---|---|
| C4 | — | — | — | Turbid |
| C5-1 | 1.5 | 1.2 | 0.23 | Clear |
| C5-2 | 2 | 1.6 | 0.30 | Clear |
| C5-3 | 2.5 | 2.0 | 0.38 | Clear |
| C5-4 | 3 | 2.3 | 0.46 | Clear |
| C5-5 | 4 | 3.1 | 0.61 | Clear |

EXAMPLE C6

Preparation of a 0.6 mg/mL Pramlintide and 100 IU/mL Human Insulin Solution Containing Different Co-Polyamino Acids According to the Invention, m-Cresol (29 mM), Glycerin (174 mM) and Zinc Chloride (229 µM) at pH 6.6

By means of a similar method to example C5, a 0.6 mg/mL pramlintide and 100 IU/mL human insulin solution containing a co-polyamino acid according to the invention, m-cresol (29 mM), glycerin (174 mM) and zinc chloride (229 µM) at pH 6.6 is obtained.

Solutions C6-1 to 3 and C6-6 to C6-9 are prepared according to the above protocol.

TABLE 4a

Compositions and visual appearance of 0.6 mg/mL pramlintide and 100 IU/mL human insulin solutions at pH 6.6 in the presence of different co-polyamino acids.

| Solution | Co-polyamino acid | Co-polyamino acid concentration mg/mL | mM | Ratio of co-polyamino acid/ pramlintide mol/mol | Visual appearance of solution |
|---|---|---|---|---|---|
| C6-1 | B2 | 3.9 | 0.75 | 5 | clear |
|  |  | 7.9 | 1.5 | 10 | clear |
| C6-2 | B3 | 7.5 | 1.5 | 10 | clear |
|  |  | 11.3 | 2.30 | 15 | clear |
| C6-3 | B5 | 1.5 | 0.3 | 2 | clear |
|  |  | 2.3 | 0.45 | 3 | clear |
|  |  | 3 | 0.6 | 4 | clear |
| C6-6 | B9 | 1.8 | 0.3 | 2 | clear |
|  |  | 2.6 | 0.46 | 3 | clear |
| C6-7 | B1 | 15.3 | 2.28 | 15 | clear |
| C6-8 | B14 | 2.9 | 0.42 | 3 | clear |
| C6-9 | B23 | 9.6 | 1.8 | 12 | clear |
| C6-10 | B27 | 3.1 | 0.76 | 5 | clear |
| C6-11 | B28 | 1.6 | 0.46 | 3 | clear |
| C6-12 | B29 | 1.6 | 0.46 | 3 | clear |
| C6-13 | B30 | 1.2 | 0.46 | 3 | clear |
| C6-14 | B31 | 13.8 | 3 | 20 | clear |

EXAMPLE C7

Preparation of a 0.6 mg/mL Pramlintide Solution Containing Co-Polyamino Acid B2, M-Cresol (29 mM), Glycerin (174 mM), Sodium Chloride and Optionally Zinc Chloride at pH 6.6

A concentrated solution of co-polyamino acid B2 and excipients is prepared by adding concentrated solutions of excipients (m-cresol, glycerin, NaCl, zinc chloride) to a concentrated solution of co-polyamino acid B2.

A 5 mg/mL concentrated pramlintide solution at pH 4 is added to this concentrated solution of co-polyamino acid B2 and excipients so as to obtain the final compositions C7-1 to C7-10 (Table 5). The final pH is adjusted to pH 6.6 by adding NaOH/HCl.

TABLE 5

Compositions and visual appearance of 0.6 mg/mL pramlintide solutions at pH 6.6 in the presence of co-polyamino acid B2, and optionally sodium chloride and zinc chloride.

| Solution | Co-polyamino acid | Co-polyamino acid concentration mg/mL | mM | Ratio of co-polyamino acid/pramlintide | [NaCl] (mM) | [ZnCl$_2$] (mM) | Visual appearance of solution |
|---|---|---|---|---|---|---|---|
| C7-1 | B2 | 2.4 | 0.46 | 3 | 50 | — | clear |
| C7-2 | B2 | 2.4 | 0.46 | 3 | 100 | — | clear |
| C7-3 | B2 | 2.4 | 0.46 | 3 | 50 | 0.5 | clear |
| C7-4 | B2 | 2.4 | 0.46 | 3 | 50 | 1 | clear |
| C7-5 | B2 | 2.4 | 0.46 | 3 | — | 1 | clear |

TABLE 5a

Compositions and visual appearance of 0.6 mg/mL pramlintide solutions at pH 6.6 in the presence of co-polyamino acid B2, sodium chloride and optionally zinc chloride.

| Solution | Co-polyamino acid | Co-polyamino acid concentration mg/mL | mM | Ratio of co-polyamino acid/pramlintide | [NaCl] (mM) | [ZnCl$_2$] (mM) | Visual appearance |
|---|---|---|---|---|---|---|---|
| C7-6 | B2 | 6.3 | 1.2 | 8 | 25 | — | clear |
| C7-7 | B2 | 4.7 | 0.9 | 6 | 25 | 1 | clear |
| C7-8 | B2 | 3.9 | 0.76 | 5 | 50 | — | clear |
| C7-10 | B2 | 2.4 | 0.46 | 3 | 100 | — | clear |

EXAMPLE C8

Preparation of a 0.6 mg/mL Pramlintide Solution Containing Different Co-Polyamino Acids According to the Invention, M-Cresol (29 mM), Glycerin (174 mM), NaCl and Zinc Chloride at pH 6.6

By means of a similar protocol to that described in example C7, 0.6 mg/mL pramlintide solutions containing different co-polyamino acids according to the invention, m-cresol (29 mM) and glycerin (174 mM), optionally sodium chloride and zinc chloride at pH 6.6, C8-1 to C8-4 and C8-9a, C8-10a and C8-11 are obtained.

TABLE 6a

Compositions and visual appearance of 0.6 mg/mL pramlintide solutions at pH 6.6 in the presence of different co-polyamino acids, sodium chloride and optionally zinc chloride.

| Solution | Co-polyamino acid | Co-polyamino acid concentration mg/mL | mM | Ratio of co-polyamino acid/pramlintide | [NaCl] (mM) | [ZnCl$_2$] (mM) | Visual appearance of solution |
|---|---|---|---|---|---|---|---|
| C8-1 | B1 | 15.3 | 2.28 | 15 | 100 | — | clear |
| C8-2 | B1 | 15.3 | 2.28 | 15 | 100 | 1 | clear |
| C8-3 | B1 | 15.3 | 2.28 | 15 | 100 | 2 | clear |
| C8-4 | B3 | 11.3 | 2.3 | 15 | 100 | — | clear |
| C8-9a | B20 | 11.2 | 2.3 | 15 | 25 | 1 | clear |
| C8-10a | B21 | 3.9 | 0.76 | 5 | 25 | — | clear |
| C8-11 | B21 | 3.9 | 0.76 | 5 | 25 | 1 | clear |

EXAMPLE C8a

Preparation of a 0.6 mg/mL Pramlintide Solution Containing Different Co-Polyamino Acids According to the Invention, M-Cresol (29 mM), Glycerin (174 mM) and NaCl (50 mM) at pH 6.6

By means of a similar protocol to that described in example C7, 0.6 mg/mL pramlintide solutions containing different co-polyamino acids according to the invention, m-cresol (29 mM) and glycerin (174 mM), sodium chloride at pH 6.6, C8a-1 to C8a-10 are obtained.

TABLE 6c

Compositions and visual appearance of 0.6 mg/mL pramlintide solutions at pH 6.6 in the presence of different co-polyamino acids, sodium chloride.

| Solution | Co-polyamino acid | Co-polyamino acid concentration mg/mL | mM | Ratio of co-polyamino acid/pramlintide | [NaCl] (mM) | Visual appearance |
|---|---|---|---|---|---|---|
| C8a-1 | B16 | 6.2 | 1.3 | 8 | 50 | clear |
| C8a-2 | B17 | 2.8 | 0.61 | 4 | 50 | clear |
| C8a-3 | B19 | 6.4 | 1.3 | 8 | 50 | clear |
| C8a-4 | B20 | 6.0 | 1.2 | 8 | 25 | clear |
| C8a-7 | B23 | 4.0 | 0.76 | 5 | 25 | clear |
| C8a-8 | B24 | 2.2 | 0.76 | 5 | 50 | clear |
| C8a-9 | B14 | 2.1 | 0.30 | 2 | 25 | clear |
| C8a-10 | B19 | 6 | 1.21 | 8 | 50 | clear |

EXAMPLE C9

Preparation of a 0.6 mg/mL Pramlintide and 100 IU/mL Human Insulin Solution Containing Co-Polyamino Acid B2, M-Cresol (29 mM), Glycerin (174 mM), Sodium Chloride (50 mM) and Zinc Chloride (1 mM)

A concentrated solution of co-polyamino acid B2 and excipients is prepared by adding concentrated solutions of excipients (m-cresol, glycerin, sodium chloride, zinc chloride) to a concentrated solution of co-polyamino acid B2.

A 5 mg/mL concentrated pramlintide solution at pH 4 followed by a 500 IU/mL human insulin solution are added to this concentrated solution of co-polyamino acid B2 and excipients so as to obtain the sought final composition. The final pH is adjusted to pH 6.6 by adding NaOH/HCl.

Solution C9 is prepared according to the above protocol.

EXAMPLE C10

Preparation of a 0.6 mg/mL Pramlintide and 100 IU/mL Human Insulin Solution Containing Different Co-Polyamino Acids According to the Invention, M-Cresol (29 mM), Glycerin (174 mM), and Different Sodium Chloride and Zinc Chloride Concentrations By means of a similar method to example C9, 0.6 mg/mL pramlintide and 100 IU/mL human insulin solutions containing different co-polyamino acids according to the invention, m-cresol (29 mM), glycerin (174 mM), sodium chloride and zinc chloride at pH 6.6 are obtained.

Solutions C9 and C10-1 to C10-7 are prepared according to the above protocol.

TABLE 7a

Compositions and visual appearance of 0.6 mg/mL pramlintide and 100 IU/mL insulin solutions at pH 6.6 in the presence of different co-polyamino acids, sodium chloride and zinc chloride.

| Solution | Co-polyamino acid | Co-polyamino acid concentration mg/mL | mM | Ratio of co-polyamino acid/pramlintide | [NaCl] (mM) | [ZnCl$_2$] (mM) | Visual appearance of solution |
|---|---|---|---|---|---|---|---|
| C9    | B2  | 2.4  | 0.46 | 3  | 50  | 1*  | clear |
| C10-1 | B1  | 15.3 | 2.28 | 15 | 100 | —*  | clear |
| C10-2 | B1  | 15.3 | 2.28 | 15 | 100 | 1*  | clear |
| C10-3 | B1  | 15.3 | 2.28 | 15 | 100 | 2*  | clear |
| C10-4 | B3  | 11.3 | 2.3  | 15 | 100 | —*  | clear |
| C10-5 | B3  | 11.3 | 2.3  | 15 | 100 | 1*  | clear |
| C10-6 | B19 | 6    | 1.21 | 8  | 50  | —*  | clear |
| C10-7 | B23 | 6    | 1.15 | 8  | 25  | —*  | clear |

*composition comprising 0.23 mM of ZnCl$_2$ from the 100 IU/mL human insulin solution

EXAMPLE C11

Results of Visual Observations on Mixture and Fibrillation Measurements by ThT

Principle

The poor stability of a peptide may give rise to the formation of amyloid fibrils, defined as organized macromolecular structures. These may potentially result in gel formation in the sample.

The thioflavin T (ThT) fluorescence monitoring test is used to analyze the physical stability of the solutions. Thioflavin is a small molecular probe having a characteristic fluorescence signature when it binds to amyloid type fibrils (Naiki et al. (1989) Anal. BioChem. 177, 244-249; LeVine (1999) Methods. Enzymol. 309, 274-284).

This method makes it possible to monitor fibril formation for low ThT concentrations in undiluted solutions. This monitoring is carried out under accelerated stability conditions: under stirring and at 37° C.

Experimental Conditions

The samples were prepared just before starting measurement. The preparation of each composition is described in the associated example. Thioflavin T was added in the composition using a concentrated stock solution so as to induce a negligible dilution of the composition. The Thioflavin T concentration in the composition is 2 µM.

A 150 µL volume of the composition was introduced into a well of a 96-well plate. Each composition was analyzed in three tests (triplicate) in the same plate. The plate was sealed with transparent film so to prevent the evaporation of the composition.

This plate was then placed in the enclosure of a plate reader (EnVision 2104 Multilabel, Perkin Elmer). The temperature is set to 37° C., and lateral stirring of 960 rpm with 1 mm amplitude is applied.

A fluorescence intensity reading in each well is carried out with an excitation wavelength of 442 nm, and an emission wavelength of 482 nm over time.

The fibrillation process is conveyed by a significant increase in fluorescence after an interval known as the latent period.

For each well, this interval was determined graphically as the intersection between the baseline of the fluorescence signal and the slope of the fluorescence curve as a function of time determined during the initial significant increase in fluorescence. The value of the latent period reported corresponds to the mean of the latent period measurements made on three wells.

An example of a graphic determination is shown in FIG. 1.

In this FIGURE, the determination of the latent period (LT) by monitoring the fluorescence of Thioflavin T is represented graphically, on a curve having on the y-axis the fluorescence value (in a.u arbitrary units) and on the x-axis the time in minutes.

EXAMPLE CA1

Stability of 0.6 mg/mL Pramlintide Solutions at pH 6.6 in the Presence of Co-Polyamino Acid B6 at Different Concentrations

TABLE 8

Lag time measurement by ThT of solutions C1 and C2-1 to C2-5.

| Solution | B6/pramlintide ratio mol/mol | Co-polyamino acid B6 concentration mg/mL | mM | Lag time (h) |
|---|---|---|---|---|
| C1   | —   | —   | —    | 1   |
| C2-1 | 1.5 | 1.2 | 0.23 | >20 |
| C2-2 | 2   | 1.6 | 0.30 | >60 |
| C2-3 | 2.5 | 2.0 | 0.38 | >60 |
| C2-4 | 3   | 2.3 | 0.46 | >60 |
| C2-5 | 4   | 3.1 | 0.61 | >60 |

The pramlintide solution at pH 6.6 (C1) devoid of co-polyamino acid has a short lag time; the lag times of the solutions containing co-polyamino acid B6 are greater.

EXAMPLE CA2

Stability of 0.6 mg/ml Pramlintide Solutions at pH 6.6 in the Presence of Different Co-Polyamino Acids TABLE 9a Lag time measurement by ThT of compositions C3-1 to C3-4 and C3-6, C3-15 and 16.

| Solution | Co-polyamino acid | Co-polyamino acid concentration mg/mL | mM | Ratio of co-polyamino acid/pramlintide mol/mol | Lag time (h) |
|---|---|---|---|---|---|
| C3-1 | B2 | 3.9 | 0.75 | 5 | 5 > t > 3 |
|  |  | 7.9 | 1.5 | 10 | 10 > t > 7 |
|  |  | 11.8 | 2.28 | 15 | >30 |
| C3-2 | B3 | 7.5 | 1.5 | 10 | >2 |
|  |  | 11.3 | 2.3 | 15 | 5 > t > 4 |
| C3-3 | B5 | 1.5 | 0.3 | 2 | >10 |
|  |  | 2.3 | 0.45 | 3 | >30 |
|  |  | 3 | 0.6 | 4 | >50 |
| C3-4 | B4 | 5.3 | 1.53 | 10 | >40 |
| C3-6 | B9 | 1.8 | 0.3 | 2 | >20 |
|  |  | 2.6 | 0.46 | 3 | >50 |
| C3-15 | B25 | 3.8 | 0.8 | 5 | >30 |
| C3-16 | B26 | 2.6 | 0.52 | 3 | >30 |
| C3-22 | B27 | 3.1 | 0.76 | 5 | >30 |
| C3-23 | B28 | 1.1 | 0.3 | 2 | >30 |
| C3-24 | B29 | 1.1 | 0.3 | 2 | >45 |
| C3-25 | B30 | 0.8 | 0.3 | 2 | >40 |

The pramlintide solution at pH 6.6 (C1) devoid of co-polyamino acid has a short lag time. The co-polyamino acids according to the invention make it possible to obtain lag times greater than 2 h under the test conditions.

EXAMPLE CA3

Stability of 0.6 mg/ml Pramlintide and 100 IU/mL Human Insulin Solutions at pH 6.6 in the Presence of Co-Polyamino Acid B6 at Different Concentrations

TABLE 10 lag time measurement by ThT of compositions C5-1 to C5-5.

| Solution | B6/pramlintide ratio mol/mol | Co-polyamino acid B6 concentration mg/mL | mM | Lag time (h) |
|---|---|---|---|---|
| C4 | — | — | — | * |
| C5-1 | 1.5 | 1.2 | 0.23 | >1 |

TABLE 10-continued lag time measurement by ThT of compositions C5-1 to C5-5.

| Solution | B6/pramlintide ratio mol/mol | Co-polyamino acid B6 concentration mg/mL | mM | Lag time (h) |
|---|---|---|---|---|
| C5-2 | 2 | 1.6 | 0.30 | >5 |
| C5-3 | 2.5 | 2.0 | 0.38 | >10 |
| C5-4 | 3 | 2.3 | 0.46 | >10 |
| C5-5 | 4 | 3.1 | 0.61 | >10 |

* lag time not measured due to turbid solution

One 0.6 mg/ml pramlintide and 100 IU/mL human insulin solution at pH 6.6 devoid of co-polyamino acid is turbid (C4). The clear 0.6 mg/ml pramlintide and 100 IU/ml human insulin solutions at pH 6.6 in the presence of co-polyamino acid B6 have lag times greater than 1 h at a molar ratio of B6/pramlintide of 1.5, potentially greater than 10 h for molar ratios of B6/pramlintide greater than 2.5.

EXAMPLE CA4

Stability of 0.6 mg/ml Pramlintide and 100 IU/mL Human Insulin Solutions at pH 6.6 in the Presence of Different Co-Polyamino Acids TABLE 11a Lag time measurement by ThT of compositions C6-1 to C6-3 and C6-6.

| Solution | Co-polyamino acid | Co-polyamino acid concentration mg/mL | mM | Ratio of co-polyamino acid/pramlintide mol/mol | Lag time (h) |
|---|---|---|---|---|---|
| C6-1 | B2 | 3.9 | 0.75 | 5 | 5 > t > 3 |
|  |  | 7.9 | 1.5 | 10 | >5 |
| C6-2 | B3 | 7.51.4 | 1.50.15 | 10 | >3 |
| C6-3 | B5 | 1.5 | 0.3 | 2 | >3 |
|  |  | 2.3 | 0.45 | 3 | >5 |
|  |  | 3 | 0.6 | 4 | >5 |
| C6-6 | B9 | 1.8 | 0.3 | 2 | >2 |
|  |  | 2.6 | 0.46 | 3 | >5 |

The pramlintide and human insulin solution at pH 6.6 (C4) is turbid. The co-polyamino acids make it possible to obtain lag times greater than 2 h under the test conditions.

EXAMPLE CA5

Stability of 0.6 mg/mL Pramlintide Solutions Containing Co-Polyamino Acid B2, M-Cresol (29 mM), Glycerin (174 mM), Optionally Sodium Chloride and Zinc Chloride at pH 6.6

TABLE 12

Lag time measurement by ThT of compositions C3-1 and C7-1 to C7-5

| Solution | Co-polyamino acid | Co-polyamino acid concentration mg/mL | Co-polyamino acid concentration mM | Ratio of co-polyamino acid/pramlintide | [NaCl] (mM) | [ZnCl$_2$] (mM) | Lag time (h) |
|---|---|---|---|---|---|---|---|
| C3-1 | B2 | 3.9 | 0.75 | 5 | — | — | 5 > t > 3 |
| C7-1 | B2 | 2.4 | 0.46 | 3 | 50 | — | >15 |
| C7-2 | B2 | 2.4 | 0.46 | 3 | 100 | — | 35 > t > 25 |
| C7-3 | B2 | 2.4 | 0.46 | 3 | 50 | 0.5 | >25 |
| C7-4 | B2 | 2.4 | 0.46 | 3 | 50 | 1 | >40 |
| C7-5 | B2 | 2.4 | 0.46 | 3 | — | 1 | >5 |

The pramlintide solution at pH 6.6 (C1) devoid of co-polyamino acid has a short lag time; adding a salt alone or in combination with zinc chloride to the solutions containing co-polyamino acid B2 makes it possible to obtain markedly greater lag times than solution C3-1 containing B2/pramlintide devoid of salt and zinc.

EXAMPLE CA5a

Stability of 0.6 mg/mL Pramlintide Solutions Containing Co-Polyamino Acid B2, M-Cresol (29 mM), Glycerin (174 mM), Optionally Sodium Chloride and Zinc Chloride at pH 6.6

TABLE 12a

Lag time measurement by ThT of compositions C3-1 and C7-2, C7-4 and C7-6 to C7-8.

| Solution | Co-polyamino acid | Co-polyamino acid concentration mg/mL | Co-polyamino acid concentration mM | Ratio of co-polyamino acid/pramlintide | [NaCl] (mM) | [ZnCl$_2$] (mM) | Lag time (h) |
|---|---|---|---|---|---|---|---|
| C3-1 | B2 | 7.9 | 1.5 | 10 | — | — | 10 > t > 7 |
| C7-6 | B2 | 6.3 | 1.2 | 8 | 25 | — | >30 |
| C7-7 | B2 | 4.7 | 0.9 | 6 | 25 | 1 | >30 |
| C7-8 | B2 | 3.9 | 0.76 | 5 | 50 | — | >30 |
| C7-4 | B2 | 2.4 | 0.46 | 3 | 50 | 1 | >40 |
| C7-2 | B2 | 2.4 | 0.46 | 3 | 100 | — | >30 |

Adding salt alone or in combination with zinc chloride in the solutions containing B2 makes it possible to lower the ratio of co-polyamino acid B2/pramlintide and obtain lag times greater than 30 h.

EXAMPLE CA6

Stability of 0.6 mg/mL Pramlintide Solutions Containing Different Co-Polyamino Acids According to the Invention, M-Cresol (29 mM), Glycerin (174 mM), Optionally NaCl and Zinc Chloride at pH 6.6

TABLE 13a

Lag time measurement by ThT of compositions C8-1 to C8-4, C8-9a, C8-10a, C8-11 and C3-2, C3-10, C3-11 and C3-17.

| Solution | Co-polyamino acid | Co-polyamino acid concentration mg/mL | mM | Ratio of co-polyamino acid/pramlintide | [NaCl] (mM) | [ZnCl$_2$] (mM) | Lag time (h) |
|---|---|---|---|---|---|---|---|
| C3-17 | B1 | 15.3 | 2.28 | 15 | — | — | <1 |
| C8-1 | B1 | 15.3 | 2.28 | 15 | 100 | — | >3 |
| C8-2 | B1 | 15.3 | 2.28 | 15 | 100 | 1 | >10 |
| C8-3 | B1 | 15.3 | 2.28 | 15 | 100 | 2 | >14 |
| C3-2 | B3 | 11.3 | 2.3 | 15 | — | — | <5 |
| C8-4 | B3 | 11.3 | 2.3 | 15 | 100 | — | >20 |
| C3-10 | B20 | 11.2 | 2.3 | 15 | — | — | <5 |
| C8-9a | B20 | 11.2 | 2.3 | 15 | 25 | 1 | >30 |
| C3-11 | B21 | 3.9 | 0.76 | 5 | — | — | <6 |
| C8-10a | B21 | 3.9 | 0.76 | 5 | 25 | — | >20 |
| C8-11 | B21 | 3.9 | 0.76 | 5 | 25 | 1 | >30 |

Adding salt alone or in combination with zinc chloride in the solutions containing a co-polyamino acid makes it possible to increase the lag times significantly compared to those obtained with solutions free from salt or zinc.

EXAMPLE CA6a

Stability of 0.6 mg/mL Pramlintide Solutions Containing Different Co-Polyamino Acids According to the Invention, M-Cresol (29 mM), Glycerin (174 mM) and Optionally NaCl (25 or 50 mM) at pH 6.6

TABLE 13c

Lag time measurement by ThT of compositions C3-7 to C3-9, C3-13 to C3-14, C3-18, C8a-1 to C8a-3 and C8a-7 to C8a-9.

| Solution | Co-polyamino acid | Co-polyamino acid concentration mg/mL | mM | Ratio of co-polyamino acid/pramlintide | [NaCl] (mM) | Lag time (h) |
|---|---|---|---|---|---|---|
| C3-7 | B16 | 6.2 | 1.3 | 8 | — | <10 |
| C8a-1 | B16 | 6.2 | 1.3 | 8 | 50 | >30 |
| C3-8 | B17 | 5.6 | 1.2 | 8 | — | <15 |
| C8a-2 | B17 | 2.8 | 0.61 | 4 | 50 | >30 |
| C3-9 | B19 | 6.4 | 1.3 | 8 | — | <6 |
| C8a-3 | B19 | 6.4 | 1.3 | 8 | 50 | >30 |
| C3-13 | B23 | 4.0 | 0.76 | 5 | — | <15 |
| C8a-7 | B23 | 4.0 | 0.76 | 5 | 25 | >30 |
| C3-14 | B24 | 4.4 | 1.5 | 10 | — | <10 |
| C8a-8 | B24 | 2.2 | 0.76 | 5 | 50 | >30 |
| C3-18 | B14 | 2.1 | 0.3 | 2 | — | <35 |
| C8a-9 | B14 | 2.1 | 0.3 | 2 | 25 | >60 |

Adding salt (25 or 50 mM) in the solutions containing co-polyamino acid/pramlintide makes it possible to lower the ratio of co-polyamino acid/pramlintide and obtain lag times greater than 30 h.

Example CA7: Physical stability of 0.6 mg/mL pramlintide and 100 IU/mL human insulin solutions containing different co-polyamino acids according to the invention, m-cresol (29 mM), glycerin (174 mM), and different sodium chloride and zinc chloride concentrations TABLE 14a Lag time measurement by ThT of compositions C6-1, C6-2, C6-7, C9 and C10-1 to C10-5.

| Solution | Co-polyamino acid | Co-polyamino acid concentration mg/mL | mM | Ratio of co-polyamino acid/ pramlintide | [NaCl] (mM) | [ZnCl$_2$] (mM) | Lag time (h) |
|---|---|---|---|---|---|---|---|
| C6-1 | B2 | 3.9 | 0.75 | 5 | — | —* | <5 |
| C9 | B2 | 2.4 | 0.46 | 3 | 50 | 1* | >10 |
| C6-7 | B1 | 15.3 | 2.28 | 15 | — | —* | <1 |
| C10-1 | B1 | 15.3 | 2.28 | 15 | 100 | 0.23 | >4 |
| C10-2 | B1 | 15.3 | 2.28 | 15 | 100 | 1* | >9 |
| C10-3 | B1 | 15.3 | 2.28 | 15 | 100 | 2* | >10 |
| C6-2 | B3 | 2.8 | 0.3 | 15 | — | —* | <4 |
| C10-4 | B3 | 11.3 | 2.3 | 15 | 100 | 0.23 | >10 |
| C10-5 | B3 | 11.3 | 2.3 | 15 | 100 | 1.2* | >15 |

*composition comprising 0.23 mM of ZnCl$_2$ from the 100 IU/mL human insulin solution Adding and zinc chloride in the solutions containing a co-polyamino acid makes it possible to increase the lag times significantly compared to those obtained with solutions free from salt or zinc.

EXAMPLE CB1

Physical Stability in Vial and Cartridge at 30° C. of 0.6 mg/mL Pramlintide Solutions in the Presence of Co-Polyamino Acid, M-Cresol (29 mM), Glycerin (174 mM) and Different NaCl Concentrations at pH 6.6

Solutions C3-19, C8a-10 and C3-20 are filtered (0.22 µm). 1 mL of solution is introduced into 3 mL self-injection pen glass cartridges and into 3 mL glass vials. The cartridges and the vials are placed in an oven at 30° C. under static conditions then are observed every 2 weeks.

TABLE 15

Physical stability results in vial and in cartridge at 30° C. of compositions with 0.6 mg/mL pramlintide in the presence of co-polyamino acid B14, B19 and B23 and different NaCl concentrations.

| Solution | Co-polyamino acid | Co-polyamino acid concentration mg/mL | ratio | NaCl (mM) | Physical stability 30° C. in vial (weeks) | Physical stability 30° C. in cartridge (weeks) |
|---|---|---|---|---|---|---|
| C1 | — | — | — | — | <7 | — |
| C3-19 | B14 | 2.9 | 3 | — | — | >12 |
| C8a-10 | B19 | 6 | 6 | 50 | >9 | >12 |
| C3-20 | B23 | 12 | 15 | — | >12 | >12 |

The 0.6 mg/mL pramlintide solution at pH 6.6 exhibits a physical stability in vials of less than 7 weeks at 30° C. The 0.6 mg/mL pramlintide solutions at pH 6.6 in the presence of co-polyamino acids B19 and B23 (optionally with NaCl) exhibit a physical stability at 30° C. of greater than 9 weeks in vials.

The 0.6 mg/mL pramlintide solutions at pH 6.6 in the presence of co-polyamino acid and optionally salt exhibit a physical stability at 30° C. of greater than 12 weeks in cartridges.

EXAMPLE CB2

Physical Stability in Vial and Cartridge at 30° C. of 0.6 mg/mL Pramlintide and 100 U/mL Human Insulin Solutions in the Presence of Co-Polyamino Acid, M-Cresol (29 mM), Glycerin (174 mM), Zinc Chloride (229 μM) and Different NaCl Concentrations at pH 6.6

Solutions C6-8, C3-20, C10-6 and C6-9 are filtered (0.22 μm). 1 mL of solution is introduced into 3 mL self-injection pen glass cartridges and into 3 mL glass vials. The cartridges and the vials are placed in an oven at 30° C. under static conditions then are observed every 2 weeks.

TABLE 16

Physical stability results in vial and in cartridge at 30° C. of compositions with 0.6 mg/mL pramlintide and 100 U/mL human insulin in the presence of co-polyamino acid B14, B9 and B23 and different NaCl concentrations.

| Solution | Co-polyamino acid | Co-polyamino acid concentration mg/mL | ratio | NaCl (mM) | Physical stability 30° C. in cartridge (weeks) |
|---|---|---|---|---|---|
| C6-8 | B14 | 2.9 | 3 | — | >12 |
| C3-20 | B19 | 6 | 6 | — | >2 |
| C10-6 | B19 | 6 | 6 | 50 | >12 |
| C6-9 | B23 | 9.6 | 12 | — | >12 |
| C10-7 | B23 | 6 | 8 | 25 | >12 |

The 0.6 mg/mL pramlintide and 100 IU/mL insulin solution at pH 6.6 is turbid.

The 0.6 mg/mL pramlintide and 100 IU/mL human insulin solution at pH 6.6 in the presence of co-polyamino acid and optionally salt exhibit a physical stability at 30° C. of greater than 4 weeks in vials and greater than 2 weeks in cartridges. Adding salt in solution C10-6 containing co-polyamino acid B19 makes it possible to increase the stability in cartridges at 30° C. significantly compared to that obtained with solution C3-20 free from salt.

EXAMPLE CB3

Physical Stability in Cartridge at 37° C. of 0.6 mg/mL Pramlintide Solutions in the Presence of Co-Polyamino Acid, M-Cresol (29 mM), Glycerin (174 mM) and Different NaCl Concentrations at pH 6.6

Solutions C3-19, C8a-10 and C3-21 are filtered (0.22 μm). 1 mL of solution is introduced into 3 mL self-injection pen glass cartridges. The cartridges are placed in an oven at 37° C. under static conditions then are observed every 2 weeks.

TABLE 17

Physical stability results in cartridge at 37° C. of compositions with 0.6 mg/mL pramlintide in the presence of co-polyamino acid and different NaCl concentrations.

| Solution | Co-polyamino acid | Co-polyamino acid concentration mg/mL | ratio | NaCl (mM) | Physical stability 37° C. in cartridge (weeks) |
|---|---|---|---|---|---|
| C3-19 | B14 | 2.9 | 3 | — | >12 |
| C8a-10 | B19 | 6 | 6 | 50 | >9 |
| C3-21 | B23 | 12 | 15 | — | >9 |

The 0.6 mg/mL pramlintide solution at pH 6.6 in the presence of co-polyamino acid and optionally salt exhibits a physical stability at 30° C. of greater than 7 weeks in cartridges.

EXAMPLE CB4

Physical Stability in Cartridge at 37° C. of 0.6 mg/mL Pramlintide and 100 U/mL Human Insulin Solutions in the Presence of Co-Polyamino Acid, M-Cresol (29 mM), Glycerin (174 mM), Zinc Chloride (229 μM) and Different NaCl Concentrations at pH 6.6

Solutions C6-8, C10-6, C6-9 and C10-7 are filtered (0.22 μm). 1 mL of solution is introduced into 3 mL self-injection pen glass cartridges. The cartridges are placed in an oven at 37° C. under static conditions then are observed every 2 weeks.

TABLE 18

Physical stability results in cartridge at 37° C. of compositions with 0.6 mg/mL pramlintide and 100 U/mL human insulin in the presence of co-polyamino acid and different NaCl concentrations.

| Solution | Co-polyamino acid | Co-polyamino acid concentration mg/mL | ratio | NaCl (mM) | Physical stability 37° C. in cartridge (weeks) |
|---|---|---|---|---|---|
| C6-8 | B14 | 2.9 | 3 | — | >8 |
| C10-6 | B19 | 6 | 6 | 50 | >6 |
| C6-9 | B23 | 9.6 | 12 | — | >9 |
| C10-7 | B23 | 6 | 8 | 25 | >9 |

The 0.6 mg/mL pramlintide and 100 IU/mL insulin solution at pH 6.6 is turbid.

The 0.6 mg/mL pramlintide and 100 IU/mL human insulin solution at pH 6.6 in the presence of co-polyamino acid and salt exhibit a physical stability at 37° C. of greater than 6 weeks in cartridges.

The invention claimed is:

1. A composition in the form of an injectable aqueous solution, wherein the pH is comprised from 6.0 to 8.0, comprising at least:
   amylin, an amylin receptor agonist or an amylin analog;
   a co-polyamino acid bearing carboxylate charges carboxylates and at least one hydrophobic radical -Hy according to formula X, said co-polyamino acid being chosen among the co-polyamino acids according to formula I:

$[Q(PLG)_k][Hy]_j[Hy]_{j'}$            Formula I wherein:
  $j \geq 1$; $0 \leq j' \leq n'1$ and $j+j' \geq 1$ and $k \geq 2$,
  said Q being a divalent linear or branched radical or spacer and consisting of an alkyl chain comprising one or a plurality of heteroatoms chosen from the group consisting of nitrogen and oxygen atoms, and/or bearing one or a plurality of heteroatoms consisting of nitrogen and oxygen radicals and/or radicals bearing one or a plurality of heteroatoms consisting of nitrogen and oxygen atoms and/or carboxyl functions,
  PLG being a glutamic or aspartic unit,
  said co-polyamino acid according to formula I bearing at least one hydrophobic radical -Hy, carboxylate charges and consisting of at least two chains of glutamic or aspartic units bound together by the at least divalent linear or branched radical or spacer Q,
  said radical or spacer Q being bound to at least two glutamic or aspartic unit chains of the co-polyamino acid by an amide function and,
  said amide bond binding said radical or spacer Q bound to said at least two chains of glutamic or aspartic units result from the reaction between an amine function and an acid function respectively borne either by a precursor Q' of the radical or spacer Q or by a glutamic or aspartic unit,
  said hydrophobic radical -Hy being bound either to a terminal amino acid unit and then $j \geq 1$, or to a carboxyl function borne by one of the chains of the glutamic or aspartic units of the co-polyamino acid and then $j'=n'1$ and n'1 is the mean number of monomeric units bearing a hydrophobic radical -Hy.

2. The composition according to claim 1, wherein said radical or spacer Q is chosen among the radicals according to formula II:

$$([Q']_q)[-*]_k \qquad \text{Formula II}$$

wherein $1 \leq q \leq 5$,
  the * indicates binding sites of the different groups bound by amide functions, and
  the - represents a binder,
  wherein said radicals Q', identical or different, are chosen from the group consisting of the radicals according to formulas III to VII hereinafter, to form Q:
  by a radical according to Formula III:

  Formula III wherein $1 \leq t \leq 8$,
  by a radical according to formula IV:

  Formula IV wherein:
    at least one of $u''_1$ or $a''_2$ is different to 0,
    if $u''_1 \neq 0$ then $u'_1 \neq 0$ and if $u''_2 \neq 0$ then $u'_2 \neq 0$,
    $u'_1$ and $u'_2$ are identical and different,
    $2 \leq u \leq 4$,
    $0 \leq u'_1 \leq 4$,
    $0 \leq u''_1 \leq 4$,
    $0 \leq u'_2 \leq 4$,
    $0 \leq u''_2 \leq 4$;

by a radical according to formula V:

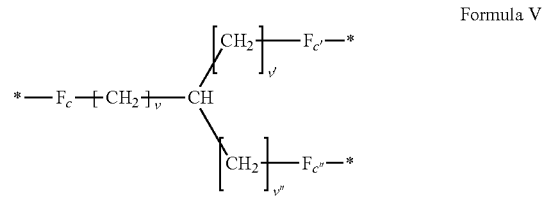  Formula V wherein:
    v, v' and v" identical or different, are integers $\geq 0$,
    $v+v'+v'' \leq 15$,
    by a radical according to formula VI:

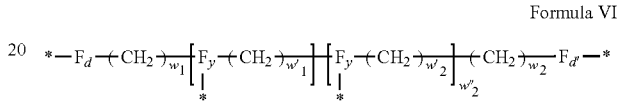  Formula VI wherein:
    $w'_1$ is different to 0,
    $0 \leq w''_2 \leq 1$,
    $w_1 \leq 6$ and $w'_1 \leq 6$ and/or $w_2 \leq 6$ and $w'_2 \leq 6$,
    where in each of the radicals according to formulas III to VII, $F_x = F_a$, $F_b$, $F_c$, $F_d$, $F_{a'}$, $F_{b'}$, $F_{c'}$, $F_{c''}$ and $F_{d'}$ and are identical or different and represent functions —NH— or —CO—, and $F_y$ represents a trivalent nitrogen atom —N=, and
    two radicals Q' being bound together by a covalent bond between a carbonyl function, $F_x$=—CO—, and an amine function $F_x$=—NH— or $F_y$=—N=, thus forming an amide function.

3. The composition according to claim 1, wherein the hydrophobic radical -Hy is chosen among the radicals according to formula X as defined hereinafter:

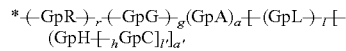  Formula X wherein
  GpR is chosen among the radicals according to formulas VII, VII' or VII":

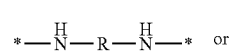  Formula VII

  Formula VII'

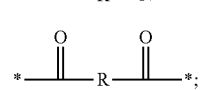  Formula VII"

GpG and GpH identical or different are chosen among the radicals according to formulas XI or XI':

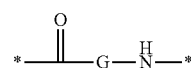  Formula XI

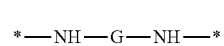  Formula XI'

GpA is chosen among the radicals according to formula VIII:

Formula VIII wherein A' is chosen among the radicals according to VIII', VIII" or VIII''':

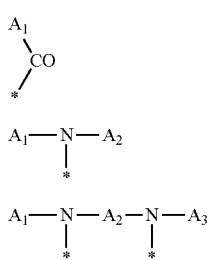

Formula VIII'

Formula VIII"

Formula VIII'''

GpL is chosen among the radicals according to formula XII:

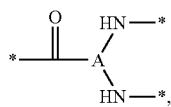
Formula XII

GpC is a radical according to formula IX:

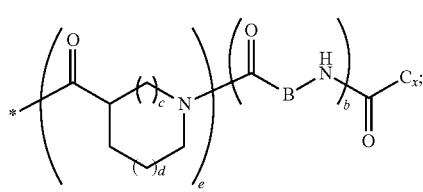
Formula IX the * indicates the binding sites of the different groups bound by amide function;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
l' is an integer equal to 1 or to 2;
r is an integer equal to 0, to 1 or to 2, and
s' is an integer equal to 0 or 1;
A, $A_1$, $A_2$ and $A_3$ identical or different are linear or branched alkyl radicals comprising from 1 to 8 carbon atoms and optionally substituted by a radical from a saturated, unsaturated or aromatic ring;

B is a radical chosen from the group consisting of a non-substituted ether or polyether radical comprising from 4 to 14 carbon atoms and from 1 to 5 oxygen atoms or a linear or branched alkyl radical, and optionally comprising an aromatic nucleus, comprising from 1 to 9 carbon atoms;

$C_x$ is a linear or branched monovalent alkyl radical, and optionally comprising a cyclic part, wherein x indicates the number of carbon atoms and:
  when the hydrophobic radical -Hy bears 1 -GpC, then $9 \leq x \leq 25$,
  when the hydrophobic radical -Hy bears 2 -GpC, then $9 \leq x \leq 15$,
  when the hydrophobic radical -Hy bears 3 -GpC, then $7 \leq x \leq 13$,
  when the hydrophobic radical -Hy bears 4 -GpC, then $7 \leq x \leq 11$,
  when the hydrophobic radical -Hy bears at least 5 -GpC, then $6 \leq x \leq 11$, G is a branched alkyl radical of 1 to 8 carbon atoms, said alkyl radical bearing one or a plurality of free carboxylic acid function(s);

R is a radical chosen from the group consisting of a linear or branched, divalent alkyl radical comprising from 1 to 12 carbon atoms, or a non-substituted ether or polyether radical comprising from 4 to 14 carbon atoms and from 1 to 5 oxygen atoms;

the hydrophobic radical(s) -Hy according to formula X being bound to the co-polyamino acid:
  via a covalent bond between a carbonyl of the hydrophobic radical -Hy and a nitrogen atom borne by the co-polyamino acid thus forming an amide function obtained from the reaction of an amine function borne by the co-polyamino acid and an acid function borne by a precursor Hy' of the hydrophobic radical -Hy, and
  via a covalent bond between a nitrogen atom of the hydrophobic radical -Hy and a carbonyl borne by the co-polyamino acid thus forming an amide function obtained from the reaction of an amine function of a precursor Hy' of the hydrophobic radical -Hy and an acid function borne by the co-polyamino acid, a ratio M being defined as a ratio between the number of hydrophobic radicals and the number of glutamic or aspartic units and being between $0 < M \leq 0.5$;

when a plurality of hydrophobic radicals are borne by a co-polyamino acid then they are identical or different, a degree of polymerization DP in glutamic or aspartic units of the co-polyamino acid chains is comprised from 5 to 250;

free carboxylic acid functions being in the form of alkali cation salt chosen from the group consisting of $Na^+$ and $K^+$.

4. The composition according to claim 1, wherein the co-polyamino acid bearing carboxylate charges and at least one hydrophobic radical -Hy is chosen among the co-polyamino acids according to formula XXXa hereinafter:

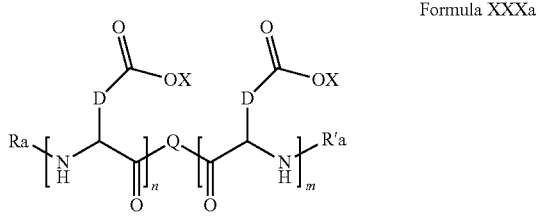

Formula XXXa wherein,
- D represents, independently, either a group —CH$_2$— (aspartic acid) or a group —CH$_2$—CH$_2$— (glutamic acid),
- X represents a cationic entity chosen from the group consisting of alkali cations,
- Ra and R'a, identical or different, are either a hydrophobic radical -Hy, or a radical chosen from the group consisting of a H, a C$_2$ to C$_{10}$ linear acyl group, a C$_3$ to C$_{10}$ branched acyl group, a benzyl, a terminal amino acid unit and a pyroglutamate,
- at least one of Ra and R'a being a hydrophobic radical -Hy,
- Q is as defined in claim 1,
- n+m represents the degree of polymerization DP of the co-polyamino acid, namely the mean number of monomeric units per co-polyamino acid chain and 5≤n+m≤250.

5. The composition according to claim 1, wherein the co-polyamino acid bearing carboxylate charges and hydrophobic radicals is chosen among the co-polyamino acids according to formula XXXa'

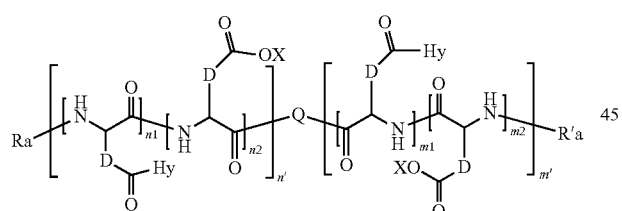

Formula XXXa' wherein:
- D represents, independently, either a group —CH$_2$— (aspartic acid) or a group —CH$_2$—CH$_2$— (glutamic acid),
- X represents a cationic entity chosen from the group consisting of alkali cations,
- Ra and R' a, identical or different, are either a hydrophobic radical -Hy, or a radical chosen from the group consisting of an H, a C$_2$ to C$_{10}$ linear acyl group, a C3 to C$_{10}$ branched acyl group, a benzyl, a terminal amino acid unit and a pyroglutamate,
- at least one of Ra and R' a being a hydrophobic radical -Hy,
- Q is as defined in claim 1,
- n$_1$+m$_1$ represents the number of glutamic units or aspartic units of the chains of the co-polyamino acid bearing a radical -Hy,
- n$_2$+m$_2$ represents the number of glutamic units or aspartic units of the chains of the co-polyamino acid not bearing a radical -Hy,
- n$_1$+n$_2$=n' and m$_1$+m$_2$=m',
- n'+m' represents the degree of polymerization DP of the co-polyamino acid, namely the mean number of monomeric units per co-polyamino acid chain and 5≤n'+m'≤250.

6. The composition according to claim 1, wherein the co-polyamino acid bearing carboxylate charges and hydrophobic radicals is chosen among the co-polyamino acids according to formula XXXb hereinafter:

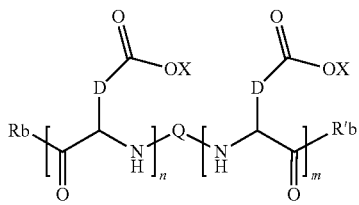

Formula XXXb wherein,
- D represents, independently, either a group —CH$_2$— (aspartic acid) or a group —CH$_2$—CH$_2$— (glutamic acid),
- X represents a cationic entity chosen from the group consisting of alkali cations,
- Rb and R'b, identical or different, are either a hydrophobic radical -Hy, or a radical chosen from the group consisting of an H, a C$_2$ to C$_{10}$ linear acyl group, a C$_3$ to C$_{10}$ branched acyl group, a benzyl, a terminal amino acid unit and a pyroglutamate,
- at least one of Rb and R'b is a hydrophobic radical -Hy,
- Q is as defined in claim 1,
- n+m represents the degree of polymerization DP of the co-polyamino acid, namely the mean number of monomeric units per co-polyamino acid chain and 5≤n+m≤250.

7. The composition according to claim 1, wherein the co-polyamino acid bearing carboxylate charges and hydrophobic radicals is chosen among the co-polyamino acids according to formula XXXb' hereinafter:

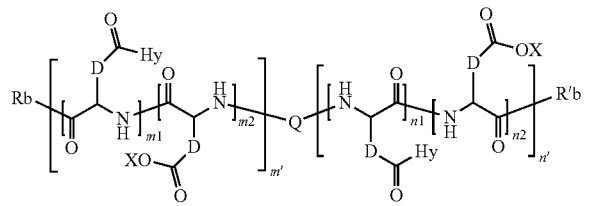

Formula XXXb' wherein:
- D represents, independently, either a group —CH$_2$— (aspartic acid) or a group —CH$_2$—CH$_2$— (glutamic acid), X represents a cationic entity chosen from the group consisting of alkali cations, Q is as defined in claim 1, Rb and R'b, identical or different, are either a hydrophobic radical -Hy, or a radical chosen from the group consisting of an —OH, an amine group, a terminal amino acid unit and a pyroglutamate, at least one of Rb and R'b is a hydrophobic radical -Hy, n1+m1 represents the number of glutamic units or aspartic units of the chains of the co-polyamino acid bearing a radical -Hy, n2+m2 represents the number of glutamic units or aspartic units of the chains of the co-polyamino acid not bearing a radical -Hy, n1+n2=n' and m1+m2=m', n'+m' represents the degree of polymerization DP of the co-polyamino acid, namely the mean number of monomeric units per co-polyamino acid chain, and $5 \leq n'+m' \leq 250$.

8. The composition according to claim 1, wherein the co-polyamino acid bearing carboxylate charges and hydrophobic radical is chosen from among the co-polyamino acids according to formulas XXXa, XXXa', XXXb or XXXb':

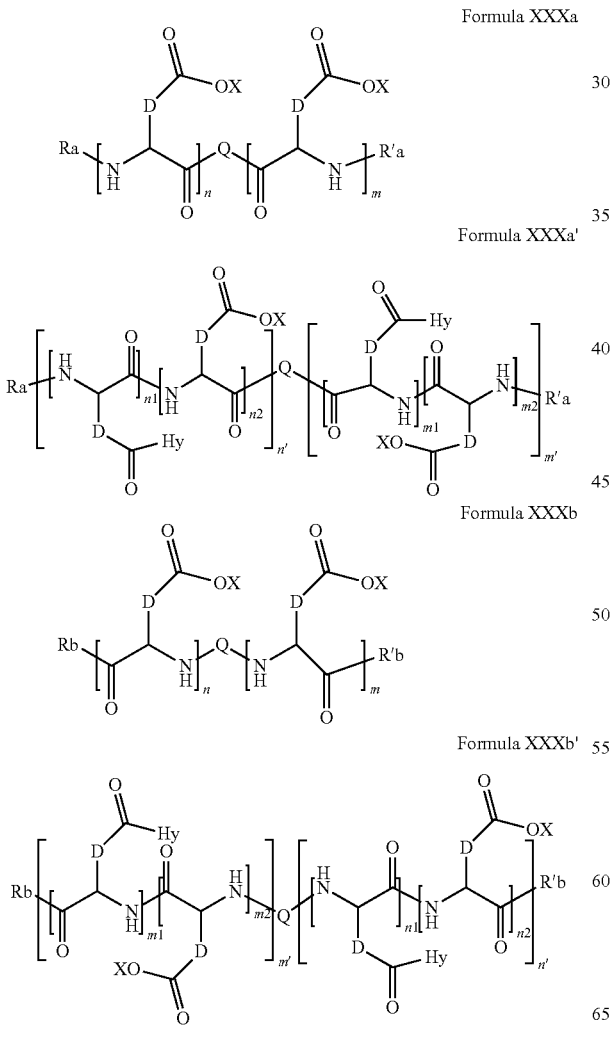

wherein the group D is a group —$CH_2$— (aspartic unit),

X represents a cationic entity chosen from the group consisting of alkali cations, Ra and R'a, identical or different, are either a hydrophobic radical -Hy, or a radical chosen from the group consisting of an H, a $C_2$ to $C_{10}$ linear acyl group, a C3 to $C_{10}$ branched acyl group, a benzyl, a terminal amino acid unit and a pyroglutamate, at least one of Ra and R'a being a hydrophobic radical -Hy, Rb and R'b, identical or different, are either a hydrophobic radical -Hy, or a radical chosen from the group consisting of an H, a $C_2$ to $C_m$ linear acyl group, a $C_3$ to $C_{10}$ branched acyl group, a benzyl, a terminal amino acid unit and a pyroglutamate, at least one of Rb and R'b is a hydrophobic radical -Hy, Q is as defined in claim 1, $n_1+m_1$ represents the number of glutamic units or aspartic units of the chains of the co-polyamino acid bearing a radical -Hy, $n_2+m_2$ represents the number of glutamic units or aspartic units of the chains of the co-polyamino acid not bearing a radical -Hy, $n_1+n_2=n'$ and $m_1+m_2=m'$, n+m and n'+m' represent the degree of polymerization DP of the co-polyamino acid, namely the mean number of monomeric units per co-polyamino acid chain, and $5 \leq n+m \leq 250$ and $5 \leq n'+m' \leq 250$.

9. The composition according to claim 1, wherein the co-polyamino acid bearing carboxylate charges and hydrophobic radicals is chosen from among the co-polyamino acids according to formulas XXXa, XXXa', XXXb or XXXb':

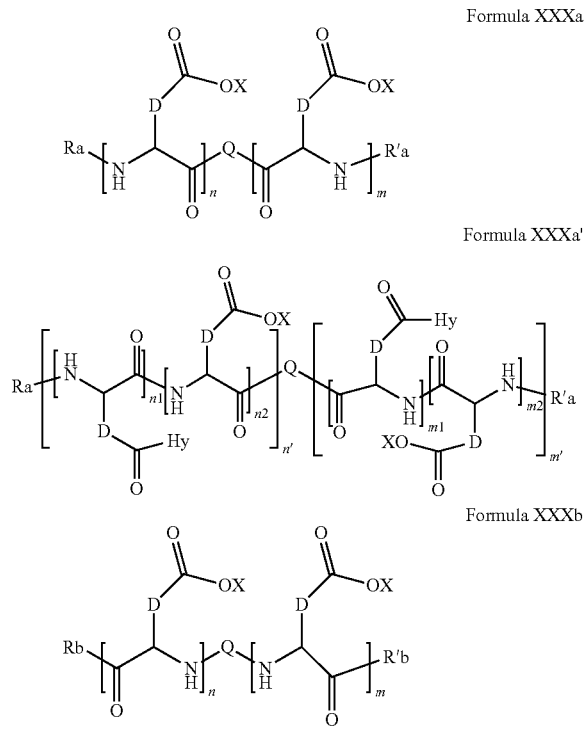

-continued

Formula XXXb'

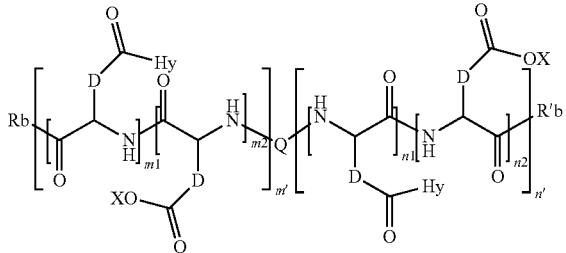

wherein
the group D is a group —CH$_2$—CH$_2$— (glutamic unit),
X represents a cationic entity chosen from the group consisting of alkali cations,
Ra and R'a, identical or different, are either a hydrophobic radical -Hy, or a radical chosen from the group consisting of an H, a C$_2$ to C$_{10}$ linear acyl group, a C3 to C$_{10}$ branched acyl group, a benzyl, a terminal amino acid unit and a pyroglutamate,
at least one of Ra and R'a being a hydrophobic radical -Hy,
Rb and R'b, identical or different, are either a hydrophobic radical -Hy, or a radical chosen from the group consisting of an H, a C$_2$ to C$_m$ linear acyl group, a C$_3$ to C$_{10}$ branched acyl group, a benzyl, a terminal amino acid unit and a pyroglutamate,
at least one of Rb and R'b is a hydrophobic radical -Hy,
Q is as defined in claim 1,
$n_1+m_1$ represents the number of glutamic units or aspartic units of the chains of the co-polyamino acid bearing a radical -Hy,
$n_2+m_2$ represents the number of glutamic units or aspartic units of the chains of the co-polyamino acid not bearing a radical -Hy,
$n_1+n_2=n'$ and $m_1+m_2=m'$,
n+m and n'+m' represent the degree of polymerization DP of the co-polyamino acid, namely the mean number of monomeric units per co-polyamino acid chain, and $5 \le n+m \le 250$ and $5 \le n'+m' \le 250$.

10. The composition according to claim 1, wherein the molar ratio of co-polyamino acid/amylin, amylin receptor agonist or amylin analog is greater than or equal to 1.

11. The composition according to claim 1, wherein the amylin, amylin receptor agonist or amylin analog is amylin.

12. The composition according to claim 1, wherein the amylin, amylin receptor agonist or amylin analog is pramlintide.

13. The composition according to claim 1, wherein the composition further comprises a prandial insulin.

14. The composition according to claim 13, wherein the molar ratio of co-polyamino acid/insulin is greater than or equal to 1.

15. The composition according to claim 1, wherein said composition has a stability measured by ThT greater than that of a reference composition comprising amylin, an amylin receptor agonist or an amylin agonist but not comprising co-polyamino acid bearing carboxylate charges and hydrophobic radicals -Hy, said ThT monitoring being carried out under accelerated stability conditions: under stirring and at 37° C.

16. A co-polyamino acid bearing carboxylate charges carboxylates and at least one hydrophobic radical according to formula X, said co-polyamino acid being chosen among the co-polyamino acids according to formula I:

[Q(PLG)k][Hy]j[Hy]j'    Formula I $j \ge 1$; $0 \le j' \le n'1$ and $j+j' \ge 1$ and $k \ge 2$,
said Q being a divalent linear or branched radical or spacer and consisting of an alkyl chain comprising one or a plurality of heteroatoms chosen from the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions,
PLG being a glutamic or aspartic unit,
said co-polyamino acid according to formula I bearing at least one hydrophobic radical -Hy, carboxylate charges and consisting of at least two chains of glutamic or aspartic units bound together by the at least divalent linear or branched radical or spacer Q,
said radical or spacer Q being bound to at least two glutamic or aspartic unit chains of the co-polyamino acid by an amide function and,
said amide bond binding said radical or spacer Q bound to said at least two chains of glutamic or aspartic units result from the reaction between an amine function and an acid function respectively borne either by a precursor Q' of the radical or spacer Q or by a glutamic or aspartic unit,
said hydrophobic radical -Hy being bound either to a terminal amino acid unit and then $j \ge 1$, or to a carboxyl function borne by one of the chains of the glutamic or aspartic units of the co-polyamino acid and then $j'=n'1$ and n'1 is the mean number of monomeric units bearing a hydrophobic radical -Hy,
and wherein the at least one hydrophobic radical -Hy according to formula X is as defined hereinafter:

*—(GpR)$_r$—(GpG)$_g$(GpA)$_a$—(GpL)$_l$—
(GpH)$_h$GpC]$_{l'}$]$_{a'}$    Formula X wherein
GpR is chosen among the radicals according to formulas VII, VII' or VII":

*—$\overset{H}{N}$—R—$\overset{H}{N}$—*    or    Formula VII

*—$\overset{O}{\underset{\|}{C}}$—R—$\overset{H}{N}$—*    or    Formula VII'

*—$\overset{O}{\underset{\|}{C}}$—R—$\overset{O}{\underset{\|}{C}}$—*;    Formula VII"

GpG and GpH identical or different are chosen among the radicals according to formulas XI or XI':

*—$\overset{O}{\underset{\|}{C}}$—G—$\overset{H}{N}$—*    Formula XI

*—NH—G—NH—*    Formula XI'

GpA is chosen among the radicals according to formula VIII:

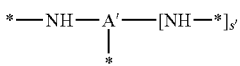
Formula VIII wherein A' is chosen among the radicals according to VIII', VIII" or VIII''':

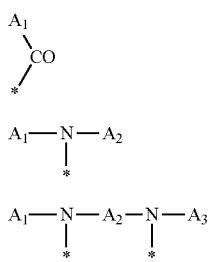

GpL is chosen among the radicals according to formula XII:

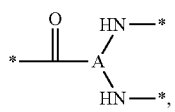
Formula XII

GpC is a radical according to formula IX:

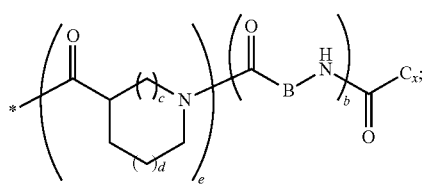
Formula IX the * indicates the binding sites of the different groups bound by amide function;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
l' is an integer equal to 1 or to 2;
r is an integer equal to 0, to 1 or to 2, and
s' is an integer equal to 0 or 1;
A, $A_1$, $A_2$ and $A_3$ identical or different are linear or branched alkyl radicals comprising from 1 to 8 carbon atoms and optionally substituted by a radical from a saturated, unsaturated or aromatic ring;

B is a radical chosen from the group consisting of a non-substituted ether or polyether radical comprising from 4 to 14 carbon atoms and from 1 to 5 oxygen atoms or a linear or branched alkyl radical, and optionally comprising an aromatic nucleus, comprising from 1 to 9 carbon atoms;

$C_x$ is a linear or branched monovalent alkyl radical, and optionally comprising a cyclic part, wherein x indicates the number of carbon atoms and:
when the hydrophobic radical -Hy bears 1 -GpC, then $9 \leq x \leq 25$,
when the hydrophobic radical -Hy bears 2 -GpC, then $9 \leq x \leq 15$,
when the hydrophobic radical -Hy bears 3 -GpC, then $7 \leq x \leq 13$,
when the hydrophobic radical -Hy bears 4 -GpC, then $7 \leq x \leq 11$,
when the hydrophobic radical -Hy bears at least 5 -GpC, then $6 \leq x \leq 11$, G is a branched alkyl radical of 1 to 8 carbon atoms, said alkyl radical bearing one or a plurality of free carboxylic acid function(s);

R is a radical chosen from the group consisting of a linear or branched, divalent alkyl radical comprising from 1 to 12 carbon atoms, or a non-substituted ether or polyether radical comprising from 4 to 14 carbon atoms and from 1 to 5 oxygen atoms;

the hydrophobic radical(s) -Hy according to formula X being bound to the PLG co-polyamino acid:
via a covalent bond between a carbonyl of the hydrophobic radical -Hy and a nitrogen atom borne by the co-polyamino acid thus forming an amide function obtained from the reaction of an amine function borne by the co-polyamino acid and an acid function borne by a precursor Hy' of the hydrophobic radical -Hy, and
via a covalent bond between a nitrogen atom of the hydrophobic radical -Hy and a carbonyl borne by the co-polyamino acid thus forming an amide function obtained from the reaction of an amine function of a precursor Hy' of the hydrophobic radical -Hy and an acid function borne by the co-polyamino acid, a ratio M being defined as a ratio between the number of hydrophobic radicals and the number of glutamic or aspartic units and being between $0 < M \leq 0.5$;

when a plurality of hydrophobic radicals are borne by the co-polyamino acid then they are identical or different;

a degree of polymerization DP in glutamic or aspartic units for the co-polyamino acid chains is comprised from 5 to 250;

free carboxylic acid functions being in the form of alkali cation salt chosen from the group consisting of $Na^+$ and $K^+$.

17. A hydrophobic radical precursor Hy' chosen among the compounds according to formula X' as defined hereinafter:

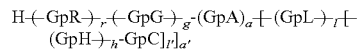
Formula X' wherein

GpR is chosen among the radicals according to formulas VII, VII' or VII":

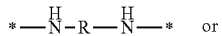
Formula VII

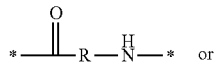
Formula VII'

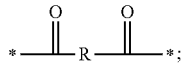
Formula VII";

GpG and GpH identical or different are chosen among the radicals according to formulas XI or XI':

Formula XI

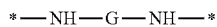
Formula XI'

GpA is chosen among the radicals according to formula VIII:

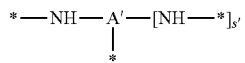
Formula VIII wherein A' is chosen among the radicals according to VIII', VIII" or VIII''':

Formula VIII'

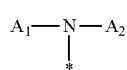
Formula VIII"

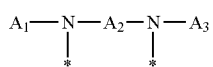
Formula '''

GpL is chosen among the radicals according to formula XII:

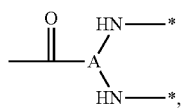
Formula XII

GpC is a radical according to formula IX:

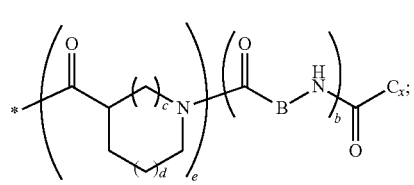
Formula IX the * indicates the binding sites of the different groups bound by amide function;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0 then d is equal to 1 or to 2;

d is an integer equal to 0, to 1 or to 2;

e is an integer equal to 0 or to 1;

g is an integer equal to 0, to 1, to 2, to 3 to 4 to 5 or to 6;

h is an integer equal to 0, to 1, to 2, to 3 to 4 to 5 or to 6;

l is an integer equal to 0 or 1 and l'=1 if l=0 and l'=2 if l=1;

l' is an integer equal to 1 or to 2;

r is an integer equal to 0, 1 or to 2, and s' is an integer equal to 0 or 1;

A, $A_1$, $A_2$ and $A_3$ identical or different are linear or branched alkyl radicals comprising from 1 to 8 carbon atoms and optionally substituted by a radical from a saturated, unsaturated or aromatic ring;

B is a radical chosen from the group consisting of a non-substituted ether or polyether radical comprising from 4 to 14 carbon atoms and from 1 to 5 oxygen atoms or a linear or branched alkyl radical, and optionally comprising an aromatic nucleus, comprising from 1 to 9 carbon atoms;

$C_x$ is a radical chosen from the group consisting of a linear or branched monovalent alkyl radical, and optionally comprising a cyclic part, wherein x indicates the number of carbon atoms and $6 \leq x \leq 25$:

when the hydrophobic radical -Hy bears 1 -GpC, then $9 \leq x \leq 25$, when the hydrophobic radical -Hy bears 2 -GpC, then $9 \leq x \leq 15$, when the hydrophobic radical -Hy bears 3 -GpC, then $7 \leq x \leq 13$, when the hydrophobic radical -Hy bears 4 -GpC, then $7 \leq x \leq 11$, when the hydrophobic radical -Hy bears at least 5 -GpC, then $6 \leq x \leq 11$;

G is a linear or branched divalent alkyl radical of 1 to 8 carbon atoms, said alkyl radical bearing one or a plurality of free carboxylic acid function(s);

R is a radical chosen from the group consisting of a linear or branched, divalent alkyl radical comprising from 1 to 12 carbon atoms, or a non-substituted ether or polyether radical comprising from 4 to 14 carbon atoms and from 1 to 5 oxygen atoms;

the hydrophobic radical(s) -Hy according to formula X being bound to the co-polyamino acid:

via a covalent bond between a carbonyl of the hydrophobic radical -Hy and a nitrogen atom borne by the co-polyamino acid thus forming an amide function obtained from the reaction of an amine function borne by the co-polyamino acid and an acid function borne by a precursor Hy' of the hydrophobic radical -Hy and/or via a covalent bond between a nitrogen atom of the hydrophobic radical -Hy and a carbonyl borne by the co-polyamino acid thus forming an amide function obtained from the reaction of an amine function of a precursor Hy' of the hydrophobic radical -Hy and an acid function borne by the co-polyamino acid;

a ratio M being defined as a ratio between the number of hydrophobic radicals and the number of glutamic or aspartic units being between $0 < M \leq 0.5$;

when a plurality of hydrophobic radicals are borne by the co-polyamino acid then they are identical or different;

a degree of polymerization DP in glutamic or aspartic units of the co-polyamino acid chains is comprised from 5 to 250;

free acid functions being in the form of alkali cation salt chosen from the group consisting of $Na^+$ and $K^+$.

18. A method for improving the physicochemical stability of the composition according to claim 1, by adding one or more ionic species chosen from the group of anions, cations and zwitterions.

* * * * *